(12) United States Patent
Motterlini et al.

(10) Patent No.: US 8,389,572 B2
(45) Date of Patent: Mar. 5, 2013

(54) THERAPEUTIC DELIVERY OF CARBON MONOXIDE

(75) Inventors: Roberto Angelo Motterlini, Genoa (IT); Brian Ernest Mann, Sheffield (GB); Tony Richard Johnson, Sheffield (GB); David Alistair Scapens, High Peak (GB); Rehan Aqil, Cambridge (GB); Trevor Perrior, Cambridge (GB)

(73) Assignee: hemoCORM Limited, Birmingham (GB)

( * ) Notice: Subject to any disclaimer, the term of this patent is extended or adjusted under 35 U.S.C. 154(b) by 498 days.

(21) Appl. No.: 12/223,171

(22) PCT Filed: Jan. 23, 2007

(86) PCT No.: PCT/GB2007/000198
§ 371 (c)(1),
(2), (4) Date: Aug. 24, 2010

(87) PCT Pub. No.: WO2007/085806
PCT Pub. Date: Aug. 2, 2007

(65) Prior Publication Data
US 2011/0015263 A1 Jan. 20, 2011

(30) Foreign Application Priority Data
Jan. 24, 2006 (GB) .................... 0601394.0

(51) Int. Cl.
*A61K 31/28* (2006.01)
*A61K 31/295* (2006.01)
*C07F 15/00* (2006.01)
(52) U.S. Cl. .................... 514/492; 514/502; 556/142
(58) Field of Classification Search .................. 514/492, 514/502; 556/142
See application file for complete search history.

(56) References Cited

U.S. PATENT DOCUMENTS

| | | | |
|---|---|---|---|
| 2,870,180 A | 1/1959 | Kozikowski et al. |
| 3,278,570 A | 10/1966 | Wilkinson et al. |
| 3,694,232 A | 9/1972 | Hall et al. |
| 3,812,166 A | 5/1974 | Wiechert et al. |
| 3,829,504 A | 8/1974 | Hall et al. |
| 3,980,583 A | 9/1976 | Owen et al. |
| 4,189,487 A | 2/1980 | Klosa |
| 4,312,989 A | 1/1982 | Spielvogel et al. |
| 4,322,411 A | 3/1982 | Vinegar et al. |
| 4,535,167 A | 8/1985 | Freidinger |
| 4,613,621 A | 9/1986 | Hormann |
| 4,649,151 A | 3/1987 | Dougherty et al. |
| 4,657,902 A | 4/1987 | Kappas et al. |
| 4,668,670 A | 5/1987 | Ridoeout et al. |
| 4,699,903 A | 10/1987 | Ridoeout et al. |
| 4,709,083 A | 11/1987 | Spielvogel |
| 4,910,211 A | 3/1990 | Imamura et al. |
| 4,938,949 A | 7/1990 | Borch et al. |
| 5,010,073 A | 4/1991 | Kappas et al. |
| 5,086,060 A | 2/1992 | Haley et al. |
| 5,102,670 A | 4/1992 | Abraham et al. |
| 5,254,706 A | 10/1993 | Spielvogel et al. |
| 5,312,816 A | 5/1994 | Spielvogel et al. |
| 5,350,767 A | 9/1994 | Hallberg et al. |
| 5,447,939 A | 9/1995 | Glasky et al. |
| 5,621,000 A | 4/1997 | Arena et al. |
| 5,631,284 A | 5/1997 | Legzdins et al. |
| 5,659,027 A | 8/1997 | Spielvogel et al. |
| 5,664,563 A | 9/1997 | Schroeder et al. |
| 5,670,664 A | 9/1997 | Kao et al. |
| 5,700,947 A | 12/1997 | del Soldato |
| 5,756,492 A | 5/1998 | Buelow et al. |
| 5,767,157 A | 6/1998 | Van Moerkerken |
| 5,801,184 A | 9/1998 | Glasky et al. |
| 5,811,463 A | 9/1998 | Legzdins et al. |
| 5,824,673 A | 10/1998 | Abrams et al. |
| 5,861,426 A | 1/1999 | del Soldato et al. |
| 5,882,674 A | 3/1999 | Herrmann et al. |
| 5,885,621 A | 3/1999 | Head et al. |
| 5,888,982 A | 3/1999 | Perrella et al. |
| 5,891,689 A | 4/1999 | Takle et al. |
| 6,025,376 A | 2/2000 | Laurent et al. |
| 6,025,394 A | 2/2000 | Menander et al. |
| 6,027,936 A | 2/2000 | Glasky et al. |
| 6,040,341 A | 3/2000 | del Soldato et al. |
| 6,051,576 A | 4/2000 | Ashton et al. |
| 6,060,467 A | 5/2000 | Buelow et al. |
| 6,066,333 A | 5/2000 | Willis et al. |
| 6,177,471 B1 | 1/2001 | Menander et al. |
| 6,203,991 B1 | 3/2001 | Nabel et al. |
| 6,211,233 B1 | 4/2001 | del Soldato |
| 6,218,417 B1 | 4/2001 | del Soldato |
| 6,242,432 B1 | 6/2001 | del Soldato |

(Continued)

FOREIGN PATENT DOCUMENTS

DE 4014762 A1 11/1991
EP 0 034 238 8/1981

(Continued)

OTHER PUBLICATIONS

International Search Report for PCT/GB2007/000198, mailed Nov. 8, 2007.
Written Opinion of the International Searching Authority for PCT/GB2007/000198, mailed Nov. 8, 2007.
Motterlini, R. et al., "Carbon Monoxide-Releasing Molecules Characterization of Biochemical and Vascular Activities", Circulation Research, vol. 90, No. 2, pp. E17-E24, (Feb. 8, 2002).

(Continued)

*Primary Examiner* — Raymond Henley, III
(74) *Attorney, Agent, or Firm* — Wolf, Greenfield & Sacks, P.C.

(57) ABSTRACT

Compounds, pharmaceutical compositions and methods for the therapeutic delivery of carbon monoxide to humans and other mammals that employ transition metal complexes having at least a substituted cyclopentadienyl, indenyl or fluorenyl ligand and two or more carbonyl ligands.

24 Claims, 3 Drawing Sheets

U.S. PATENT DOCUMENTS

| | | |
|---|---|---|
| 6,251,927 B1 | 6/2001 | Lai et al. |
| 6,284,752 B1 | 9/2001 | Abrams et al. |
| 6,331,564 B1 | 12/2001 | Brugnara et al. |
| 6,338,963 B1 | 1/2002 | Glasky et al. |
| 6,344,178 B1 | 2/2002 | Alberto et al. |
| 6,350,752 B1 | 2/2002 | Glasky et al. |
| 6,417,182 B1 | 7/2002 | Abrams et al. |
| 6,518,269 B1 | 2/2003 | Camden et al. |
| 6,645,938 B2 | 11/2003 | Oeltgen et al. |
| 6,673,908 B1 | 1/2004 | Stanton |
| 7,011,854 B2 | 3/2006 | Haas et al. |
| 7,045,140 B2 | 5/2006 | Motterlini et al. |
| 7,053,242 B1 | 5/2006 | Alberto et al. |
| 7,964,220 B2 | 6/2011 | Haas et al. |
| 7,968,605 B2 | 6/2011 | de Matos et al. |
| 7,989,650 B2 | 8/2011 | Motterlini et al. |
| 8,236,339 B2 | 8/2012 | Motterlini et al. |
| 2002/0043595 A1 | 4/2002 | Bridgers et al. |
| 2002/0045611 A1 | 4/2002 | Abrams et al. |
| 2002/0049190 A1 | 4/2002 | Bridger et al. |
| 2002/0155166 A1 | 10/2002 | Choi et al. |
| 2002/0165242 A1 | 11/2002 | Glasky et al. |
| 2002/0193363 A1 | 12/2002 | Bridger et al. |
| 2003/0039638 A1 | 2/2003 | Bach et al. |
| 2003/0064114 A1 | 4/2003 | Motterlini et al. |
| 2003/0068387 A1 | 4/2003 | Buelow et al. |
| 2003/0124157 A1 | 7/2003 | Engles et al. |
| 2003/0157154 A1 | 8/2003 | Fuller et al. |
| 2003/0207786 A1 | 11/2003 | Miracle et al. |
| 2003/0219496 A1 | 11/2003 | Otterbein et al. |
| 2003/0219497 A1 | 11/2003 | Otterbein et al. |
| 2004/0052866 A1 | 3/2004 | Otterbein et al. |
| 2004/0067261 A1 | 4/2004 | Haas et al. |
| 2004/0122091 A1 | 6/2004 | Dasseux et al. |
| 2004/0131602 A1 | 7/2004 | Buelow et al. |
| 2004/0143025 A1 | 7/2004 | Buelow et al. |
| 2004/0214900 A1 | 10/2004 | Forbes et al. |
| 2004/0228930 A1 | 11/2004 | Billiar et al. |
| 2004/0258772 A1 | 12/2004 | Otterbein et al. |
| 2005/0048133 A1 | 3/2005 | Pinksy et al. |
| 2005/0175555 A1 | 8/2005 | Stradi et al. |
| 2006/0115542 A1 | 6/2006 | Motterlini et al. |
| 2006/0127501 A1 | 6/2006 | Motterlini et al. |
| 2006/0147548 A1 | 7/2006 | Motterlini et al. |
| 2006/0148900 A1 | 7/2006 | Haas et al. |
| 2006/0233890 A1 | 10/2006 | Haas et al. |
| 2007/0065485 A1 | 3/2007 | Motterlini et al. |
| 2007/0207217 A1 | 9/2007 | Haas et al. |
| 2007/0207993 A1 | 9/2007 | Haas et al. |
| 2007/0219120 A1 | 9/2007 | de Matos et al. |
| 2008/0026984 A1 | 1/2008 | de Matos et al. |
| 2010/0105770 A1 | 4/2010 | Motterlini et al. |
| 2010/0196516 A1 | 8/2010 | Nobre |
| 2011/0038955 A1 | 2/2011 | Rodrigues et al. |
| 2011/0237546 A1 | 9/2011 | Haas et al. |

FOREIGN PATENT DOCUMENTS

| | | |
|---|---|---|
| EP | 0076493 | 4/1983 |
| EP | 0 181 721 | 5/1986 |
| EP | 0 632 026 | 1/1995 |
| FR | 2816212 | 5/2002 |
| GB | 1107510 | 6/1965 |
| GB | 111872.8 | 7/2001 |
| GB | 227135.1 | 12/2002 |
| GB | 227138.5 | 12/2002 |
| GB | 2395431 | 5/2004 |
| GB | 2395432 A | 5/2004 |
| HU | 57595 | 12/1991 |
| HU | 211 084 | 10/1995 |
| WO | 85/04326 A1 | 10/1985 |
| WO | 91/01128 | 2/1991 |
| WO | 91/01301 | 2/1991 |
| WO | 92/03402 | 3/1992 |
| WO | 92/04905 | 4/1992 |
| WO | 93/05795 | 4/1993 |
| WO | 94/01413 | 1/1994 |
| WO | 94/22482 | 10/1994 |
| WO | 95/05814 | 3/1995 |
| WO | 95/09831 | 4/1995 |
| WO | 95/35105 A1 | 12/1995 |
| WO | 96/03125 | 2/1996 |
| WO | 96/09038 | 3/1996 |
| WO | 97/16405 | 5/1997 |
| WO | 97/36615 | 10/1997 |
| WO | 97/37644 | 10/1997 |
| WO | 98/09618 | 3/1998 |
| WO | 98/29115 | 7/1998 |
| WO | 98/38179 | 9/1998 |
| WO | 98/48848 | 11/1998 |
| WO | 99/67231 | 12/1999 |
| WO | 00/10613 | 3/2000 |
| WO | 00/21965 A1 | 4/2000 |
| WO | 00/36113 | 6/2000 |
| WO | 00/56145 | 9/2000 |
| WO | 00/56743 | 9/2000 |
| WO | 00/61537 | 10/2000 |
| WO | 01/12584 | 2/2001 |
| WO | 01/16359 | 3/2001 |
| WO | 01/25243 | 4/2001 |
| WO | 01/28545 | 4/2001 |
| WO | 02/078684 | 10/2002 |
| WO | 02/080923 | 10/2002 |
| WO | 02/092072 | 11/2002 |
| WO | 02/092075 | 11/2002 |
| WO | 02/092075 A3 | 11/2002 |
| WO | 03/000114 | 1/2003 |
| WO | 03/066067 | 8/2003 |
| WO | 03/067598 | 8/2003 |
| WO | 03/072024 | 9/2003 |
| WO | 03/082850 A2 | 10/2003 |
| WO | 03/088923 | 10/2003 |
| WO | 03/088981 | 10/2003 |
| WO | 03/094932 | 11/2003 |
| WO | 03/096977 | 11/2003 |
| WO | 03/103585 | 12/2003 |
| WO | 2004/029033 | 4/2004 |
| WO | 2004/043341 | 5/2004 |
| WO | 2004/045598 | 6/2004 |
| WO | 2004/045599 | 6/2004 |
| WO | 2004/080420 | 9/2004 |
| WO | 2005/013691 A1 | 2/2005 |
| WO | 2005/090400 | 9/2005 |
| WO | 2006/012215 | 2/2006 |
| WO | 2007/073226 | 6/2007 |
| WO | 2007/085806 | 8/2007 |
| WO | 2008/003953 | 1/2008 |
| WO | 2008/069688 | 6/2008 |
| WO | 2008/130261 A1 | 10/2008 |
| WO | 2009/013612 A1 | 1/2009 |

OTHER PUBLICATIONS

[No Author Listed] "supramolecule" IUPAC compendium of chemical terminology. 2$^{nd}$ Ed. 1997. Retrieved from the internet at www.iupac.org/goldbook/SO6153.pdf on May 8, 2006.

[No Author Listed] Biosis Chem Abstracts Database. Accession No. PREV200600414130. 2005. Otterbein et al., Cell Mol Biol (Noisy-le-grand). Oct 3, 2005;51(5):433-40. Abstract.

[No Author Listed] Chemical Abstracts. 2002;137:119662. (FR2816212).

[No Author Listed] Chemical Abstracts. 2004;140:400075. (WO2004/043341).

[No Author Listed] Chemical Abstracts. 2004;141:270758. (Ryter et al.).

[No Author Listed] Chemical Abstracts. 2004;142:211995. (Stein et al.).

[No Author Listed], Solutions, emulsions, suspensions, and extractives. Remington's Pharmaceutical Science. 1985; 17th edition. Gennaro, ed. Ch. 84. p. 1511-2.

Abe et al., The effects of prostacyclin analog OP-41483 on normothermic liver ischemia and reperfusion injury in rats. Prostaglandins Leukot Essent Fatty Acids. Jun. 1993;48(6):417-22.

Abel et al., Anionic halogenopentacarbonyls of chromium, molybdenum, and tungsten. J Chem Soc. 1963:2068-70.

Abel et al., Carbonyl halides of manganese and some related compounds. J Chem Soc. 1959;Part 2:1501-5.

Abel et al., Reaction of molybdenum carbonyl with various halides: a potassium etherate salt. Chem Indust. Apr. 16, 1960;442.

Abraham et al., The biological significance and physiological role of heme oxygenase. Cell Physiol Biochem. 1996;6:129-68.

Adkison et al., Semicarbazone-based inhibitors of cathepsin K, are they prodrugs for aldehyde inhibitors? Bioorg Med Chem Lett. Feb. 15, 2006;16(4):978-83. Epub Nov. 15, 2005. Abstract only.

Akamatsu et al., Heme oxygenase-1-derived carbon monoxide protects hearts from transplant associated ischemia reperfusion injury. FASEB J. Apr. 2004;18(6):771-2. Epub Feb. 20, 2004.

Alberto et al., A novel organometallic aqua complex of technetium for the labeling of biomolecules: synthesis of [99mTc(OH2)3(CO)3]+ from [99mTcO4]− in aqueous solution and its reaction with a bifunctional ligand. J Am Chem Soc. 1998;120:7987-8. Epub Jul. 24, 1998.

Alberto et al., Synthesis and properties of boranocarbonate: a convenient in situ CO source for the aqueous preparation of [(99m)Tc(OH(2))3(CO)3]+. J Am Chem Soc. Apr. 4, 2001;123(13):3135-6. Epub Mar. 13, 2001.

Alessio et al., Carbonyl Derivatives of Chloride-Dimethyl Sulfoxide-Ruthenium(II) Complexes: Synthesis, Structural Characterization, and Reactivity of Ru(CO)x(DMSO)4-xCl2 Complexes (x =1-3). Inorg Chem. 1995;34(19):4722-34.

Alessio et al., Carbonyl Derivatives of Chloride-Dimethyl Sulfoxide-Ruthenium(III) Complexes: Synthesis, Crystal Structure, and Reactivity of [(DMSO)2H][trans-RuCl4(DMSO-O)(CO)] and mer,cis-RuCl3(DMSO-O)2(CO). Inorg Chem. 1995;34(19):4716-21.

Allanson et al., Ultraviolet A (320-400 nm) modulation of ultraviolet B (290-320 nm)—induced immune suppression is mediated by carbon monoxide. J Invest Dermatol. Mar. 3, 2005;124(3):644-50.

Allardyce et al., Development of organometallic (organo-transition metal) pharmaceuticals. Appl Organomet Chem. Jan. 2005;19:1-10.

Amersi et al., Ex vivo exposure to carbon monoxide prevents hepatic ischemia/reperfusion injury through p38 MAP kinase pathway. Hepatology. Apr. 2002;35(4):815-23.

Andreadis et al., Oxidative and nitrosative events in asthma. Free Radic Biol Med. Aug. 1, 2003;35(3):213-25. Review. Abstract only.

Angelici et al., Carboxamido carbonyl complexes of manganese(I). Inorg Chim Acta. Mar. 1968;2:3-7. Abstract only.

Angelici, Preparation, characterization, and reactions of the cis-Dihalotetracarbonylmanganate(I) anions. Inorg Chem. Aug. 1964;3(8):1099-1102.

Aujard et al., Tridemethylisovelleral, a potent cytotoxic agent. Bioorg Med Chem. Nov. 15, 2005;13(22):6145-50. Epub Aug. 1, 2005. Abstract only.

Bagul et al., Carbon monoxide protects against ischemia-reperfusion injury in an experimental model of controlled nonheartbeating donor kidney. Transplantation. Feb. 27, 2008;85(4):576-81.

Bani-Hani et al., Modulation of thrombin-induced neuroinflammation in BV-2 microglia by carbon monoxide-releasing molecule 3. J Pharmacol Exp Ther. Sep. 2006;318(3):1315-22. Epub Jun. 13, 2006.

Bannenberg et al., Therapeutic applications of the gaseous mediators carbon monoxide and hydrogen sulfide. Expert Opin Ther Pat. May 2009;19(5):663-82. Review.

Barkoudah et al., the permissive role of endothelial NO in CO-induced cerebrovascular dilation. Am J Physiol Heart Circ Physiol. Oct. 2004;287(4):H1459-65. Epub Jun. 10, 2004.

Bauer et al., Evidence for a functional link between stress response and vascular control in hepatic portal circulation. Am J Physiol. Nov. 1996;271(5 Pt 1):G929-35.

Bauerováet al., Role of reactive oxygen and nitrogen species in etiopathogenesis of rheumatoid arthritis. Gen Physiol Biophys. Oct. 1999;18 Spec No:15-20. Review. Abstract only.

Beal, Oxidatively modified proteins in aging and disease. Free Radic Biol Med. May 1, 2002;32(9):797-803. Review. Abstract only.

Beaty et al., An in vitro model for the in vivo mobilization of cadmium by chelating agents using 113Cd-NMR spectroscopy. Chem Res Toxicol. Jul.-Aug. 1992;5(4):568-75. Abstract only.

Becker et al., Age-related changes in antibody-dependent cell-mediated cytotoxicity in mouse spleen. Isr J Med Sci. Feb. 1979;15(2):147-50.

Becker et al., NO-independent regulatory site of direct sGC stimulators like YC-1 and BAY 41-2272. BMC Pharmacol. 2001;1:13. Epub Dec. 28, 2001.

Berman et al., Sensitization and catalysis of light-induced decarbonylation of aldehydes. J Am Chem Soc. 1963;85(24):4010-4013.

Beutler, The effect of carbon monoxide on red cell life span in sickle cell disease. Blood. Aug. 1975;46(2):253-9.

Boissiere et al., Exercise and vasorelaxing effects of CO-releasing molecules in hypertensive rats. Med Sci Sports Exerc. Apr. 2006;38(4):652-9.

Botros et al., Interaction between endogenously produced carbon monoxide and nitric oxide in regulation of renal afferent arterioles. Am J Physiol Heart Circ Physiol. Dec. 2006;291(6):H2772-8. Epub Jul. 14, 2006.

Brashears et al., Effect of meat packaging technologies on the safety and spoilage-indicating characteristics of ground beef—Phase 1: safety characteristics. Jun.-Jul. 2006. National Cattleman's Beef Asscoiation. 22 pages. Available at www.fda.gov/ohrms/dockets/dockets/05p0459/05p-0459-c000009-01-vol2.pdf.

Brooks et al., The spoilage characteristics of ground beef packaged in high-oxygen and low-oxygen modified atmosphere packages. Proc. Reciprocal Meat Conference. University of Illinois at Urbana-Champaign. Jun. 18-21, 2006:61-5.

Brouard et al., Carbon monoxide generated by heme oxygenase 1 suppresses endothelial cell apoptosis. J Exp Med. Oct. 2, 2000;192(7):1015-25.

Brüne et al., Inhibition of platelet aggregation by carbon monoxide is mediated by activation of guanylate cyclase. Mol Pharmacol. Oct. 1987;32(4):497-504.

Bundgaard et al., Pro-drugs as delivery systems. Pharm Int. 1981;2:136-40.

Bundgaard et al., Pro-drugs as drug delivery systems XX. Oxazolidines as potential pro-drug types for β-aminoalcohols, aldehydes or ketones. Intl J Pharm. Feb. 1982;10(2):165-75. Abstract only.

Burgmayer et al., Synthesis and structure of a 7-coordinate molybdenum carbonyl fluoride derivative—Et4n Mo(Co)2(S2cnet2)2f. Inorganic Chem. 1985;24:2224-30.

Burleson et al., The effect of dyes used to evaluate the in situ, ex-vivo, and perfused kidney. Invest Urol. Nov. 1981;19(3):165-8. Abstract only. Accession No. PREV198273058212.

Campbell et al., Molecular targets in immune-mediated diseases: the case of tumour necrosis factor and rheumatoid arthritis. Immunol Cell Biol. Oct. 2003;81(5):354-66.

Carroll et al., Ligand abstraction in the reaction of aryldiazonium ions with some iron complexes containing coordinated cysteine, maleonitriledithiol, or triarylphosphine. Can J Chem. 1974;52:1914-22.

Cepinskas et al., Carbon monoxide liberated from carbon monoxide-releasing molecule CORM-2 attenuates inflammation in the liver of septic mice. Am J Physiol Gastrointest Liver Physiol, Jan. 2008; 294:G184-G191. Epub Nov. 8, 2007.

Chakravortty et al., Inducible nitric oxide synthase and control of intracellular bacterial pathogens. Microbes Infect. Jun. 2003;5(7):621-7. Review. Abstract only.

Chatterjee, Water-soluble carbon monoxide-releasing molecules: helping to elucidate the vascular activity of the 'silent killer'. Br J Pharmacol. Jun. 2004;142(3):391-3. Epub May 17, 2004.

Chauveau et al., Gene transfer of heme oxygenase-1 and carbon monoxide delivery inhibit chronic rejection. Am J Transplant. Aug. 2002;2(7):581-92.

Chlopicki et al., Carbon monoxide released by CORM-3 inhibits human platelets by a mechanism independent of soluble guanylate cyclase. Cardiovasc Res. Jul. 15, 2006;71(2):393-401. Epub Mar. 22, 2006.

Cihonski et al., Crown ethers in inorganic chemistry—preparation and characterization of group 6 pentacarbonyl hydroxides and fluorides. Inorganic Chem. 1975;14(7):1717-20.

Clark et al., Cardioprotective actions by a water-soluble carbon monoxide-releasing molecule. Circ Res. Jul. 25, 2003;93(2):e2-8. Epub Jul. 3, 2003.

Clark et al., Heme oxygenase-1—derived bilirubin ameliorates postischemic myocardial dysfunction. Am J Physiol Heart Circ Physiol. Feb. 2000;278(2):H643-51.

Clark et al., Measuring left ventricular function in the normal, infarcted and CORM-3—preconditioned mouse heart using complex admittance-derived pressure volume loops. J Pharmacol Methods Toxicol. Mar.-Apr. 2009;59(2):94-9.

Coburn et al., Endogenous carbon monoxide production in man. J Clin Invest. Jul. 1963;42(7):1172-8.

Coceani et al., Carbon monoxide formation in the ductus arteriosus in the lamb: implications for the regulation of muscle tone. Br J Pharmacol. Feb. 1997;120(4):599-608.

Coceani, Carbon monoxide in vasoregulation: the promise and the challenge. Circ Res. Jun. 23, 2000;86(12):1184-6. Review.

Cohen et al., Dithiobenzoatotetracarbonylmanganese(I). Inorg Chem. 1964;3(11):1641-42.

Conant et al., Trimethylacetaldehyde and dimethylethylacetaldehyde. J Am Chem Soc. Apr. 1929;51(4):1246-55.

Cotton et al., Dimethyl- and diethyldithiocarbamate complexes of some metal carbonyl compounds. Inorg Chem. Jun. 2, 1964;3(10):1398-1402.

Cotton et al., X-ray molecular structures of Mn(CO)5(O2CCF3) and Mn(CO)3(C5H5N)2(O2CCF3). Inorg Chem. 1981;20(4):1287-91.

Coville et al., Steric measurement of substituted cyclopentadiene ligands and the synthesis and proton NMR spectral analysis of [(.eta. 5-C5H4R)Fe(CO)(L)I] complexes with variable R. Organometallics. 1992;11(3):1082-90.

Crabtree, Immune and inflammatory responses to *Helicobacter pylori* infection. Scandinavian J Gastroenterology. 1996;31(s215):3-10. Abstract only.

De Backer et al., Role of the soluble guanylyl cyclase alpha1/alpha2 subunits in the relaxant effect of CO and CORM-2 in murine gastric fundus. Naunyn Schmiedebergs Arch Pharmacol. Nov. 2008;378(5):493-502. Epub Jun. 18, 2008.

De Backer et al., Water-soluble CO-releasing molecules reduce the development of postoperative ileus via modulation of MAPK/HO-1 signalling and reduction of oxidative stress. Gut. Mar. 2009;58(3):347-56. Epub Nov. 20, 2008.

De Filippo et al., Inductive effect in dithiocarbanate decomposition mechanism. J Org Chem. 1973;38(3):560-3.

Desmard et al., A carbon monoxide-releasing molecule (CORM-3) exerts bactericidal activity against *Pseudomonas aeruginosa* and improves survival in an animal model of bacteraemia. FASEB J. Apr. 2009;23(4):1023-31. Epub Dec. 18, 2008.

Desmard et al., Carbon monoxide reduces the expression and activity of matrix metalloproteinases 1 and 2 in alveolar epithelial cells. Cell Mol Biol (Noisy-le-grand). Sep. 30, 2005;51(4):403-8.

Dharmaraj, Ruthenium (II) complexes containing bidentate Schiff bases and their antifungal activity. Transition Metal Chemistry. 2001; 26(1-2): 105-109.

Di Pascoli et al., Chronic CO levels have [corrected] a beneficial effect on vascular relaxation in diabetes. Biochem Biophys Res Commun. Feb. 17, 2006;340(3):935-43. Epub Dec. 27, 2005. Erratum in: Biochem Biophys Res Commun. Mar. 14, 2006;342(3):1003.

Diamantis et al., Preparation and properties of ethylenediaminetetraacetate complexes of ruthenium(II) with dinitrogen, carbon monoxide, and other π-acceptor ligands. Inorg Chem. 1981;20:1142-50.

Douglas et al., Preparation of some group Vi fluorometal carbonyl derivatives. J Organometal Chem. 1974;65:65-9.

Drew et al., Synthesis, spectral properties, and reactions of manganese and rhenium pentacarbonyl phosphine and phosphite cation derivatives and related complexes. Inorg. Chem. 1975;14(7):1579-84.

Dröge, Free radicals in the physiological control of cell function. Physiol Rev. Jan. 2002;82(1):47-95. Review.

Duchene et al., Cyclodextrins in targeting. Application to nanoparticles. Adv Drug Deliv Rev. Mar. 1, 1999;36(1):29-40.

Duckers et al., Heme oxygenase-1 protects against vascular constriction and proliferation. Nat Med. Jun. 2001;7(6):693-8.

Durante, Heme oxygenase-1 in growth control and its clinical application to vascular disease: J Cell Physiol. Jun. 2003;195(3):373-82. Review.

Egli et al., Organometallic 99mTc-aquaion labels peptide to an unprecedented high specific activity. J Nucl Med. Nov. 1999;40(11):1913-7.

Elliott et al., Nitric oxide: a regulator of mucosal defense and injury. J Gastroenterol. Dec. 1998;33(6):792-803. Review. Abstract only.

El-Kholy, Catalysis by crown ether complexes—part III effect of cation on the catalytic activity of crown ether—alkali metal halide complexes in the liquid phase oxidation of ethylbenzene. Egypt J Chem. 1979;22(1):23-8.

Fairlamb et al., η4-pyrone iron(0)carbonyl complexes as effective CO-releasing molecules (CO-RMs). Bioorg Med Chem Lett. Feb. 15, 2006;16(4):995-8. Epub Nov. 11, 2005.

Fang, Antimicrobial reactive oxygen and nitrogen species: concepts and controversies. Nat Rev Microbiol. Oct. 2004;2(10):820-32. Review. Abstract only.

Feldmann et al., Anti-TNF alpha therapy of rheumatoid arthritis: what have we learned? Annu Rev Immunol. 2001;19:163-96. Review.

Ferrándiz et al., Treatment with a CO-releasing molecule (CORM-3) reduces joint inflammation and erosion in murine collagen-induced arthritis. Ann Rheum Dis. Sep. 2008;67(9):1211-7. Epub Dec. 6, 2007.

Ferrier et al., FTIR spectrometric study of geometrical isomers of dicarbonyl ferrobiscyteinate influence of the counter cation.J Molec Struct. 1995;344(3):189-93.

Fischer et al., Methylpyridin-Chrom(O)-Tricarbonyl. Zeitschrift Fur Naturforschung Part-B-Chemie Biochemie Biophysik Biologie Und Verwandten Gebiete. 1959;14:736-7. English translation provided.

Fischer et al., Uber aromatenkomplexe von metallen .37. zur aromatenkomplexebildung des pyridins mit chromhexacarbonyl. Chemische berichte-recueil. 1960;93:1156-61. English abstract provided.

Fischer, Crystal structure of 1,4,7,10,13-pentaoxacylcopentadecane sodium bromide, C10H20BrNaO5. Zeitschrift fur kristallographie. 1996;211:827-8. English translation provided.

Fiumana et al., Carbon monoxide mediates vasodilator effects of glutamate in isolated pressurized cerebral arterioles of newborn pigs. Am J Physiol Heart Circ Physiol. Apr. 2003;284(4):H1073-9.

Foresti et al., Reviewing the use of carbon monoxide-releasing molecules (CO-RMs) in biology: implications in endotoxin-mediated vascular dysfunction. Cell Mol Biol (Noisy-le-grand). Sep. 30, 2005;51(4):409-23.

Foresti et al., The heme oxygenase pathway and its interaction with nitric oxide in the control of cellular homeostasis. Free Radic Res. Dec. 1999;31(6):459-75. Review.

Foresti et al., Vasoactive properties of CORM-3, a novel water-soluble carbon monoxide-releasing molecule. Br J Pharmacol. Jun. 2004;142(3):453-60. Epub May 17, 2004.

Frangogiannis et al., The inflammatory response in myocardial infarction. Cardiovasc Res. Jan. 2002;53(1):31-47. Review.

Friebe et al., Sensitizing soluble guanylyl cyclase to become a highly CO-sensitive enzyme. EMBO J. Dec. 16, 1996;15(24):6863-8.

Friebe et al., YC-1 potentiates nitric oxide- and carbon monoxide-induced cyclic GMP effects in human platelets. Mol Pharmacol. Dec. 1998;54(6):962-7.

Fujita et al., Paradoxical rescue from ischemic lung injury by inhaled carbon monoxide driven by derepression of fibrinolysis. Nat Med. May 2001;7(5):598-604.

Fukuda et al., Induction of heme oxygenase-1 (HO-1) after traumatic brain injury in the rat. Neurosci Lett. Oct. 20, 1995;199(2):127-30.

Furchgott et al., Endothelium-dependent and—independent vasodilation involving cyclic GMP: relaxation induced by nitric oxide, carbon monoxide and light. Blood Vessels. 1991;28(1-3):52-61.

Giboreau et al., Procedure for the preparation of pure dithiocarbamates. J Org Chem. 1994;59:1205-7.

Gordeuk et al., Carbonyl iron therapy for iron deficiency anemia. Blood. Mar. 1986;67(3):745-52.

Greener et al., Now you're signaling, with gas: gasotransmitters open a window on biology and drug development. The Scientist. 2004;18(17):20-2. Epub Sep. 13, 2004.

Günther et al., Carbon monoxide protects pancreatic beta-cells from apoptosis and improves islet function/survival after transplantation. Diabetes. Apr. 2002;51(4):994-9. MEDLINE Abstract. Accession No. NLM11916917.

Guo et al., Administration of a CO-releasing molecule at the time of reperfusion reduces infarct size in vivo. Am J Physiol Heart Circ Physiol. May 2004;286(5):H1649-53. Epub Jan. 2, 2004.

Haag et al., Polymer therapeutics: concepts and applications. Angew Chem Int Ed Engl. Feb. 13, 2006;45(8):1198-215. Review. Abstract only.

Haddleton et al., [N-Alkyl-(2-pyridyl)methanimine]copper(I) complexes: characterisation and application as catalysts for atom-transfer polymerisation. Eur J Inorg Chem. Dec. 7, 1998;1998(11):1799-1806. Abstract only.

Haddleton et al., Atom transfer polymerization of methyl methacrylate mediated by alkylpyridylmethanimine type ligands, copper(I) bromide, and alkyl halides in hydrocarbon solution. Macromolecules. 1999;32(7):2110-19. Abstract only.

Hadjigogos, The role of free radicals in the pathogenesis of rheumatoid arthritis. Panminerva Med. Mar. 2003;45(I):7-13. Review. Abstract only.

Hall et al., DNA interaction with metal complexes and salts of substituted boranes and hydroborates in murine and human tumor cell lines. Anticancer Drugs. Aug. 1991;2(4):389-99.

Hall et al., The anti-inflammatory activity of boron derivatives in rodents. Met Based Drugs. 1995;2(1):1-12.

Hall et al., The anti-inflammatory activity of metal complexes and salts of amine carboxyboranes. Appl Organomett Chem. 1994;8:473-80.

Hall et al., The hypolipidemic activity of metal complexes of amine carboxyboranes in rodents. Met Based Drugs. 1994;1(4):329-36.

Hancock et al., Antibody-induced transplant arteriosclerosis is prevented by graft expression of anti-oxidant and anti-apoptotic genes. Nat Med. Dec. 1998;4(12):1392-6.

Henricks et al., Reactive oxygen species as mediators in asthma. Pulm Pharmacol Ther. 2001;14(6):409-20. Review. Abstract only.

Herrick et al., Flash photolytic investigation of photinduced carbon monoxide dissociation from dinuclear manganese carbonyl compounds. Inorg Chem. 1984;23:4550-3.

Hieber et al., Derivate des Mangancarbonyls mit schwefelorganischen Liganden. Chemische Berichte. 1966;99(7):2312-21. English abstract provided.

Hitchon et al., Oxidation in rheumatoid arthritis. Arthritis Res Ther. 2004;6(6):265-78. Epub Oct. 13, 2004. Review.

Hogg, Free radicals in disease. Semin Reprod Endocrinol. 1998;16(4):241-8. Review. Abstract only.

Holmuhamedov et al., Mitochondrial ATP-sensitive K+ channels modulate cardiac mitochondrial function. Am J Physiol. Nov. 1998;275(5 Pt 2):H1567-76.

Hosgood et al., Application of nitric oxide and carbon monoxide in a model of renal preservation. Br J Surg. Aug. 2008;95(8):1060-7.

Huang et al., Photolysis of the histidine-heme-CO complex. J Am Chem Soc. Nov. 1, 1991;113:9141-4.

Huebers et al., Absorption of carbonyl iron. J Lab Clin Med. Nov. 1986;108(5):473-8.

Ignatev et al., Reactivity of perfluoroakyl halides towards nucleophiles. Russ J Electrochem. Dec. 1995;31(12):1235-9. Translated from Elektrokhimiya. 1995;31(12):1337-42.

Jander et al., Neutralisationenanaloge reaktionen in essigaureanhybrid. Zietschrift fur anorganische chemie. 1948;255:238-52. English abstract provided.

Jellum et al., Quantitative determination of biologically important thiols and disulfides by gas-liquid chromatography. Analyt Biochem. 1969;31:339-47. Abstract only.

Johansen et al., Spectrophotometric determination of the rates of hydrolysis of aldehyde-releasing pro-drugs in aqueous solution and plasma. Intl J Pharma. Dec. 1982;13(1):89-98. Abstract only.

Johnson et al., Metal carbonyls as pharmaceuticals? [Ru(CO)3C1(glycinate)], a CO-releasing molecule with an extensive aqueous solution chemistry. Dalton Trans. Apr. 21, 2007;(15):1500-8. Epub Mar. 8, 2007.

Johnson et al., Metal carbonyls: a new class of pharmaceuticals? Angew Chem Int Ed Engl. Aug. 18, 2003;42(32):3722-9.

Johnson et al., Role of endogenous carbon monoxide in central regulation of arterial pressure. Hypertension. Oct. 1997;30(4):962-7.

Jozkowicz et al., Heme oxygenase and angiogenic activity of endothelial cells: stimulation by carbon monoxide and inhibition by tin protoporphyrin-IX. Antioxid Redox Signal. Apr. 2003;5(2):155-62.

Kamimura et al., The protective effect of carbon monoxide on the ischemia-induced cell death. The J Biochem. Aug. 2002;74(8):926. Japanese abstract. English translation provided.

Kharitonov et al., Basis of guanylate cyclase activation by carbon monoxide. Proc Natl Acad Sci U S A. Mar. 28, 1995;92(7):2568-71.

Kharitonov et al., Kinetics and equilibria of soluble guanylate cyclase ligation by CO: effect of YC-1. Biochemistry. Aug. 17, 1999;38(33):10699-706.

Krueger et al., Potential of tumor necrosis factor inhibitors in psoriasis and psoriatic arthritis. Arch Dermatol. Feb. 2004;140(2):218-25. Review.

Kubic et al., Metabolism of dihalomethanes to carbon monoxide. I. In vivo studies. Drug Metab Dispos. Jan.-Feb. 1974;2(1):53-7. Abstract only.

Kuiate et al., Composition of the essential oil from leaves and flowers of *Dichrocephala integrifolia* (L.) O. Kuntze Chev. From Cameroon. Flavour and Fragrance J. Nov./Dec. 1999;14(6):419-20. Abstract only.

Lambert et al., O,O'-Diphenyldithiophosphatotetracarbonylmanganese(I) and related compounds. Inorg Chem. 1966;5(7):1287-9.

Lawton et al., Myocardial oxygen consumption in the rabbit heart after ischemia: hyperpolarized arrest with pinacidil versus depolarized hyperkalemic arrest. Circulation. Nov. 4, 1997;96(9 Suppl):11-247-52.

Ledger, Carbon monoxide-releasing metal carbonyls: a new class of pharmaceuticals? Drug Disc Today. Dec. 2003;8(23):1096.

Lee et al., Heme oxygenase-1 mediates the anti-inflammatory effect of interleukin-10 in mice. Nat Med. Mar. 2002;8(3):240-6.

Levrand et al., Controlled release of volatile aldehydes and ketones by reversible hydrazone formation—classical profragrances are getting dynamic. Chem. Commun. 2006;28:2965-7. Epub Apr. 3, 2006.

Li et al., Carbon monoxide protects PC12 cells from peroxynitrite-induced apoptotic death by preventing the depolarization of mitochondrial transmembrane potential. Biochem Biophys Res Commun. Apr. 14, 2006;342(3):984-90. Epub Feb. 20, 2006.

Lipmann et al., Organometallic Lewis Acids. LI. Reactivity of organometallic Lewis Acids (OC)4Re(OEt2)FBF3 and (OC)2(PPh3)2Ru(FBF3)2. Journal of Organometallic Chemistry. 1994;466(1-2):167-174. English abstract provided.

Loftsson et al., Cyclodextrins in topical drug formulations: theory and practice. Int J Pharm. Aug. 28, 2001;225(1-2):15-30. Review.

Loganson et al., Metal carbonyl complexes with ligands of biological origin. Russ Chem Rev. 1985;54(3):277-92.

Lovell et al., Biologic agents for the treatment of juvenile rheumatoid arthritis: current status. Pediatr Drugs. 2004;6(3):137-46.

Mahmoud et al., Potential anticancer agents. XVI. Isolation of bicyclofarnesane sesquiterpenoids from *Capsicodendron dinisii*. J Nat Prod. May-Jun. 1980;43(3):365-71. Abstract only.

Maines, Heine oxygenase: function, multiplicity, regulatory mechanisms, and clinical applications. FASEB J. Jul. 1988;2(10):2557-68. Review.

Maines, The heme oxygenase system: a regulator of second messenger gases. Annu Rev Pharmacol Toxicol. 1997;37:517-54. Review.

Marks et al., Does carbon monoxide have a physiological function? Trends Pharmacol Sci. May, 1991;12(5):185-8. Review.

Martins et al., Induction of carbon monoxide in the donor reduces graft immunogenicity and chronic graft deterioration. Transplant Proc. Jan.-Feb. 2005;37(1):379-81.

Matsuda et al., Mediators of non-adrenergic non-cholinergic inhibitory neurotransmission in porcine jejunum. Neurogastroenterol Motil. Oct. 2004;16(5):605-12.

Mattes et al., Triply bridged thiobenzoato carbonyl manganates(I) and rhenates(I). The crystal and molecular structure of caesium tris(μ-thiobenzoatos(S))bis(tricarbonyl rhenate). J Organometall Chem. Sep. 25, 1979; 178(1):191-6.

McLaughlin et al., Potentiation of carbon monoxide-induced relaxation of rat aorta by YC-1 [3-(5'-hydroxymethyl-2'-furyl)-1-benzylindazole]. Can J Physiol Pharmacol. Apr. 2000;78(4):343-9.

McMillen et al., Hydrocarbon bond dissociation energies. Ann Rev Phys Chem. Oct. 1982;33:493-532.

Meder et al., Metallkomplexe mit biologisch wichtigen liganden, XLII [1] carbonylmetallkomplexe mit anionen von mehrfunktionellen alpha-aminosaeuren [Metal complexes with biologically important ligands], XLII [1] carbonyl metal complexes with anions of polyfunctional alpha-amino acids]. Zeitschrift fur Naturforschung;1986:1247-54. German language reference. English abstract provided.

Megías et al., The carbon monoxide-releasing molecule tricarbonyldichlororuthenium(II) dimer protects human osteoarthritic chondrocytes and cartilage from the catabolic actions of interleukin-1beta. J Pharmacol Exp Ther. Apr. 2008;325(1):56-61. Epub Jan. 14, 2008.

Miguel et al., Manganese(I) complexes with (tricyclohexylphosphonio)dithiocarboxylate as chelate and unidentate ligand. X-Ray crystal structure of fac-[Mn(CO)3{S2CP(C6H11)3}2]ClO4·H2O. J Chem Soc, Dalton Trans. 1987;12:2875-80.

Mikuls et al., Benefit-risk assessment of infliximab in the treatment of rheumatoid arthritis. Drug Saf. 2003;26(1):23-32. Review. Abstract only.

Miller et al., The pharmacological activities of the metabolites of N-[trimethylamineboryl)-carbonyl]-L-phenylalanine methyl ester. Met Based Drugs. 1996;3(5):219-26.

Moncada et al., Nitric oxide: physiology, pathophysiology, and pharmacology. Pharmacol Rev. Jun. 1991;43(2):109-42.

Moncada et al., The discovery of nitric oxide and its role in vascular biology. Br J Pharmacol. Jan. 2006;147 Suppl 1:S193-201.

Moore et al., Brief inhalation of low-dose carbon monoxide protects rodents and swine from postoperative ileus. Crit Care Med. Jun. 2005;33(6):1317-26.

Morita et al., Carbon monoxide controls the proliferation of hypoxic vascular smooth muscle cells. J Biol Chem. Dec. 26, 1997;272(52):32804-9.

Morita et al., Endothelial cell expression of vasoconstrictors and growth factors is regulated by smooth muscle cell-derived carbon monoxide. J Clin Invest. Dec. 1995;96(6):2676-82.

Morita et al., Smooth muscle cell-derived carbon monoxide is a regulator of vascular cGMP. Proc Natl Acad Sci U S A. Feb. 28, 1995;92(5):1475-9.

Morse et al., Suppression of inflammatory cytokine production by carbon monoxide involves the JNK pathway and AP-1. J Biol Chem. Sep. 26, 2003;278(39):36993-8. Epub Jul. 11, 2003.

Motterlini et al., Bioactivity and pharmacological actions of carbon monoxide-releasing molecules. Curr Pharm Des. 2003;9(30):2525-39.

Motterlini et al., Chapter 16: Studies on the development of carbon-monoxide—releasing molecules: potential applications for the treatment of cardiovascular dysfunction. Ed., Rui Wang. CRC Press, New York. 2002:249-72.

Motterlini et al., Characterization of vasoactive effects elicited by carbon monoxide-releasing molecules. Abstracts 8th Intl Symposium on Mechanisms of Vasodilation. J Vasc Res. May 31-Jun. 3, 2001;055.

Motterlini et al., CORM-A1: a new pharmacologically active carbon monoxide-releasing molecule. FASEB J. Feb. 2005;19(2):284-6. Epub Nov. 19, 2004.

Motterlini et al., Functional and metabolic effects of propionyl-L-carnitine in the isolated perfused hypertrophied rat heart. Mol. Cell Biochem. Oct. 21, 1992;116(1-2):139-45.

Motterlini et al., Heme oxygenase-1-derived carbon monoxide contributes to the suppression of acute hypertensive responses in vivo. Circ Res. Sep. 7, 1998;83(5):568-77. Correction included.

Motterlini et al., Therapeutic applications of carbon monoxide-releasing molecules. Expert Opin Investig Drugs. Nov. 2005;14(11):1305-18. Review.

Motterlini, Vasoactive properties of carbon monoxide-releasing molecules. Biomed Pharmacother. 2002;56(7):349-50.

Moya et al., Metal carbonyl complexes containing heterocyclic nitrogen ligands: Part IX. MnBr(CO)3(3,3'-R-2,2'-biquinoline) compounds. Polyhedron. Mar. 1, 2002; 21(4):439-44. Abstract only.

Mungrue et al., From molecules to mammals: what's NOS got to do with it? Acta Physiol Scand. Oct. 2003;179(2):123-35. Review. Abstract only.

Musameh et al., Improved myocardial function after cold storage with preservation solution supplemented with a carbon monoxide-releasing molecule (CORM-3). J Heart Lung Transplant. Nov. 2007;26(11):1192-8.

Musameh et al., Positive inotropic effects of carbon monoxide-releasing molecules (CO-RMs) in the isolated perfused rat heart. Br J Pharmacol. Dec. 2006;149(8):1104-12. Epub Oct. 23, 2006.

Nagai et al., Unusual CO bonding geometry in abnormal subunits of hemoglobin M Boston and hemoglobin M Saskatoon. Biochemistry. Jul. 2, 1991;30(26):6495-503.

Nakao et al., Carbon monoxide inhalation protects rat intestinal grafts from ischemia/reperfusion injury. Am J Pathol. Oct. 2003;163(4):1587-98.

Nakao et al., Protective effect of carbon monoxide in transplantation. J Cell Mol Med. Jul.-Sep. 2006;10(3):650-71. Review.

Nathan, Points of control in inflammation. Nature. Dec. 19-26, 2002;420(6917):846-52. Review.

Ndisang et al., Modulation of the immunological response of guinea pig mast cells by carbon monoxide. Immunopharmacology. Jun. 1999;43(1):65-73.

Neto et al., Protection of transplant-induced renal ischemia-reperfusion injury with carbon monoxide. Am J Physiol Renal Physiol. Nov. 2004;287(5):F979-89. Epub Aug. 3, 2004.

Nitschke et al., Properties of (trifluoromethanesulfonato)pentacarbonylmanganese(I) and—rhenium(I). Reactions in superacid solvents. Inorg Chem. 1985;24(13)1972-8.

Nobre et al., Antimicrobial action of carbon monoxide-releasing compounds. Antimicrob Agents Chemother. Dec. 2007;51(12):4303-7. Epub Oct. 8, 2007.

Nudelman et al., Prodrugs of butyric acid. Novel derivatives possessing increased aqueous solubility and potential for treating cancer and blood diseases. Eur J Med Chem. Jan. 2001;36(1):63-74. Abstract only.

Nudelman et al., The role of intracellularly released formaldehyde and butyric acid in the anticancer activity of acyloxyalkyl esters. J. Med. Chem. Feb. 24, 2005;48(4):1042-54. Epub Jan. 22, 2005. Abstract only.

Nydegger et al., New concepts in organ preservation. Transpl Immunol. May 2002;9(2-4):215-25.

O'Brien et al., Aldehyde sources, metabolism, molecular toxicity mechanisms, and possible effects on human health. Crit Rev Toxicol. Aug. 2005;35(7):609-62. Review.

Otterbein et al., Carbon monoxide has anti-inflammatory effects involving the mitogen-activated protein kinase pathway. Nat Med. Apr. 2000;6(4):422-8.

Otterbein et al., Carbon monoxide provides protection against hyperoxic lung injury. Am J Physiol. Apr. 1999;276(4 Pt 1):L688-94.

Otterbein et al., Carbon monoxide suppresses arteriosclerotic lesions associated with chronic graft rejection and with balloon injury. Nat Med. Feb. 2003;9(2):183-90. Epub Jan. 21, 2003.

Otterbein et al., Exogenous administration of heme oxygenase-1 by gene transfer provides protection against hyperoxia-induced lung injury. J Clin Invest. Apr. 1999;103(7):1047-54.

Otterbein et al., Heme oxygenase-1: unleashing the protective properties of heme. Trends Immunol. Aug. 2003;24(8):449-55. Review.

Otterbein, Carbon monoxide: innovative anti-inflammatory properties of an age-old gas molecule. Antioxid Redox Signal. Apr. 2002;4(2):309-19. Review.

Ozawa et al., Leydig cell-derived heme oxygenase-1 regulates apoptosis of premeiotic germ cells in response to stress. J Clin Invest. Feb. 2002;109(4):457-67.

Pae et al., Carbon monoxide produced by heme oxygenase-1 suppresses T cell proliferation via inhibition of IL-2 production. J Immunol. Apr. 15, 2004;172(8):4744-51.

Paintner et al., Synthesis and antimicrobial activity of tetrodecamycin partial structures. Bioorg Med Chem. Jul. 3, 2003;11(13):2823-33. Abstract only.

Pankey et al., Clinical relevance of bacteriostatic versus bactericidal mechanisms of action in the treatment of Gram-positive bacterial infections. Clin Infect Dis. Mar. 15, 2004;38(6):864-70. Epub Mar. 1, 2004. Review.

Patel et al., Preparation of (η5-cyclopentadienyl) and (η5-Methylcyclopentadienyl)Fe(CO)2Me cyclodextrin inclusion compounds and their subsequent ligand substitution reactions. Attempts at cyclodextrin mediated enantioselective ligand substitution. J Organometal Chem. 1997;547:103-112.

Peloso et al., Expanding the armamentarium for the spondyloarthropathies. Arthritis Res Ther. 2004;6 Suppl 2:S36-43. Epub Jun. 21, 2004.

Piantadosi, Biological chemistry of carbon monoxide. Antioxid Redox Signal. Apr. 2002;4(2):259-70. Review.

Pneumatikakis et al., Interactions of bis-[μ-chloro-chlorotricarbonylruthenium(II) and poly-[μ-dichloro-dicarbonylruthenium (II)] with nucleotides. Inorg Chimica Acta. 1988;151:243-8.

Quick et al., Pentacarbonylmanganese halides. In Inorganic Syntheses, vol. 19. Duward F. Shriver, Ed. Inorganic Syntheses, Inc. 1979:158-63.

Rattan et al., Mechanism of internal anal sphincter relaxation by CORM-1, authentic CO, and NANC nerve stimulation. Am J Physiol Gastrointest Liver Physiol. Sep. 2004;287(3):G605-11.

Rehder et al., 55Mn NMR characteristics of carbonylmanganese complexes with hetero-substituted dithioformato-, thioformamido- and thioformamide ligands [1]. Inorg Chim Acta. 1983;73:243-7. Abstract only.

Reimann et al., Reactions of metal carbonyls. Part III. Steric and stereochemical limitations of higher substitution of manganese carbonyl bromide. J Chem Soc Dalton Trans. 1973;841-6. Abstract only.

Rodella et al., Carbon monoxide and biliverdin prevent endothelial cell sloughing in rats with type 1 diabetes. Free Radic Biol Med. Jun. 15, 2006;40(12):2198-205. Epub Mar. 20, 2006.

Rutkowska-Zbik et al., Theoretical density functional theory studies on interactions of small biologically active molecules with isolated heme group. J Comput Chem. Mar. 2007;28(4):825-31.

Ryan et al., Renal vascular responses to CORM-A 1 in the mouse. Pharmacol Res. Jul. 2006;54(1):24-9. Epub Mar. 9, 2006.

Ryter et al., Carbon monoxide in biology and medicine. Bioessays. Mar. 2004;26(3):270-80.

Ryter et al., Carbon monoxide: to boldly go where NO has gone before. Sci STKE. Apr. 20, 2004;2004(230):RE6. Review.

Ryter et al., Heme oxygenase/carbon monoxide signaling pathways: regulation and functional significance. Mol Cell Biochem. May-Jun. 2002;234-235(1-2):249-63. Review.

Ryter et al., Heme oxygenase-I/carbon monoxide: from basic science to therapeutic applications. Physiol Rev. Apr. 2006;86(2):583-650. Review.

Sacerdoti et al., Treatment with tin prevents the development of hypertension in spontaneously hypertensive rats. Science. Jan. 20, 1989;243(4889):388-90.

Sacks et al., Comparative bioavailability of elemental iron powders for repair of iron deficiency anemia in rats. Studies of efficacy and toxicity of carbonyl iron. Am J Clin Nutr. Apr. 1978;31(4):566-71.

Salazar-Salinas et al., Molecular biosensor based on a coordinated iron complex. J Chem Phys. Mar. 14, 2009;130(10):105101.

Sammut et al., Carbon monoxide is a major contributor to the regulation of vascular tone in aortas expressing high levels of haeme oxygenase-1. Br J Pharmacol. Dec. 1998;125(7):1437-44.

Sandborn, Strategies for targeting tumour necrosis factor in IBD.Best Pract Res Clin Gastroenterol. Feb. 2003;17(1):105-17. Review.

Sandouka et al., Carbon monoxide-releasing molecules (CO-RMs) modulate respiration in isolated mitochondria. Cell Mol Biol (Noisy-le-grand). Sep. 30, 2005;51(4):425-32.

Sandouka et al., Treatment with CO-RMs during cold storage improves renal function at reperfusion. Kidney Int. Jan. 2006;69(2):239-47.

Santucci et al., Pentoxifylline prevents indomethacin induced acute gastric mucosal damage in rats: role of tumour necrosis factor alpha. Gut. Jul.1994;35(7):909-15.

Sarady et al., Carbon monoxide protection against endotoxic shock involves reciprocal effects on iNOS in the lung and liver. FASEB J. May 2004; 18(7):854-6. Epub Mar. 4, 2004.

Sato et al., Carbon monoxide generated by heme oxygenase-1 suppresses the rejection of mouse-to-rat cardiac transplants. J Immunol. Mar. 15, 2001;166(6):4185-94.

Sawle et al., Carbon monoxide-releasing molecules (CO-RMs) attenuate the inflammatory response elicited by lipopolysaccharide in RAW264.7 murine macrophages. Br J Pharmacol. Jul. 2005;145(6):800-10.

Sawle et al., Homocysteine attenuates endothelial haem oxygenase-1 induction by nitric oxide (NO) and hypoxia. FEBS Lett. Nov. 23, 2001;508(3):403-6.

Schmidt et al., Manganese(I) and rhenium(I) pentacarbonyl(Trifluoromethanesulfatonato) complexes. In Inorganic Syntheses, Ed. Herbert D. Kaesz. vol. 26. Inorganic Syntheses, Inc. 1989:113-17.

Schubert, The action of carbon monoxide on iron and cobalt complexes of cysteine. Carbon Monixide on Iron and Cobalt Cysteine Complexes. 1933;55:4563-70.

Severin et al., Metal complexes of biologically important ligands. LXX. Synthesis, stereochemistry and reactions of ruthenium (II) and osmium (II) complexes with α-amino carboxylates. 1994; 127(4): 615-620. English abstract provided.

Shapiro, Carbonyl-trapping therapeutic strategies. Am J Ther. Sep. 1998;5(5):323-53. Review.

Shiohira et al., Protective effect of carbon monoxide donor compounds in endotoxin-induced acute renal failure. Am J Nephrol. 2007;27(5):441-6. Epub Jul. 12, 2007.

Silver et al., Mossbauer studies on protoprophyrin IX iron (II) solutions containing sulphur ligands and their carbonyl adducts. Inorg Chimica Acta. 1984;9:279-83.

Siow et al., Heme oxygenase-carbon monoxide signalling pathway in atherosclerosis: anti-atherogenic actions of bilirubin and carbon monoxide? Cardiovasc Res. Feb. 1999;41(2):385-94.

Sjöstrand, Endogenous formation of carbon monoxide in man under normal and pathological conditions. Scan J Clin Lab Invest. 1949;1:201-14.

Skattebøl et al., Synthesis of (±)-Lineatin, an aggregation pheromone component of Trypodendron lineatum. Acta Chem Scand B. 1985;39:291-304.

Soares et al., Expression of heme oxygenase-1 can determine cardiac xenograft survival. Nat Med. Sep. 1998;4(9):1073-7.

Song et al., Carbon monoxide inhibits human airway smooth muscle cell proliferation via mitogen-activated protein kinase pathway. Am J Respir Cell Mol Biol. Nov. 2002;27(5):603-10.

Song et al., Carbon monoxide inhibits T lymphocyte proliferation via caspase-dependent pathway. J lmmunol. Jan. 15, 2004;172(2):1220-6.

Spector, Review: Oxidative stress and disease: J Ocul Pharmacol Ther. Apr. 2000;16(2):193-201. Review. Abstract only.

Srisook et al., CO from enhanced HO activity or from CORM-2 inhibits both O2- and NO production and downregulates HO-1 expression in LPS-stimulated macrophages. Biochem Pharmacol. Jan. 12, 2006;71(3):307-18. Epub Dec. 2, 2005.

Srisook et al., Role of NO in enhancing the expression of HO-1 in LPS-stimulated macrophages. Methods Enzymol. 2005;396:368-77.

Staal et al., The syntheses and coordination properties of M(CO)3X(DAB) (M=Mn, Re; X=Cl, Br, I; DAB=1,4-diazabutadiene). J Organometal Chem. May 1, 1979;170( 2):235-45. Abstract only.

Stagni et al., A water-soluble carbon monoxide-releasing molecule (CORM-3) lowers intraocular pressure in rabbits. Br J Ophthalmol. Feb. 2009;93(2):254-7. Epub Oct. 31, 2008.

Stanford et al., Carbon monoxide inhibits endothelin-1 release by human pulmonary artery smooth muscle cells. Eur J Pharmacol. Feb. 23, 2004;486(3):349-52.

Stanford et al., Heme oxygenase is expressed in human pulmonary artery smooth muscle where carbon monoxide has an anti-proliferative role. Eur J Pharmacol. Jul. 25, 2003;473(2-3):135-41.

Stec et al., Heme oxygenase-1 induction does not improve vascular relaxation in angiotensin II hypertensive mice. Am J Hypertens. Feb. 2008;21(2):189-93. Epub Jan. 3, 2008.

Stein et al., Administration of a CO-releasing molecule induces late preconditioning against myocardial infarction. J Mol Cell Cardiol. Jan. 2005;38(1):127-34. Epub Dec. 8, 2004.

Stone et al., Soluble guanylate cyclase from bovine lung: activation with nitric oxide and carbon monoxide and spectral characterization of the ferrous and ferric states. Biochemistry. May 10, 1994;33(18):5636-40.

Stone et al., Synergistic activation of soluble guanylate cyclase by YC-1 and carbon monoxide: implications for the role of cleavage of the iron-histidine bond during activation by nitric oxide. Chem Biol. May 1998;5(5):255-61.

Suematsu et al., Carbon monoxide: an endogenous modulator of sinusoidal tone in the perfused rat liver. J Clin Invest. Nov. 1995;96(5):2431-7.

Sun et al., Attenuation of leukocytes sequestration by carbon monoxide-releasing molecules: liberated carbon monoxide in the liver of thermally injured mice. J Burn Care Res. Jan.-Feb. 2007;28(1):173-81.

Sun et al., CO-releasing molecules (CORM-2)-liberated CO attenuates leukocytes infiltration in the renal tissue of thermally injured mice. Int J Biol Sci. Jun. 16, 2008;4(3):176-83.

Sun et al., Preconditioning of carbon monoxide releasing molecule-derived CO attenuates LPS-induced activation of HUVEC. Int J Biol Sci. Aug. 22, 2008;4(5):270-8.

Sun et al., Role of CO-releasing molecules liberated CO in attenuating leukocytes sequestration and inflammatory responses in the lung of thermally injured mice. J Surg Res. May 1, 2007;139(1):128-35. Epub Feb. 9, 2007.

Suzuki et al., Activated platelets in ulcerative colitis enhance the production of reactive oxygen species by polymorphonuclear leukocytes. Scand J Gastroenterol. Dec. 2001;36(12):1301-6. Abstract only.

Szakács-Schmidt et al., Iron (II) thiolates as reversible carbon monoxide carriers. Inorg Chimica Acta. 1992;198-200:401-5.

Szallasi et al., Dialdehyde sesquiterpenes and other terpenoids as vanilloids. Eur J Pharmacol. Aug. 28, 1998;356(1):81-9. Abstract only.

Tailléet al., Mitochondrial respiratory chain and NAD(P)H oxidase are targets for the antiproliferative effect of carbon monoxide in human airway smooth muscle. J Biol Chem. Jul. 8, 2005;280(27):25350-60. Epub Apr. 29, 2005.

Takács et al., Synthesis and molecular structure of carbonyl derivatives of Iron (II) thiolates containing nitrogen-donor ligands. Inorg Chemica Am. 1989;166:39-46.

Tamaki, Role of second messenger gases in ischemia and reperfusion injury. Low Temp Med. 2001;27(1):1-5. English abstract provided.

Tayem et al., Protection against cisplatin-induced nephrotoxicity by a carbon monoxide-releasing molecule. Am J Physiol Renal Physiol. Apr. 2006;290(4):F789-94. Epub Nov. 15, 2005.

Tenhunen et al., Microsomal heme oxygenase. Characterization of the enzyme. J Biol Chem. Dec. 10, 1969;244(23):6388-94.

Tilg et al., Antitumour necrosis factor therapy in Crohn's disease. Expert Opin Biol Ther. Oct. 2002;2(7):715-21. Review. Abstract only.

Togane et al., Protective roles of endogenous carbon monoxide in neointimal development elicited by arterial injury. Am J Physiol Heart Circ Physiol. Feb. 2000;278(2):H623-32.

Tomita et al., Structure and reaction of bis(L-cysteinato)dicarbonyliron(II). Inorg Nucl Chem Lett. 1968;4:715-8.

Treichel et al., Synthesis and reactivity of bridging thiolato-manganese carbonyl complexes, Et4N[Mn2(μ-SR)3(CO)6]. J Organometall Chem. Sep. 10, 1985;292(3):385-93.

Tsuburai et al., The role of heme oxygenase in pulmonary circulation. Low Temp Med. 2001;27(1):28-35. English abstract provided.

Urban et al., Metal complexes of biologically important ligands, LXXXVII α-amino carboxylate complexes of palladium(II), iridium(III) and ruthenium (II) from chloro-bridged ortho-metallated metal compounds and [(OC)3Ru(Cl)(μ-Cl)]12. J Organomett Chem. 1996;517:191-200.

Urwyler et al., Positive allosteric modulation of native and recombinant gamma-aminobutyric acid(B) receptors by 2,6-Di-tert-butyl-4-(3-hydroxy-2,2-dimethyl-propyl)-phenol (CGP7930) and its aldehyde analog CGP13501. Mol Pharmacol. Nov. 2001;60(5):963-71.

Van Staveren et al., Spectroscopic Properties, Electrochemistry, and Reactivity of Mo0, MoI, and MoII Complexes with the [Mo(bpa)(CO)3] Unit [bpa=bis(2-picolyl)amine] and Their Application for the Labelling of Peptides. Eur J Inorg Chem. 2002;6:1518-29.

Vannacci et al., Evaluation of the effects of a novel carbon monoxide releasing molecule (CORM-3) in an in vitro model of cardiovascular inflammation. 1. Histamine in allergy, inflammation, tissue growth and repair. Inflamm Res. Apr. 2006;55 Suppl 1:S05-6.

Vannacci et al., The effect of a carbon monoxide-releasing molecule on the immunological activation of guinea-pig mast cells and human basophils. Inflamm Res. 2004;53 Suppl 1:S09-10.

Varadi et al., Beneficial effects of carbon monoxide-releasing molecules on post-ischemic myocardial recovery. Life Sci. Apr. 3, 2007;80(17):1619-26. Epub Feb. 2, 2007.

Vera et al., Protective effect of carbon monoxide-releasing compounds in ischemia-induced acute renal failure. J Am Soc Nephrol. Apr. 2005;16(4):950-8. Epub Feb. 23, 2005.

Verma et al., Carbon monoxide: a putative neural messenger. Science. Jan. 15, 1993;259(5093):381-4.

Verona et al., Regioselectivity in the nucleophilic functionalization of xanthene complexes of Mn(CO)3. J Organelle Chem. Nov. 1, 1996;524(1-2)71-80.

Viswanathamurthi et al., Synthesis, characterization and biocidal studies of ruthenium (II) carbonyl complexes containing tetradentate Schiff bases. Transition Metal Chemistry. 1999; 24(6):638-641.

Volti et al., Carbon monoxide signaling in promoting angiogenesis in human microvessel endothelial cells. Antiox Redox Signal. May 2005;7(5-6):704-10.

Vreman et al., Determination of carbon monoxide (CO) in rodent tissue: effect of heme administration and environmental CO exposure. Anal Biochem. Jun. 15, 2005;341(2):280-9. Abstract only.

Vulapalli et al., Cardioselective overexpression of HO-I prevents I/R-induced cardiac dysfunction and apoptosis. Am J Physiol Heart Circ Physiol. Aug. 2002;283(2):H688-94.

Waibel et al., Stable one-step technetium-99m labeling of His-tagged recombinant proteins with a novel Tc(I)-carbonyl complex. Nat Biotechnol. Sep. 1999;17(9):897-901.

Wang et al., A correlation of the visible and Soret spectra of dioxygen- and carbon monoxide-heme complexes and five-coordinate heme complexes with the spectra of oxy-, carboxy-, and deoxyhemoglobins. Biochemistry. Oct. 30, 1979;18(22):4960-77.

Wang et al., Carbon monoxide-induced vasorelaxation and the underlying mechanisms. Br J.Pharmacol. Jul. 1997;121(5):927-34.

Wang et al., Preconditioning limits mitochondrial Ca(2+) during ischemia in rat hearts: role of K(ATP) channels. Am J Physiol Heart Circ Physiol. May 2001;280(5):H2321-8.

Wang et al., The chemical modification of KCa channels by carbon monoxide in vascular smooth muscle cells. J Biol Chem. Mar. 28, 1997;272(13):8222-6.

Weigel et al., Inhibition of DNA replication in *Escherichia coli* by cyanide and carbon monoxide. J Biol Chem. Nov. 10, 1975;250(21):8536-42.

Willis et al., Heme oxygenase: a novel target for the modulation of the inflammatory response. Nat Med. Jan. 1996;2(1):87-90.

Wu et al., Carbon monoxide: endogenous production, physiological functions, and pharmacological applications. Pharmacol Rev. Dec. 2005;57(4):585-630. Review.

Wu et al., Different mechanisms underlying the stimulation of K(Ca) channels by nitric oxide and carbon monoxide. J Clin Invest. Sep. 2002;110(5):691-700.

Xi et al., Carbon monoxide activates KCa channels in newborn arteriole smooth muscle cells by increasing apparent Ca2+ sensitivity of alpha-subunits. Am J Physiol Heart Circ Physiol. Feb. 2004;286(2):H610-8. Epub Oct. 16, 2003.

Xu et al., A facile method for synthesis of (R)-(−)- and (S)-(+)-homocitric acid lactones and related α-hydroxy dicarboxylic acids from d- or l-malic acid. Tetrahedron Lett. May 30, 2005;46(22):3815-18. Abstract only.

Yachie et al., Oxidative stress causes enhanced endothelial cell injury in human heme oxygenase-1 deficiency. J Clin Invest. Jan. 1999;103(1):129-35.

Yan et al., Cytotoxicity of rhenium(I) alkoxo and hydroxo carbonyl complexes in murine and human tumor cells. Pharmazie. Apr. 2000;55(4):307-13.

Yet et al., Cardiac-specific expression of heme oxygenase-1 protects against ischemia and reperfusion injury in transgenic mice. Circ Res. Jul. 20, 2001;89(2):168-73.

Yet et al., Induction of heme oxygenase-1 expression in vascular smooth muscle cells. A link to endotoxic shock. J Biol Chem. Feb. 14, 1997;272(7):4295-301.

Zhang et al., Carbon monoxide inhibition of apoptosis during ischemia-reperfusion lung injury is dependent on the p38 mitogen-activated protein kinase pathway and involves caspase 3. J Biol. Chem. Jan. 10, 2003;278(2):1248-58. Epub Oct. 23, 2002.

Zimmerman et al., Cerebroprotective effects of the CO-releasing molecule CORM-A1 against seizure-induced neonatal vascular injury. Am J Physiol Heart Circ Physiol. Oct. 2007;293:H2501-H2507.

Zuckerbraun et al., Carbon monoxide protects against the development of experimental necrotizing enterocolitis. Am J Physiol Gastrointest Liver Physiol. Sep. 2005;289(3):G607-13. Epub May 12, 2005.

Zuckerbraun et al., Carbon monoxide reverses established pulmonary hypertension. J Exp Med. Sep. 4, 2006;203(9):2109-19. Epub Aug. 14, 2006.

| Compound | Structure | MW | Kinetics of CO Release (min) | Notes |
|---|---|---|---|---|
| CORM-303 | 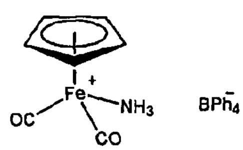 | 513 | > 3000 | Soluble in EtOH |
| CORM-343 | 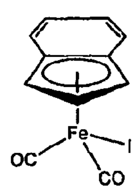 | 440.73 | >3000 | - |
| CORM-360 | 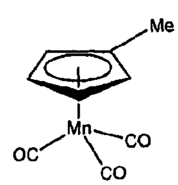 | 218.09 | >3000 | Soluble in EtOH |

| Compound | Chemical Structure | Molecular Weight | Kinetics of CO Release (min) | Cytotoxicity | Anti-inflammatory action | Solubility |
|---|---|---|---|---|---|---|
| CORM-337 | 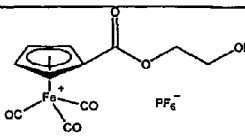 | 438 | 62 ± 6 | V | * | $H_2O$ |
| CORM-351 | 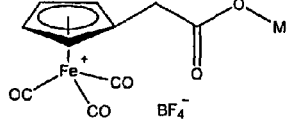 | 363.8 | 225 ± 20 | V | *** | $H_2O$ |
| CORM-352 | 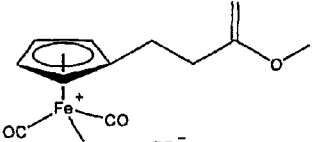 | 377.8 | 285 ± 30 | V | *** | $H_2O$ |
| CORM-357 | 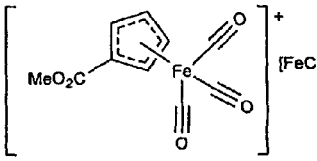 | 461 | 42 ± 5 min | V | ** | $H_2O$ |
| CORM-359 | 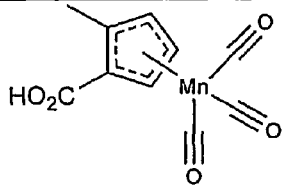 | 262.1 | 3000±300 min | N.D. | N.D. | Ethanol<br><br>Slight water solubility at pH 7.4 |
| CORM-360 | 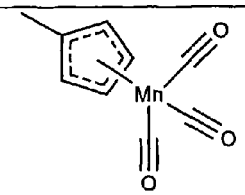 | 218.09 | >3000 min | N.D. | N.D. | Ethanol |
Figure 2 (continued on next sheet)

| Compound | Chemical Structure | Molecular Weight | Kinetics of CO Release (min) | Cytotoxicity | Anti-inflammatory action | Solubility |
|---|---|---|---|---|---|---|
| CORM-361 | 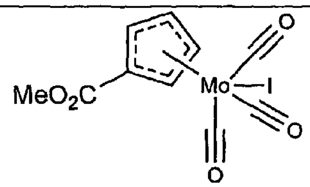 | 430 | 58±6 min | V | *** | Ethanol |
| CORM-380 | 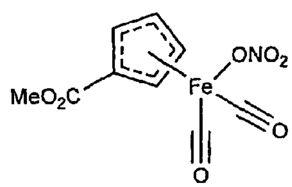 | 297 | 170 | V | ** | $H_2O$ |
| CORM-382 | 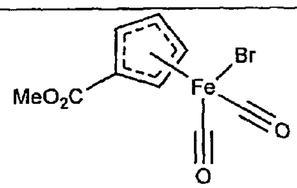 | 314.9 | 38 | V | ** | $H_2O$ |
| CORM-384 | 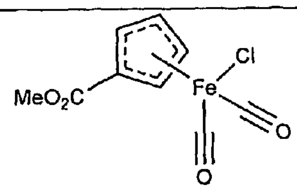 | 270.45 | 63 | V | ** | Ethanol Slight water solubility at pH 7.4 |
| CORM-391 | 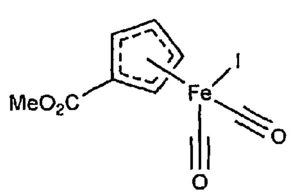 | 361 | 48 | V | *** | Ethanol |

THERAPEUTIC DELIVERY OF CARBON MONOXIDE

This application is the U.S. national phase of International Application No. PCT/GB2007/000198, filed 23 Jan. 2007, which designated the U.S. and claims priority to Great Britain Application No. 0601394.0, filed 24 Jan. 2006, the entire contents of each of which are hereby incorporated by reference.

FIELD OF THE INVENTION

The present invention relates to compounds, pharmaceutical compositions and methods for the therapeutic delivery of carbon monoxide to humans and other mammals. Another use of the compositions and compounds is for organ perfusion. In particular, the invention also relates to methods, compounds and pharmaceutical compositions for carbon monoxide delivery to extracorporeal and isolated organs of humans and other mammals.

BACKGROUND OF THE INVENTION

Carbon monoxide (CO) is, by common definition, a colourless, odourless, tasteless, non-corrosive gas of about the same density as that of air and is the most commonly encountered and pervasive poison in our environment. Depending on the extent and time of exposure, CO is capable of producing a myriad of debilitating and harmful residual effects to the organism (1). The most immediate of these effects, and perhaps the most notorious one, is binding to hemoglobin in the blood stream, which rapidly decreases the oxygen transport capability of the cardiovascular system.

Paradoxically, more than half a century ago it was found that CO is constantly formed in humans in small quantities (2), and that under certain pathophysiological conditions this endogenous production of CO may be considerably increased (3-5). The discovery that hemoglobin, a heme-dependent protein, is required as substrate for the production of CO in vivo (6,7) and the identification of the enzyme heme oxygenase as the crucial pathway for the generation of this gaseous molecule in mammals (8) set the basis for the early investigation of an unexpected and still unrecognized role of CO in the vasculature (9).

A discussion of the background studies carried out in this area are reported in the publication WO 02/092075, which originates from the work of some of the present inventors. The beneficial physiological effects of carbon monoxide (CO) has also been recognized and reported in a number of other publications. As a consequence of these beneficial physiological effects, the literature contains many proposals and studies for providing methods or compounds that have use in delivering therapeutic quantities of carbon monoxide at an appropriate rate to a desired physiological site.

WO 2003/000114 (Beth Israel Deaconess Medical Center) describes a method involving the administration of a carbon monoxide-oxygen ($O_2$) gaseous mixture to an organ, which helps to prevent organ damage for transplant procedures.

Similarly, WO 03/094932 (Yale University) discloses several methods for the generation of carbon monoxide gas and the subsequent administration of the gas to a patient for the treatment of various disorders.

WO 02/078684 (Sangstat Medical Corporation) discloses methods and pharmaceutical compositions for the treatment of vascular disease and for modulating inflammatory and immune processes by using methylene chloride as a carbon monoxide generating compound.

WO 02/092075 and WO 2004/045598, which originate from some of the present inventors, disclose metal carbonyls that are carbon monoxide releasing compounds (CORMs) for the therapeutic delivery of CO to an in vivo or an ex vivo physiological target site. Some of the transition metal carbonyl compounds disclosed in these publications are soluble in water, which is desirable for formulating a pharmaceutical composition. Not all of the compounds disclosed in these publications, such as the cyclopentadienyl iron-carbonyl compound $[CpFe(CO)_3]PF_6$, were found to be soluble in water. This particular compound was soluble in dimethylsulphoxide (DMSO) and produced a precipitate during release of CO. Formation of a precipitate in biological system, whether before or after CO delivery to a physiological target, is undesirable and may be toxic to the organism or result in harmful physiological side effects.

WO 98/029115 (University of British Columbia) discloses transition metal nitrosyl complexes for treating hypertension, angina pectoris and congestive heart disease. The compounds disclosed in this publication require the presence of at least one nitrosyl ligand coordinated to the metal. Cyclopentadienyl metal carbonyl compounds of the form $CpM(CO)_2NO$ and $Cp*M(CO)_2NO$, where M=Cr, Mo, W; Cp is a cyclopentadienyl ligand and Cp* is a pentamethyl cyclopentadienyl ligand, are exemplified in this document.

US 2004/0116448 (Schmalz, H.-G. et al) discloses the use of iron carbonyl complexes for the treatment of diseases caused by highly proliferating cells, such as tumour cells. The active compounds contain a butadiene moiety, which is bound to an iron tricarbonyl unit in an $\eta^4$ manner. The butadiene moiety may form part of a five membered cyclic ring. Generation of a cyclopentadienyl group and its subsequent coordination to the transition metal in an $\eta^5$ manner is not disclosed.

WO 03/066067 (Haas, W. et al) proposes as a class of compounds "CO containing organometallic complexes" for use in the treatment and/or prevention of diseases. Generic examples of organometallic transition metal-carbonyl compounds that fall within this class are described. Amongst these examples, the generic formulae for the following organometallic compounds are given:

$[(\eta^5\text{-CpR})M(CO)_3]$ for M=Mn, Re;

$[(\eta^5\text{-CpR})M(CO)_2]$ for M=Co, Rh;

$[(\eta^5\text{-CpR})M(CO)_2X]$ for M=Fe, Ru;

$[(\eta^5\text{-CpR})M(CO)_3X]$ for M=Cr, Mo, W;

$[\eta^5\text{-IndM(CO)}_2X]$ for M=Fe, Ru;

$[\eta^5\text{-IndM(CO)}_3X]$ for M=Cr, Mo, W;

$[(\eta^5\text{-CpR})M(CO)_2L]^+Y^-$ for M=Fe, Ru; and $[(\eta^5\text{-CpR})M(CO)_3L]^+Y^-$ for Cr, Mo, W;

where Cp is a cyclopentadienyl ligand, Ind is an indenyl ligand, R is H, alkyl, acyl, formyl, carboxylate, sugar, peptide or halide, X is alkyl, aryl, halide, OR', SR', $O_2CR'$, $S_2CNR'_2$, $S_2P(OR')_2$, L is CO, olefin, alkyne, or a monodentate 2 electron donor of O, S, N or P, and Y is a halide or a weakly coordinating anion.

Attaching a carboxylic derivative to the cyclopentadienyl ring is also proposed in order to modify biological compatibility and solubility. The following Mn complex is given as an example of a possible modified compound:

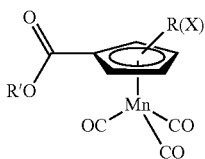

where R(X) is H, alkyl, aryl, formyl, acyl, carboxylate or fused C6 aromatic ring (indenyl ligand), and R' is H, alkyl, peptide or sugar.

WO 03/066067 (Haas, W. et al) does not describe the synthesis of any of the above compounds and does not contain any literature reference to a procedure for their preparation. It is further noted that there is no evidence in this document, such as biological test data, in support of the use of these compounds for the delivery of CO in vivo or ex vivo.

STATEMENT OF THE INVENTION

As exemplified by the data presented below, the present inventors have found that pharmaceutical compositions and compounds according to the invention can be used to deliver CO to a physiological target and result in the formation of a by-product or products that are soluble in an aqueous physiological fluid after CO release.

Accordingly, a first aspect of the present invention provides a pharmaceutical composition for delivery of CO, comprising as an active ingredient a compound represented by formula (I) or formula (II) below:

$$[CpM(CO)_xL_p]^{+z}(Y^{-q})_{z/q} \quad (I)$$

wherein:—
M is a transition metal selected from group 6, 7, 8 or 9 of the periodic table;
Y is a counteranion;
q is the charge of Y and is selected from 1, 2 or 3;
x is 2, 3 or 4;
z is 0 or 1, and x, z and p satisfy the equation $$13-g=2x-z+p$$

where g is the group number of M in the periodic table, and where
  p is 0 or 1 when g is 6; or
  p is 0 when g is 7, 8 or 9;
L is a ligand selected from H, halide, $C_{1-7}$ alkyl, $C_{6-14}$ aryl, $C_{1-7}$ alkoxy, $C_{6-14}$ aryloxy, $C_{1-7}$ alkylthio, $C_{5-10}$ arylthio, acyloxy (—OC(=O)$R^5$), amido (—C(=O)$NR^5R^6$), acylamido (—$NR^5$C(=O)$R^6$), aminocarbonyloxy(—OC(=O)$NR^5R^6$) and aminothiocarbonylthiol (—SC(=S)$NR^5R^6$);

$$[CpM'(CO)_2L']^{+z}(Y^{-q})_{z/q} \quad (II)$$

wherein
M' is Fe or Ru;
X is a counteranion;
q is the charge of Y and is selected from 1, 2 or 3;
L' is a ligand selected from either
  a first group consisting of H, halide, —$NO_2$, —ONO, —$ONO_2$, —OH, —SCN, —NCS, —OCN, —NCO, $C_{1-7}$ alkyl, $C_{6-14}$ aryl, $C_{1-7}$ alkoxy, $C_{6-14}$ aryloxy, $C_{1-7}$ alkylthio, $C_{5-10}$ arylthio, acyloxy(—OC(=O)$R^7$), amido (—C(=O)$NR^7R^8$), acylamido (—$NR^7$C(=O)$R^8$), aminocarbonyloxy (—OC(=O)$NR^7R^8$), (SC(=O)$R^7$), —SC(S)$R^7$, —SC(S)O$R^7$, —SC(O)$NR^7R^8$, —SC(O)O$R^7$, aminothiocarbonylthiol (—SC(=S)$NR^7R^8$), —OC(=S)$R^7$, —N(C(=O)$R^7$)$_2$, and —C(O)(O$R^7$); —O—P$R^7R^8R^9$, —O—P$R^7_{3-n}$(O$R^8$)$_n$ where n=1, 2 or 3, —O—P$R^7_{(3-n)}$(N$R^8/R^9$)$_n$ where n=1, 2 or 3; or
  a second group consisting of O$R^7R^8$, O=C$R^7R^8$, O=C(N$R^7R^8$)$R^9$, O=C(O$R^7$)$R^8$, O=S$R^7R^8$, O=S(O)$R^7R^8$, S$R^7R^8$, S(O)$R^7R^8$, S=C$R^7R^8$, S=C(N$R^7R^8$)$R^9$, S=C(O$R^7$)$R^8$, N$R^7R^8R^9$, NC$R^7$, N* where N is an aromatic nitrogen atom in an aromatic ring represented by N*, P$R^7R^8R^9$, P$R^7_{(3-n)}$(O$R^8$)$_n$ where n=1, 2 or 3, P$R^7_{(3-n)}$(N$R^8R^9$)$_n$ where n=1, 2 or 3, O=P$R^7R^8R^9$, O=P$R^7_{(3-n)}$(O$R^8$)$_n$ where n=1, 2 or 3, O=P$R^7_{(3-n)}$(N$R^8R^9$)$_n$ where n=1, 2 or 3;
$R^7$, $R^8$ and $R^9$ are independently selected from H, optionally substituted $C_{1-7}$ alkyl and optionally substituted $C_{6-20}$ aryl, with the proviso that any two of $R^7$, $R^8$ and $R^9$ which are both attached to the same O, N or S atom may, taken together with that atom, form an optionally substituted heterocyclic ring having 5, 6 or 7 ring atoms;
z=0 when L' is from said first group and z=1 when L' is from said second group;
and wherein in formula (I) and formula (II):—
Cp is selected from:

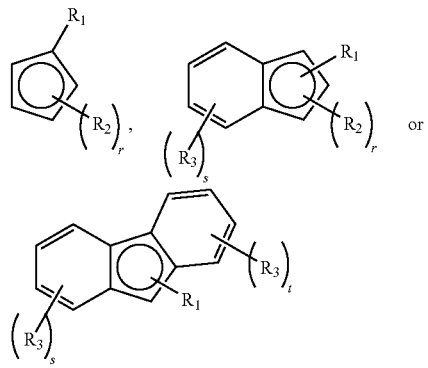

where r, s and t are each independently selected from 1, 2, 3 or 4; and
$R_1$ is either:

$$-[Alk]_n-O-C(O)-Q_1, -[Alk]_n-C(O)-O-Q_1, -[Alk]_n-NR_4-C(O)-Q_1 \text{ or } -[Alk]_n-C(O)-NQ_1Q_2,$$

n is 0 or 1;
Alk is a $C_{1-28}$ alkylene group;
$Q_1$ and $Q_2$ are each independently selected from H, optionally substituted $C_{1-22}$ alkyl and an optionally substituted $C_{6-25}$ aryl group;
each $R_2$ is independently selected from $R_1$, H, $C_{1-22}$ alkyl, $C_{6-25}$ aryl, $C_{1-7}$ alkoxy, $C_{5-10}$ aryloxy, halide, formyl, $C_{1-7}$ alkylacyl and $C_{6-20}$ arylacyl;
$R_4$ is selected from H, $C_{1-22}$ alkyl and $C_{6-25}$ aryl;
each $R_3$ is independently selected from H, hydroxy, nitro, cyano, halide, sulfhydryl, $C_{1-22}$ alkyl, $C_{6-25}$ aryl, $C_{1-7}$ alkoxy, $C_{5-10}$ aryloxy, formyl, alkylacyl, $C_{6-20}$ arylacyl, alkylthio, $C_{5-10}$ arylthio, carboxylic acid (—C(=O)OH), ester (—C(=O)O$R^5$), acyloxy(—OC(=O)$R^5$), amido (—C(=O)$NR^5R^6$), acylamido (—$NR^5$C(=O)$R^6$) and amino (—$NR^5R^6$); and
$R^5$ and $R^6$ are independently selected from H, $C_{1-7}$ alkyl and $C_{6-20}$ aryl.

The transition metal carbonyl compounds in pharmaceutical compositions according to the first aspect of the invention comprise carbonyl ligands and a cyclopentadienyl, indenyl or fluorenyl ligand covalently bonded to the transition metal centre in an $\eta^5$ manner. These organometallic compounds satisfy what is commonly known in the art as the 18 electron rule.

Before taking into account any electron contribution from the coordination of a ligand, the transition metal in pharmaceutical compositions or compounds of the present invention already has some electrons in its valence shell. The number of electrons already present is given by the group number of the transition metal in the periodic table. In this specification the groups of the periodic table are numbered according to the IUPAC system from 1 to 18. The cyclopentadienyl, indenyl or fluorenyl ligand bonds to the transition metal by its π orbitals in an $\eta^5$ manner, such that it contributes five electrons to the valence shell of the metal. Each carbonyl ligand formally donates two electrons to the valence shell of the transition metal. A ligand L, as written in formula (I) above, may also be coordinated to the metal. L represents an anionic ligand, such as $I^-$, and formally contributes one electron to the valence shell of the metal. The total number of carbonyl ligands and L ligands that coordinate to the metal is determined by the 18 electron rule.

If the transition metal is selected from a group in the periodic table such that it has an even number of electrons i.e. g=6 or 8, and there are no L ligands (one electron anionic ligands) coordinated to the metal, then to satisfy the 18 electron rule the organometallic complex will have a formal charge of +1 because it must lose an electron. Alternatively, when g is 6, one of the carbonyl ligands (a two electron donor) may be replaced with an L ligand (a one electron donor). In such compounds the organometallic complex is not charged.

The oxidation state of the transition metal in compounds of the present invention from group 6 or 8 of the periodic table is +2. Whereas, the oxidation state of the transition metal from group 7 or 9 of the periodic table in compounds according to the present invention is +1.

The same principles apply for the compounds of formula (II). The oxidation state of Fe or Ru is +2.

Attaching substituents to the cyclopentadienyl, indenyl or fluorenyl ring of a transition metal complex may subtly alter the electronic properties of the molecule. Thus the inclusion of particular types of substituent may allow modulation of the rate of CO release to a physiological target from the carbon monoxide releasing molecule (CORM). The chemical nature of the substituent may additionally increase the solubility of the CORM in aqueous physiological fluid.

WO 03/066067 (Haas, W. et al) suggests that several classes of organometallic compound may be used as CORMs. However, WO 03/066067 does not contain an enabling disclosure for many of these classes of organometallic compound. Furthermore, this document provides no data in support of these molecules as being CORMs, but rather speculates, what would have been known to the skilled worker in the art, that these classes of compounds are potential CORM candidates. The present inventors have found that under the conditions of the tests that they employed, several classes of organometallic compounds that are proposed for use as CORMs in WO 03/066067 do not actually release CO to a physiological target.

The present inventors surprisingly found that compounds according to the present invention do not precipitate in an aqueous physiological fluid after release of CO. It is believed that the presence of the substituent ($R_1$) on the cyclopentadienyl ring increases the solubility and/or stabilises the resulting CORM by-product thereby preventing decomposition to an insoluble species. Formation of an insoluble by-product or products within a biological system may cause undesirable physiological effects.

If the transition metal is selected from group 6 or 8 of the periodic table, then in order to satisfy the 18 electron rule, the organometallic compound according to the present invention has a transition metal in the +2 oxidation state. When p=0, such that no L ligands are present, the compound will be charged i.e. z=1 in formula (I) above. The resulting ionic compound will consist of an organometallic cation, and a counter anion represented by Y in formula (I) above.

It is predicted that the CORM by-products of compounds of formula (I) having a transition metal in the +2 oxidation state (i.e. g=6 or 8) and compounds of formula (II) will have greater solubility in an aqueous physiological fluid than the CORM by-products of compounds with a metal in the +1 oxidation state. Preferably, the oxidation state of the transition metal is +2. In particular, solubility in an aqueous physiological fluid is likely to be greater for compounds where the transition metal is in the +2 oxidation state and has a formal charge of +1 (z=1).

If the organometallic complex has a formal charge, then it will be associated with a counteranion. The counteranion, represented in formula (I) and (II) above by Y, may have a negative charge greater than or equal to 1, as represented by "q". According to the present invention, the charge of the organometallic cation cannot exceed +1 (unless for example a ligand or constituent contains a quaternary nitrogen). If the charge of counteranion exceeds −1, then to balance the charge of the overall compound, there must be more than one organometallic cation. For example, if the counteranion is sulphate ($SO_4^{2-}$) and the cation is $[CpFe(CO)_3]^{+1}$, then the formula of the compound may be written as $[CpFe(CO)_3]_2(SO_4)$ and is represented in formula (I) above in terms of a single organometallic cation as $[CpFe(CO)_3](SO_4)_{1/2}$.

It is preferred that the counteranion is selected from a halide (e.g. $F^-$, $Cl^-$, $Br^-$ or $I^-$); sulphonate (e.g. $TsO^-$, $MsO^-$, $TfO^-$, $BsO^-$); borate (e.g. $BF_4^-$, $BPh_4^-$); hexafluorophosphate ($PF_6^-$); a perhalate (e.g. $ClO_4^-$); sulphate ($SO_4^{2-}$); phosphate ($PO_4^{3-}$); a carboxylate anion of an organic acid, such as the anions of the acids 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric; or of an amino acid, such as glycinate etc., or any other pharmaceutically acceptable anion known to those skilled in the art, such as those described in S Berge et al, Journal of Pharmaceutical Science (1977), 66 (1) 1-19; P Gould, International Journal of Pharmaceutics (1986), 33, 201-217. Most preferred are counteranions that are carboxylate anions of organic carboxylic acids or amino acids.

When the transition metal is from group 6, the metal may be coordinated to four carbonyl ligands so that the resulting organometallic compound is cationic having a charge of +1. Alternatively, the group 6 transition metal may be neutral if it is coordinated to three carbonyl groups and an anionic ligand represented by L. If the transition metal is from group 6, then it is preferred that p is 1 and x is 3 so that the transition metal is coordinated to an L ligand. L is selected from H, halide, $C_{1-7}$ alkyl, $C_{6-14}$ aryl, alkoxy, $C_{6-14}$ aryloxy, $C_{1-7}$ alkylthio, $C_{5-10}$ arylthio, acyloxy($-OC(=O)R^5$), amido ($-C(=O)NR^5R^6$), acylamido ($-NR^5C(=O)R^6$), aminocarbonyloxy ($-OC(=O)NR^5R^6$) and aminothiocarbonylthiol ($-SC(=S)NR^5R^6$). In particular, L is selected from H, halide, alkyl, $C_{6-14}$ aryl, $C_{1-7}$ alkoxy and $C_{6-14}$ aryloxy. More preferably, L is H, halide, $C_{1-7}$ alkyl, $C_{6-14}$ aryl. Most preferred is when L is Cl, Br or I.

Some of the transition metals in groups 6 to 9 may cause or be associated with undesirable physiological side effects.

Preferably, the transition metal M is selected from Fe, Ru, Mn and Mo. Most preferred are compounds where M is one of Fe and Mo. Fe is particularly preferred.

In the compound of formula (II), M' is preferably Fe. The L' is selected from the first group of anionic (one electron donor) ligands or from the second group of neutral (two electron donor) ligands.

Among the ligands of the first group, preferred are H, halide, —$NO_2$, —ONO—, —$ONO_2$, —OH, $C_{1-7}$ alkyl, $C_{6-14}$ aryl, $C_{1-7}$ alkoxy and $C_{6-14}$ aryloxy. More preferably L' of the first group is halide, —$NO_2$, —ONO, —$ONO_2$, —OH, $C_{1-7}$ alkyl or $C_{6-14}$ aryl. Most preferred are Cl, Br, I and —$ONO_2$.

The ligands of the second group coordinate through O, S, N or P. In each item of the list of ligands of the second group, the coordinating atom is placed first. Particular examples of the ligands of the second group are $OH_2$ (water)
$OHR^7$, e.g. $C_2H_5OH^-$
$OR^7R^8$, e.g. tetrahydrofuran
$O=CR^7R^8$, e.g. $(CH_3)_2CO$
$O=C(NR^7R^8)R^9$, e.g. $CH_3CON(CH_3)_2$
$O=C(OR^7)R^8$, e.g. $CH_3COOCH_3$
$O=SR^7R^8$, e.g. DMSO
$O=S(O)R^7R^8$, e.g. $(CH_3)_2SO_2$
$SH_2$
$HSR^7$
$SR^7R^8$
$S(O)R^7R^8$, e.g. DMSO coordinating through S
$S=CR^7R^8$, e.g. $(CH_3)_2CS$
$S=C(NR^7R^8)R^9$, e.g. $CH_3C(S)N(CH_3)_2$
$S=C(OR^7)R^8$, e.g. $CH_3C(S)OCH_3$
$NH_3$
$NH_2R^7$
$NHR^7R^8$
$NR^7R^8R^9$
a ligand of the type N* coordinating through an $sp^2$N in an aromatic ring, e.g. pyridine, histidine or ademine.

In pharmaceutical compositions according to the present invention, the compounds represented by formula (I) or formula (II) contain an ester or amide group in the substituent $R^1$ which is attached to the cyclopentadienyl, indenyl or fluorenyl ring. It is shown herein that the selected compounds release CO to a biological system and that the starting compound is soluble in an aqueous physiological fluid. The inventors have surprisingly found that coupling the cyclopentadienyl, indenyl or fluorenyl ring to an ester or amide group confers additional solubility and/or stability to the by-product or by-products formed after CO release.

The $R^I$ substituent attached to the Cp group comprises an ester group, represented by -[Alk]$_n$-O—C(O)-$Q_1$ or -[Alk]$_n$-C(O)—O-$Q_1$, or an amide group, as represented by -[Alk]$_n$-C(O)-$Q_1$ or -[Alk]$_n$-C(O)—$NQ_1Q_2$. It is preferred that $R^1$ is an ester group -[Alk]$_n$-O—C(O)-$Q_1$ or -[Alk]$_n$-C(O)—O-$Q_1$.

In an embodiment of the present aspect of the invention, $R^1$ is a -[Alk]$_n$-O—C(O)-$Q_1$ unit, where the ester unit is attached by its "alkoxy" oxygen atom to the Cp group either directly or by an alkylene spacer unit, which is represented by "Alk". In this embodiment, it is preferred for an alkylene spacer unit to be present i.e. n=1. It is believed that solubility of the by-product or products formed after CO release are more soluble and/or stable when the ester group is attached by its oxygen to an alkylene spacer and then to the Cp group. Furthermore, compounds having an ester group attached to the Cp ring by an alkylene spacer group are synthetically more accessible.

In this particular embodiment, the alkylene spacer unit "Alk" is a $C_{1-28}$ alkylene group. It is preferred that "Alk" is a linear or branched saturated $C_{1-10}$ alkylene group, which excludes the subclasses alkenylene, alkynylene and cycloalkylene. In particular, it is preferable that "Alk" is an unbranched or linear saturated $C_{1-6}$ alkylene group. More preferably, "Alk" is an unbranched and unsubstituted $C_{2-5}$ alkylene group.

In an alternative embodiment, $R^1$ is -[Alk]$_n$-C(O)—O-$Q_1$, where the ester group is attached by an optional alkylene spacer unit by its carbonyl carbon atom to the Cp group. When the ester group is attached to the Cp group in this manner, the optional alkylene spacer has less of an effect on the solubility of the by-product or products from the CORM. However, it is believed that in this and the previous embodiment, the length of the alkylene spacer may have a modulating effect in the CO releasing properties of the CORM molecule and has a stabilising effect on the CORM by-product or products. When n is 1, "Alk" is preferably linear or branched saturated $C_{1-10}$ alkylene group, which excludes the subclasses alkenylene, alkynylene and cycloalkylene. It is further preferred that "Alk" is a linear or unbranched saturated $C_{1-6}$ alkylene group or more preferably a $C_{1-5}$ alkylene group. Most preferred is when "Alk" is a linear saturated $C_{1-4}$ alkylene group.

When Cp represents the ligand

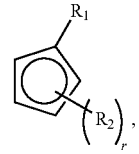

the number of $R_2$ substituents is given by r and can be 1, 2, 3 or 4. When r is 1, 2 or 3 there are several possible stereoisomers where the position of the $R_2$ substituent(s) varies relative to the position of $R_1$. The structural representation given above encompasses all of these possible stereoisomers, which are shown in the table below.

| r | Stereoisomers |
|---|---|
| 1 | ![structure with R1 and R2]<br>![structure with R1 and R2] |

| r | Stereoisomers |
|---|---|
| 2 | 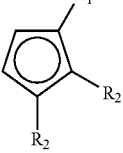 |
| 3 | 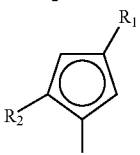 |
| 4 | 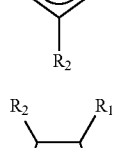 |

Substituents, represented by $R_3$, may also be directly attached to the aryl ring or rings of the indenyl or fluorenyl ligand. For indenyl ligands, the label $(R_3)$, in the structure below, as used herein, includes indenyl ligands having one, two, three or four $R^3$ substituents attached to the phenyl or aryl ring.

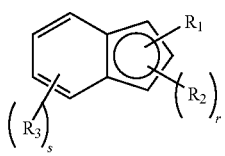

The structural representation above encompasses all possible isomers for each possible number of $R_3$ aryl ring substituents. For example, if there are two $R_3$ substituents, then the structural formula above includes the 4,5, 4,6, 4,7, 5,6, 5,7 and 6,7 isomers.

Similarly, the labels $(R_3)_s$ and $(R_3)_t$ each represent fluorenyl ligands having one, two, three or four $R_3$ substituents attached to each of the respective aryl rings. The structural representation below also encompasses all possible $R_3$ aryl ring substituent isomers, as described above for the indenyl ligand.

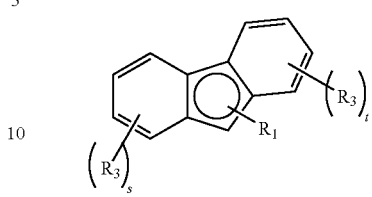

Each $R_3$ aryl ring substituted may be independently selected from H, hydroxy, nitro, cyano, halide, sulfhydryl, $C_{1-22}$ alkyl, $C_{6-25}$ aryl, $C_{1-7}$ alkoxy, $C_{5-10}$ aryloxy, formyl, $C_{1-7}$ alkylacyl, $C_{6-20}$ arylacyl, $C_{1-7}$ alkylthio, $C_{5-10}$ arylthio, carboxylic acid (—C(=O)OH), ester (—C(=O)OR$^5$), acyloxy (—OC(=O)R$^5$), amido (—C(=O)NR$^5$R$^6$), acylamido (—NR$^5$C(=O)R$^6$) and amino (—NR$^5$R$^6$), where R$^5$ and R$^6$ are independently selected from H, $C_{1-7}$ alkyl and $C_{6-20}$ aryl. Preferably, $R_3$ is selected from H, hydroxy, nitro, cyano, halide, $C_{1-22}$ alkyl, $C_{6-25}$ aryl, $C_{1-7}$ alkoxy, $C_{5-10}$ aryloxy and amino (—NR$^5$R$^6$). More preferably, $R_3$ is H, halide, $C_{1-22}$ alkyl and $C_{6-25}$ aryl. In particular, $R_3$ is H, methyl, ethyl or phenyl. Most particularly, $R_3$ is H.

The number of $R_3$ aryl ring substituents may vary, depending on the nature of the Cp group, from 1 to 8. It is preferred that there are one, two or three $R_3$ aryl ring substituents. More preferred are indenyl or fluorenyl ligands where there are a total of one or two $R_3$ aryl ring substituents.

When two or more substituents ($R_1$, $R_2$ or $R_3$) are attached to the Cp group (the cyclopentadienyl, indenyl and fluorenyl ligand) of a transition metal carbonyl complex, the resulting organometallic carbonyl compound may have a chiral centre. Unless otherwise specified, a reference to a particular compound includes all such isomeric forms, including (wholly or partially) racemic and other mixtures thereof. Methods for the preparation (e.g. asymmetric synthesis) and separation (e.g., fractional crystallisation and chromatographic means) of such isomeric forms are either known in the art or are readily obtained by adapting the methods taught herein, or known methods, in a known manner.

In another embodiment of the first aspect of the invention, it is preferred that Cp in the compound represented by formula (I) or formula (II) is

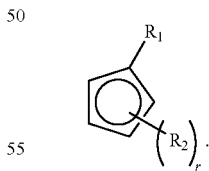

There have been many studies in the field of organometallic chemistry on the effect that substituents attached to the cyclopentadienyl ring have on the metal complex. As a result, the scientific literature in this field contains many synthetic methodologies for preparing substituted cyclopentadienyl rings. It is preferred that the cyclopentadienyl ring contains one or four $R_2$ substituents i.e. r=1 or 4. More preferably, r=1. If the cyclopentadienyl ring contains a single $R_2$ substituent when r=1, then $R_2$ will be in the 2- or 3-position relative to $R_1$ on the cyclopentadienyl ring. Often cyclopentadienyl compounds having two substituents attached to the ring (i.e. 1, 2 or 1, 3 substituents) have to be separated by chromatography.

In yet another embodiment of the invention, it is preferred that the Cp ligand in formula (I) or formula (II) above is an indenyl ligand. The indenyl ligand contains a cyclopentadienyl ring fused at one side to a phenyl ring. The uncoordinated indenyl anion is a 10 electron aromatic system, compared to the 6 electron aromatic ring of the cyclopentadienide anion. This difference in the electronic properties of the indenyl ligand may subtly alter the electronic properties of the organometallic complex upon coordination which, in turn, may effect the rate of CO release. In addition to this electronic effect, the additional arene ring may shield or provide a steric barrier. It is possible that this could increase the kinetic stability of CORMs containing an indenyl ligand. It is also well known in the art, that the bonding mode or hapticity of the indenyl ligands may change during a reaction, such as a ring slippage where the hapticity of the ligand can change from $\eta^5$ to $\eta^3$. The change in bonding mode may aid the rate of reaction of the CORM in a physiological environment and thereby alter the rate of CO release.

In embodiments where the Cp group is an indenyl ligand, the $R_1$ substituent is attached to the five-membered cyclopentadienyl-type ring of the indenyl ligand. $R_1$ may be attached to the 1, 2 or 3 positions of the indenyl ligand, as indicated in the diagram.

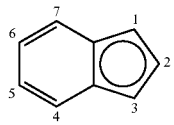

The position of $R_1$ on the indenyl ring may favour particular synthetic methods used for the preparation of the ligand. For example, $R_1$ may be introduced into the 2-position of the indenyl ligand by using a starting material such as indanone. A maximum of two $R_2$ substituents can be attached to the cyclopentadienyl moiety of the indenyl system.
Preferably, r is 1.

In the embodiments where Cp is a cyclopentadienyl or an indenyl ligand, the five membered ring or cyclopentadienyl moiety may contain more than one substituent ($R_1$ and $R_2$). The second substituent may be incorporated onto the ligand to further aid the solubility of the CORM, the CORM by-product or may further assist in the modulation of the rate of CO release by the CORM compound.

The second substituent $R_2$ may be independently selected from any of the groups for $R_1$. If $R_2$ is selected from any of the groups for $R_1$, $R_2$ is not limited so that it is identical to the group selected for $R_1$. However, it is preferable that if $R_2$ is to be independently selected from a group for $R_1$, that $R_2$ and $R_1$ are identical. For example, when $R_1$ is —$CH_2$—O—C(O)-Me then $R_2$ is —$CH_2$—O—C(O)-Me. If $R_2$ is not selected from the groups defined for $R_1$, it is preferred that $R_2$ is selected from H, $C_{1-22}$ alkyl and $C_{9-25}$ aryl. Most preferably $R_2$ is H or methyl, more particularly H.

In addition to increasing the solubility, the inventors believe that the presence of the ester or amide group as a substituent on the Cp group may enhance or accelerate the rate of CO release in some physiological environments. Some of these environments enzymes, such as esterases, which are capable of hydrolysing the ester or amide group in compounds and pharmaceutical compositions of the present invention. Hydrolysis of the ester or amide group may result in the formation of a nucleophilic species, such as a carboxylate moiety, that is able to "attack" the metal centre and thereby trigger CO release from the CORM compound.

The inventors also believe that the length of the $R_1$ Cp-substituent has a stabilising effect on the CORM by-product or products. The inventors propose that the carbonyl-oxygen atom of the ester or amide group may coordinate and thereby stabilise the transition metal centre after CO release. In principle, coordination may be to the metal centre of another, nearby molecule (intermolecular coordination) or to the metal of that same molecule (intramolecular coordination). In particular, when the ester or amide group is attached to the Cp unit by an alkylene spacer group, the carbonyl-oxygen atom may be able to "reach round" and coordinate to the metal in an intramolecular manner so that the overall ligand forms a chelate.

An alternative to the stabilising effect that may be provided by intramolecular coordination of the carbonyl oxygen atom, the $Q_1$ and/or $Q_2$ group that forms part of the $R_1$ substituent may contain an atom or group that may coordinate to the metal centre. This atom or group, may be a ligating atom or group and may preferentially coordinate to the metal instead of the carbonyl oxygen atom. Ligating atoms or groups are atoms or chemical functional groups that can coordinate as a ligand to a metal. Typically, the ligating atom or group has a lone pair of electrons or has a negative charge, which allows it to coordinate to the metal.

Preferential coordination of the ligating atom or group of $Q_1$ and/or $Q_2$ may occur when the overall length of $R_1$ is too short for the carbonyl oxygen atom to reach the metal centre to coordinate in a intramolecular manner, or if the ligating part of the $Q_1$ and/or $Q_2$ group forms a stronger bond with the metal than the carbonyl oxygen atom.

In pharmaceutical compositions and compounds according to the present invention $Q_1$ and $Q_2$ are each independently selected from H, optionally substituted $C_{1-22}$ alkyl and an optionally substituted $C_{6-25}$ aryl group.

In one embodiment of the present invention, $Q_1$ and/or $Q_2$ does not contain a ligating atom or group and is selected from H, optionally substituted $C_{1-22}$ alkyl and optionally substituted $C_{6-25}$ aryl group, where the optional substituents are selected from $C_{1-10}$ alkyl and $C_{6-14}$ aryl. Preferably, $Q_1$ and/or $Q_2$ is selected from H, optionally substituted $C_{1-10}$ alkyl and optionally substituted $C_{6-14}$ aryl. More preferably, $Q_1$ and/or $Q_2$ is selected from H, $C_{1-6}$ alkyl, $C_{6-10}$ aryl and the benzyl group. Most preferred is when $Q_1$ and/or $Q_2$ is selected from H, $C_{1-5}$ alkyl, benzyl and phenyl.

In another embodiment, $Q_1$ and/or $Q_2$ contains a group that can act as a ligating atom or group, or contains a polar functional group, which may further increase the solubility of the compound. $Q_1$ and $Q_2$ are each independently selected from H, optionally substituted $C_{1-22}$ alkyl and optionally substituted $C_{6-25}$ aryl group, where the optional substituents are selected from those provided in the list below. Preferably, $Q_1$ and/or $Q_2$ is selected from H, optionally substituted $C_{1-10}$ alkyl and optionally substituted $C_{6-14}$ aryl. More preferably, $Q_1$ and/or $Q_2$ is selected from H, $C_{1-5}$ alkyl and $C_{6-10}$ aryl.

In this embodiment, where $Q_1$ and/or $Q_2$ is a group that may be optionally substituted, it is preferred that the optional substituent is selected from α-amino acid group, hydroxy, ether, ester, oxo, acyloxy, amino, amido and acylamido. More preferably, the optional substituent is selected from α-amino acid group, hydroxy, ester and $C_{1-7}$ alkylamino. Most preferred is when the optional substituent is hydroxy.

In the embodiment where $R^1$ is a -[Alk]$_n$-O—C(O)-Q and n=1, it is preferred that $Q_1$ is selected from H, substituted $C_{1-22}$ alkyl and optionally substituted $C_{6-25}$ aryl group, where the preferred substituents are the same as those listed for the previous embodiment. More preferably, $Q_1$ is selected from H, substituted $C_{6-22}$ alkyl and optionally substituted $C_{6-14}$ aryl group. More particularly, $Q_1$ is selected from H and optionally substituted $C_{6-10}$ aryl group.

In yet another embodiment, $R^1$ is -[Alk]$_n$-C(O)—O-Q$_1$ and n is 0 so that the carbonyl group is directly attached to the ring of the Cp group. In this embodiment, $Q_1$ is selected from H, optionally substituted $C_{1-22}$ alkyl and an optionally substituted $C_{6-25}$ aryl group. Preferably, $Q_1$ is H, $C_{1-22}$ alkyl and $C_{6-25}$ aryl. More preferably, $Q_1$ is H or $C_{1-7}$ alkyl. Most preferred is when $Q_1$ is H or methyl.

An embodiment of the present aspect of the invention, as described above, may be combined with another embodiment of the first aspect of the invention.

Organometallic compounds having a nitrosyl ligand coordinated directly to the transition metal centre, and pharmaceutical compositions containing such compounds, are excluded from the present invention.

The pharmaceutical compositions of the present invention typically comprise a pharmaceutically acceptable excipient, carrier, buffer, stabiliser or other materials well known to those skilled in the art.

Such materials should be non-toxic and should not interfere unduly with the efficacy of the active ingredient. The precise nature of the carrier or other material may depend on the route of administration, e.g. oral, intravenous, transdermal, subcutaneous, nasal, inhalatory, intramuscular, intraperitoneal, or suppository routes.

Pharmaceutical compositions for oral administration may be in tablet, capsule, powder or liquid form. A tablet may include a solid carrier such as gelatin or an adjuvant or a slow-release polymer. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. Pharmaceutically acceptable amounts of other solvents may also be included, in particular where they are required for dissolving the particular metal carbonyl compound contained in the composition.

For intravenous, cutaneous or subcutaneous injection, or injection at the site of affliction, the active ingredient will typically be in the form of a parenterally acceptable solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required. Delivery systems for needle-free injection are also known, and compositions for use with such systems may be prepared accordingly.

Administration is preferably in a prophylactically effective amount or a therapeutically effective amount (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners.

Examples of the techniques and protocols mentioned above can be found in Remington's Pharmaceutical Sciences, 16th edition, Osol, A. (ed), 1980.

When formulating pharmaceutical compositions according to the present invention, the toxicity of the active ingredient and/or the solvent must be considered.

The balance between medical benefit and toxicity should be taken into account. The dosages and formulations of the compositions will typically be determined so that the medical benefit provided outweighs any risks due to the toxicity of the constituents.

A second aspect of the present invention is compound represented by the formula (III)

wherein
Y is a counteranion;
q is the charge of Y and is selected from 1, 2 or 3;
Cp is selected from:

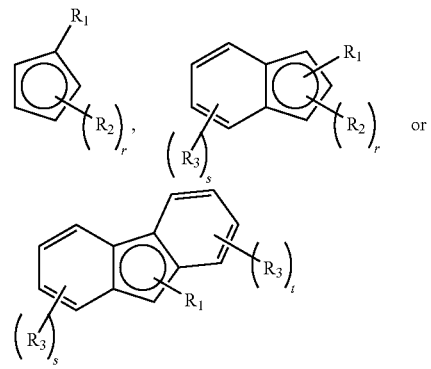

where r, s and t are each independently selected from 1, 2, 3 or 4; and
$R_1$ is either:

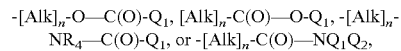

n is 0 or 1;
Alk is a $C_{1-26}$ alkylene group;
$Q_1$ and $Q_2$ are each independently selected from H, optionally substituted $C_{1-22}$ alkyl and an optionally substituted $C_{6-25}$ aryl group;
each $R_2$ is independently selected from $R_1$, H, $C_{1-22}$ alkyl, $C_{6-25}$ aryl, $C_{1-7}$ alkoxy, $C_{5-10}$ aryloxy, halide, formyl, $C_{1-7}$ alkylacyl and $C_{6-20}$ arylacyl;
$R_4$ is selected from H, $C_{1-22}$ alkyl and $C_{6-25}$ aryl;
each $R_3$ is independently selected from H, hydroxy, nitro, cyano, halide, sulfhydryl, $C_{1-22}$ alkyl, $C_{6-25}$ aryl, $C_{1-7}$ alkoxy, $C_{5-10}$ aryloxy, formyl, $C_{1-7}$ alkylacyl, $C_{6-20}$ arylacyl, $C_{1-7}$ alkylthio, $C_{5-10}$ arylthio, carboxylic acid (—C(=O)OH), ester (—C(=O)OR$^5$), aryloxy(—OC(=O)R$^5$), amido (—C(=O)NR$^5$R$^6$), acylamido (—NR$^5$C(=O)R$^6$) and amino (—NR$^5$R$^6$); and
$R^5$ and $R^6$ are independently selected from H, $C_{1-7}$ alkyl and $C_{6-20}$ aryl.

In the second aspect of the invention, it is preferred that when the Cp group is indenyl or fluorenyl, the aryl ring substituent $R_3$ is selected from H, hydroxy, nitro, cyano, halide, $C_{1-22}$ alkyl, $C_{6-25}$ aryl, $C_{1-7}$ alkoxy, $C_{5-10}$ aryloxy and amino (—NR$^5$R$^6$). More preferably, $R_3$ is H, halide, $C_{1-22}$ alkyl and $C_{6-25}$ aryl. In particular, $R_3$ is H, methyl, ethyl or phenyl. Most particularly, $R_3$ is H.

When $R_3$ is not H, it is preferred that there are 1, 2 or 3 $R_3$ aryl ring substituents. More preferred are indenyl or fluorenyl ligands where there are a total of 1 or 2 $R_3$ aryl ring substituents.

Compounds according to the second aspect of the invention, preferably have a Cp group that is the cyclopentadienyl ligand or indenyl ligand

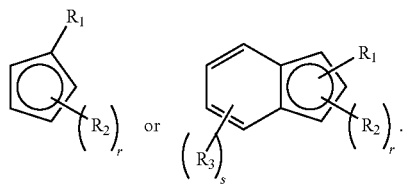

More preferably, Cp is the cyclopentadienyl ligand shown above. When Cp is the cyclopentadienyl ligand, the ring preferably contains one or four $R_2$ substituents i.e. r=1 or 4, but more preferably r=1.

The second substituent $R_2$ may be independently selected from any of the groups for $R_1$. It is preferable that if $R_2$ is to be independently selected from a group for $R_1$, that $R_2$ and $R_1$ are identical. If $R_2$ is not selected from the groups defined for $R_1$, then it is preferred that $R_2$ is selected from H, $C_{1-22}$ alkyl and $C_{9-25}$ aryl. Most preferably $R_2$ is H or methyl, more particularly H.

In the present aspect of the invention, $R_1$ is preferably -[Alk]$_n$-O—C(O)-$Q_1$ or -[Alk]$_n$-C(O)—O-$Q_1$. Most preferred is when $R_1$ is -[Alk]$_n$-C(O)—O-$Q_1$.

In one embodiment, $R_1$ is -[Alk]$_n$-O—C(O)-$Q_1$ or -[Alk]$_n$-C(O)—O-$Q_1$, more particularly -[Alk]$_n$-C(O)—O-$Q_1$, and n is 0. In this embodiment, $Q_1$ is preferably selected from H, optionally substituted $C_{1-10}$ alkyl and optionally substituted $C_{6-14}$ aryl. In particular, the optional substituent is selected from $C_{1-10}$ alkyl, $C_{6-14}$ aryl, α-amino acid group, hydroxy, ether, ester, oxo, acyloxy, amino, amido and acylamido. More preferably, the optional substituent is selected from α-amino acid group, hydroxy, ester and $C_{1-7}$ alkylamino. Most preferred is when the optional substituent is hydroxy. The most preferred groups for $Q_1$ in this embodiment are $C_{1-10}$ alkyl and $C_{1-10}$ hydroxyalkyl, particularly methyl, ethyl and hydroxyethyl.

In an alternative embodiment of the second aspect, $R_1$ is -[Alk]$_n$-O—C(O)-$Q_1$ or -[Alk]$_n$-C(O)—O-$Q_1$, more particularly -[Alk]$_n$-C(O)—O-$Q_1$, and n is 1. "Alk" is preferably linear or branched saturated $C_{1-10}$ alkylene group, which excludes the subclasses alkenylene, alkynylene and cycloalkylene. It is further preferred that "Alk" is a linear or unbranched saturated $C_{1-6}$ alkylene group or more preferably a $C_{1-5}$ alkylene group. Most preferred is when "Alk" is a linear saturated $C_{1-4}$ alkylene group, more particularly $C_1$ or $C_2$ alkylene. Preferably, $Q_1$ is selected from H, optionally substituted $C_{1-10}$ alkyl and optionally substituted $C_{6-14}$ aryl. More preferably, $Q_1$ is selected from H, $C_{1-5}$ alkyl, $C_{6-10}$ aryl and the benzyl group. Most preferred is when $Q_1$ is selected from H, $C_{1-5}$ alkyl, benzyl and phenyl. Preferred optional substituents are as listed for the previous embodiment. The counteranion Y may be selected from the list of counteranions given above for the first aspect of the invention. Preferably, the counteranion Y has a charge q of −1, such as when Y is a halide, borate or is hexafluorophosphate. Most preferred is when Y is Cl$^-$, BF$_4^-$ or PF$_6^-$.

A third aspect of the invention is a method of introducing CO to a mammal comprising the step of administering a pharmaceutical composition or compound according to the present invention. The method of introducing CO is for treatment of hypertension, such as acute, pulmonary and chronic hypertension, radiation damage, endotoxic shock, inflammation, inflammatory-related diseases such as asthma and rheumatoid arthritis, hyperoxia-induced injury, apoptosis, cancer, transplant rejection, arteriosclerosis, post-ischemic organ damage, myocardial infarction, angina, haemorrhagic shock, sepsis, penile erectile dysfunction and adult respiratory distress syndrome.

The data presented herein is an extension of the work presented in WO 02/092075 and WO 2004/045598. Based on the work presented in these documents, it is preferred that the method of the present invention is for the treatment of hypertension, such as acute, pulmonary and chronic hypertension, endotoxic shock, inflammation, inflammatory-related diseases such as asthma and rheumatoid arthritis, hyperoxia-induced injury, cancer, transplant rejection, arteriosclerosis, post-ischemic organ damage, myocardial infarction, angina, haemorrhagic shock, sepsis and adult respiratory distress syndrome. More preferred is a method for the treatment of hypertension, endotoxic shock, inflammation, inflammatory-related diseases such as asthma and rheumatoid arthritis, post-ischemic organ damage, myocardial infarction and sepsis. Even more preferred is a method for the treatment of hypertension, post-ischemic organ damage and myocardial infarction.

The present aspect of the invention also includes a method of treatment of an extracorporeal or isolated organ, comprising contacting the organ with a pharmaceutical composition according to the present invention. The metal carbonyl makes available carbon monoxide (CO) to limit post-ischemic damage. The organ treated in the method of the invention is an organ which is isolated from the blood supply. The organ may be extracorporeal e.g. a donated organ outside of the donor's body, or it may be isolated in the sense that it is in a patient's body and isolated from the blood supply for surgical purposes.

The organ may be, for example, a circulatory organ, respiratory organ, urinary organ, digestive organ, reproductive organ, neurological organ, muscle or skin flap or an artificial organ containing viable cells.

Most preferably, the organ is a heart, lung, kidney or liver. The contacting with the compositions containing metal carbonyl can be achieved by any method that exposes the organ to the composition e.g. bathing or pumping. Preferably, an isolated organ which is attached to the body, i.e. a bypassed organ, is perfused with the composition. An organ which is extracorporeal is preferably bathed in the composition.

In WO 02/092075 and WO 2004/045598 some of the present inventors demonstrated that metal carbonyl compounds can be used in the treatment of particular diseases. Thus, by extension, the present invention also provides the use of a metal carbonyl compound as herein described in the manufacture of a medicament for delivering CO to a physiological target, particularly a mammal, to provide a physiological effect, e.g. for stimulating neurotransmission or vasodilation, or for treatment of any of hypertension, such as acute, pulmonary and chronic hypertension, radiation damage, endotoxic shock, inflammation, inflammatory-related diseases such as asthma and rheumatoid arthritis, hyperoxia-induced injury, apoptosis, cancer, transplant rejection, arteriosclerosis, post-ischemic organ damage, myocardial infarction, angina, haemorrhagic shock, sepsis, penile erectile dysfunction and adult respiratory distress syndrome. Such medicaments may be adapted for administration by an oral, intravenous, subcutaneous, nasal, inhalatory, intramuscular, intraperitoneal or suppository route. Preferably the present invention excludes delivery of a metal carbonyl or a decomposition product thereof to an organism through the skin or mucosa.

More preferably, the use of a metal carbonyl compound as described herein is in the manufacture of a medicament for the treatment of hypertension, such as acute, pulmonary and chronic hypertension, endotoxic shock, inflammation, inflammatory-related diseases such as asthma and rheumatoid arthritis, hyperoxia-induced injury, cancer, transplant rejection, arteriosclerosis, post-ischemic organ damage, myocardial infarction, angina, haemorrhagic shock, sepsis and adult respiratory distress syndrome. More preferred is a medicament for the treatment of hypertension, endotoxic shock, inflammation, inflammatory-related diseases such as asthma and rheumatoid arthritis, post-ischemic organ damage, myocardial infarction and sepsis. Even more preferred is a medicament for the treatment of hypertension, post-ischemic organ damage and myocardial infarction.

The invention further provides use of the metal carbonyls here described in treatment, e.g. by perfusion, of a viable mammalian organ extracorporeally, e.g. during storage and/or transport of an organ for transplant surgery. For this purpose, the metal carbonyl is in dissolved form, preferably in an aqueous solution. The viable organ may be any tissue containing living cells, such as a heart, a kidney, a liver, a skin or muscle flap, etc.

A fourth aspect of the invention is a kit for producing a pharmaceutical solution. The kit comprises a compound as described herein and a pharmaceutically acceptable solvent. Some of the compounds described herein release CO upon dissolution. Storage of such CORMS in solution is thus impractical because the CORM will decompose or deactivate and will be unable to deliver CO to the physiological target. It is preferred that such CORMs are prepared using the kit according to the present invention immediately before administration to a human or mammalian patient.

DEFINITIONS

The term "physiological fluid", as used herein, pertains to fluid suitable for pharmaceutical administration to a physiological system, such as water or a saline solution, or to a fluid already present in a physiological system, such as blood plasma or blood.

The term "counteranion", as used herein, pertains to an atom or group having a formal negative charge that is present to balance the charge of the organometallic cation. The term encompasses anions which are known to be suitable within the art as counteranions for organometallic complexes, such as $BF_4^-$, $PF_6^-$ etc. The counteranion may be the conjugate base of a strong acid. Examples of counteranions that are a conjugate base of a strong acid are $Cl^-$, $SO_4^{2-}$, $ClO_4^-$ etc. The counteranion may also be the conjugation base of a weak or organic acid, such as $CH_3COO^-$ etc. The counteranion may have a charge greater than one, such as in $SO_4^{2-}$, It is preferred that the counteranion does not act as a nucleophile toward the cationic organometallic complex.

The acronyms OTs, OBs, OMs and OTf represent the anions tosylate, brosylate, mesylate and triflate as is commonly known within the art.
Alkylene Alkylene: The term "alkylene", as used herein, pertains to a bidentate moiety obtained by removing two hydrogen atoms, either both from the same carbon atom, or one from each of two different carbon atoms, of a hydrocarbon compound having from 1 to 20 carbon atoms (unless otherwise specified), which may be aliphatic or alicyclic, and which may be saturated, partially unsaturated, or fully unsaturated. Thus, the term "alkylene" includes the sub-classes alkenylene, alkynylene, cycloalkylene, etc., discussed below.

In this context, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkylene," as used herein, pertains to an alkylene group having from 1 to 4 carbon atoms. Examples of groups of alkylene groups include $C_{1-4}$alkylene ("lower alkylene"), $C_{1-7}$alkylene, and $C_{1-20}$alkylene.

Examples of linear saturated $C_{1-7}$alkylene groups include, but are not limited to, —$(CH_2)_n$— where n is an integer from 1 to 7, for example, —$CH_2$—(methylene), —$CH_2CH_2$—(ethylene), —$CH_2CH_2CH_2$—(propylene), and —$CH_2CH_2CH_2CH_2$—(butylene).

Examples of branched saturated $C_{1-7}$alkylene groups include, but are not limited to, —$CH(CH_3)$—, —$CH(CH_3)CH_2$—, —$CH(CH_3)CH_2CH_2$—, —$CH(CH_3)CH_2CH_2CH_2$—, —$CH_2CH(CH_3)CH_2$—, —$CH_2CH(CH_3)CH_2CH_2$—, —$CH(CH_2CH_3)$—, —$CH(CH_2CH_3)CH_2$—, and —$CH_2CH(CH_2CH_3)CH_2$—.

Examples of linear partially unsaturated $C_{1-7}$alkylene groups include, but is not limited to, —CH═CH—(vinylene), —CH═CH—$CH_2$—, —$CH_2$—CH═CH—, —CH═CH—$CH_2$—$CH_2$—, —CH═CH—$CH_2$—$CH_2$—, —$CH_2$—CH═CH—$CH_2$—, —CH═CH—CH═CH—, —CH═CH—CH═CH—$CH_2$—, —CH═CH—$CH_2$—CH═CH—, and —CH═CH—$CH_2$—$CH_2$—CH═CH—.

Examples of branched partially unsaturated $C_{1-7}$alkylene groups include, but is not limited to, —$C(CH_3)$═CH—, —$C(CH_3)$═CH—$CH_2$—, and —CH═CH—$CH(CH_3)$—.

Examples of alicyclic saturated $C_{1-7}$alkylene groups include, but are not limited to, cyclopentylene (e.g. cyclopent-1,3-ylene), and cyclohexylene (e.g. cyclohex-1,4-ylene).

Examples of alicyclic partially unsaturated $C_{1-7}$alkylene groups include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond. Compounds and/or groups may be partially unsaturated or fully unsaturated.

Alkyl: The term "alkyl," as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated or unsaturated (e.g., partially unsaturated, fully unsaturated). Thus, the term "alkyl" includes the sub-classes alkenyl, alkynyl, cycloalkyl, cycloalkenyl, cylcoalkynyl, etc., as discussed below. Preferably, the term "alkyl" includes only the sub-class cycloalkyl. More preferably, "alkyl" does not include the sub-classes alkenyl, alkynyl, cycloalkyl, cycloalkyenyl and cylcoalkynyl.

In the context of alkyl groups, the prefixes (e.g. $C_{1-4}$, $C_{1-7}$, $C_{1-20}$, $C_{2-7}$, $C_{3-7}$ etc.) denote the number of carbon atoms, or range of number of carbon atoms. For example, the term "$C_{1-4}$alkyl," as used herein, pertains to an alkyl group having from 1 to 4 carbon atoms. Examples of groups of alkyl groups include $C_{1-4}$alkyl, $C_{1-7}$alkyl, and $C_{3-20}$alkyl. Note that the first prefix may vary according to other limitations; for example, for unsaturated alkyl groups, the first prefix must be at least 2; for cyclic and branched alkyl groups, the first prefix must be at least 3; etc.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), and heptyl ($C_7$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_6$).

Alkenyl: The term "alkenyl," as used herein, pertains to an alkyl group having one or more carbon-carbon double bonds. Examples of groups of alkenyl groups include $C_{2-4}$alkenyl, $C_{2-7}$alkenyl, $C_{2-20}$alkenyl.

Examples of (unsubstituted) unsaturated alkenyl groups include, but are not limited to, ethenyl(vinyl, —CH=$CH_2$), 1-propenyl(—CH=CH—$CH_3$), 2-propenyl(allyl, —CH—CH=$CH_2$), isopropenyl(1-methylvinyl, —C($CH_3$)=$CH_2$), butenyl($C_4$), pentenyl ($C_5$), and hexenyl($C_6$).

Alkynyl: The term "alkynyl," as used herein, pertains to an alkyl group having one or more carbon-carbon triple bonds. Examples of groups of alkynyl groups include $C_{2-4}$alkynyl, $C_{2-7}$alkynyl, $C_{2-20}$alkynyl.

Examples of (unsubstituted) unsaturated alkynyl groups include, but are not limited to, ethynyl(ethinyl, —C≡CH) and 2-propynyl(propargyl, —$CH_2$—C≡CH).

Cycloalkyl: The term "cycloalkyl," as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g., partially unsaturated, fully unsaturated), which moiety has from 3 to 20 carbon atoms (unless otherwise specified), including from 3 to 20 ring atoms. Thus, the term "cycloalkyl" includes the sub-classes cycloalkyenyl and cycloalkynyl. Preferably, each ring has from 3 to 7 ring atoms. Examples of groups of cycloalkyl groups include $C_{3-20}$cycloalkyl, $C_{3-15}$cycloalkyl, $C_{3-10}$cycloalkyl, $C_{3-7}$cycloalkyl.

Examples of cycloalkyl groups include, but are not limited to, those derived from:

saturated monocyclic hydrocarbon compounds: cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$);

unsaturated monocyclic hydrocarbon compounds: cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$);

saturated polycyclic hydrocarbon compounds: thujane ($C_{10}$), carane ($C_{10}$), pinane ($C_{10}$), bornane ($C_{10}$), norcarane ($C_7$), norpinane ($C_7$), norbornane ($C_7$);

unsaturated polycyclic hydrocarbon compounds: camphene ($C_{10}$), limonene ($C_{10}$), pinene ($C_{10}$).

Aryl: The term "aryl," as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g., $C_{3-20}$, $C_{5-7}$, $C_{5-6}$, etc.) denote the number of ring atoms, or range of number of ring atoms, whether carbon atoms or heteroatoms. For example, the term "$C_{5-6}$aryl," as used herein, pertains to an aryl group having 5 or 6 ring atoms. Examples of groups of aryl groups include $C_{3-20}$aryl, $C_{5-20}$aryl, $C_{5-15}$, $C_{5-12}$aryl and $C_{5-10}$aryl.

The ring atoms may be all carbon atoms, as in "carboaryl groups." Examples of carboaryl groups include $C_{3-20}$carboaryl, $C_{5-20}$carboaryl, $C_{5-15}$carboaryl, $C_{5-12}$carboaryl and $C_{5-10}$carboaryl.

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Optional Substituents

The phrase "optionally substituted," as used herein, pertains to a parent group which may be unsubstituted or which may be substituted.

Unless otherwise specified, the term "substituted," as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known. Definitions for substituents are provided in the list below.

In formula (I) above, the groups $Q_1$, $Q_2$ and/or $R_3$ may refer to a chemical moiety that may itself be optionally substituted with one or more groups selected from the additional substituents listed below.

α-Amino Acid Group: The term "α-amino acid group," as used herein, pertains to a group having the structure shown below:

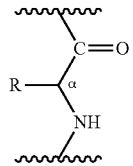

which corresponds to an α-amino acid of the following formula $RC^αH(NH_2)COOH$. The α-amino acid group may covalently bond as an optional substituent by its amino nitrogen atom, by its carbonyl carbon atom, both as shown in the diagram above, or by its carboxylate oxygen atom. The remaining bond to the carbonyl carbon atom or to the amino nitrogen atom may bond to another α-amino acid group to form a peptide chain. Preferably, the peptide chain does not exceed five α-amino acid groups in length.

If the α-amino acid group is bonded by the carbonyl carbon atom or carboxylate oxygen atom, then group attached to the amino nitrogen atom may be selected from H, $C_{1-22}$ alkyl, $C_{6-14}$ aryl, $C_{1-22}$ alkoxycarbonyl and $C_{6-14}$ aryloxycarbonyl. Alternatively, if the α-amino acid group is bonded by the amino nitrogen atom, then the group bonded to the carbonyl carbon atom may be selected from H, $C_{1-22}$ alkyl, $C_{6-14}$ aryl, $C_{1-22}$ alkoxy and $C_{6-14}$ aryloxy.

Examples of α-amino acids include both natural amino acids and non-natural amino acids. The natural amino acids include: those with nonpolar (hydrophobic) R groups: alanine, Ala, A; isoleucine, Ile, I; leucine, Leu, L; methionine, Met, M; phenylalanine, Phe, F; proline, Pro, P; tryptophan, Trp, W; and valine, Val, V; those with polar but uncharged R groups: asparagine, Asn, N; cysteine, Cys, C; glutamine, Gln, Q; glycine, Gly, G; serine, Ser, S; threonine, Thr, T; and tyrosine, Tyr, Y; those with (potentially) positively charged R groups: arginine, Arg, R; histidine, His, H; and lysine, Lys, K; and those with (potentially) negatively charged R groups: aspartic acid, Asp, D; glutamic acid, Glu, E.

An example of an α-amino acid group, but is not limited to, is —O—CO—CHMeNHC(O)OC(CH$_3$)$_3$, which is a Boc protected alanine α-amino acid group.

Halo: —F, —Cl, —Br, and —I.
Hydroxy: —OH.
Nitro: —NO$_2$.
Cyano (nitrile, carbonitrile): —CN.
Ether: —OR, wherein R is an ether substituent, for example, a C$_{1-7}$alkyl group (also referred to as a C$_{1-7}$alkoxy group, discussed below), or a C$_{5-20}$ aryl group (also referred to as a C$_{5-20}$ aryloxy group), preferably a C$_{1-7}$ alkyl group.
Alkoxy: —OR, wherein R is an alkyl group, for example, a C$_{1-7}$ alkyl group. Examples of C$_{1-7}$alkoxy groups include, but are not limited to, —OMe(methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).
Oxo (keto, -one): =O.
Thione (thioketone): =S.
Imino(imine): =NR$^5$, wherein R$^5$ is an imino substituent, for example, hydrogen, C$_{1-7}$ alkyl group, or a C$_{5-20}$ aryl group, preferably hydrogen or a C$_{1-7}$ alkyl group. Examples of ester groups include, but are not limited to, =NH, =NMe, =NEt, and =NPh.
Formyl (carbaldehyde, carboxaldehyde): —C(=O)H.
Acyl (keto): —C(=O)R$^5$, wherein R$^5$ is an acyl substituent, for example, a C$_{1-7}$ alkyl group (also referred to as C$_{1-7}$ alkylacyl or C$_{1-7}$ alkanoyl), or a C$_{5-20}$ aryl group (also referred to as C$_{5-20}$ arylacyl), preferably a C$_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).
Carboxy (carboxylic acid): —C(=O)OH.
Thiocarboxy (thiocarboxylic acid): —C(=S)SH.
Thiolocarboxy (thiolocarboxylic acid): —C(=O)SH.
Thionocarboxy (thionocarboxylic acid): —C(=S)OH.
Imidic acid: —C(=NH)OH.
Hydroxamic acid: —C(=NOH)OH.
Ester (carboxylate, carboxylic acid ester, oxycarbonyl): —C(=O)OR$^5$, wherein R$^5$ is an ester substituent, for example, a C$_{1-7}$ alkyl group, or a C$_{5-20}$ aryl group, preferably a C$_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.
Acyloxy (reverse ester): —OC(=O)R$^5$, wherein R$^5$ is an acyloxy substituent, for example, a C$_{1-7}$ alkyl group, or a C$_{5-20}$ aryl group, preferably a C$_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O) Ph, and —OC(=O)CH$_2$Ph.
Oxycarboyloxy: —OC(=O)OR$^5$, wherein R$^5$ is an ester substituent, for example, a C$_{1-7}$ alkyl group, or a C$_{5-20}$ aryl group, preferably a C$_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O) OPh.
Amino: —NR$^5$R$^6$, wherein R$^5$ and R$^6$ are independently amino substituents, for example, hydrogen, a C$_{1-7}$ alkyl group (also referred to as C$_{1-7}$ alkylamino or di-C$_{1-7}$alkylamino), or a C$_{5-20}$ aryl group, preferably H or a C$_{1-7}$ alkyl group, or, in the case of a "cyclic" amino group, R$^5$ and R$^6$, taken together with the nitrogen atom to which they are attached, form a heterocyclic ring having from 4 to 8 ring atoms. Amino groups may be primary (—NH$_2$), secondary (—NHR$^5$), or tertiary (—NHR$^5$R$^6$), and in cationic form, may be quaternary (—$^+$NR$^5$R$^6$R$^7$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.
Amido (carbamoyl, carbamyl, aminocarbonyl, carboxamide): —C(=O)NR$^5$R$^6$, wherein R$^5$ and R$^6$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O) NHCH$_2$CH$_3$, and —C(=O)N(CH$_2$CH$_3$)$_2$, as well as amido groups in which R$^5$ and R$^6$, together with the nitrogen atom to which they are attached, form a heterocyclic structure as in, for example, piperidinocarbonyl, morpholinocarbonyl, thiomorpholinocarbonyl, and piperazinocarbonyl.
Thioamido (thiocarbamyl): —C(=S)NR$^5$R$^6$, wherein R$^5$ and R$^6$ are independently amino substituents, as defined for amino groups.
Acylamido (acylamino): —NR$^5$C(=O)R$^6$, wherein R$^5$ is an amide substituent, for example, hydrogen, a C$_{1-7}$ alkyl group, or a C$_{5-20}$ aryl group, preferably hydrogen or a C$_{1-7}$ alkyl group, and R$^6$ is an acyl substituent, for example, a C$_{1-7}$ alkyl group, a C$_{3-20}$ heterocyclyl group, or a C$_{5-20}$ aryl group, preferably hydrogen or a C$_{1-7}$ alkyl group. Examples of acylamide groups include, but are not limited to, —NHC(=O) CH$_3$, —NHC(=O)CH$_2$CH$_3$, and —NHC(=O)Ph. R$^5$ and R$^6$ may together form a cyclic structure, as in, for example, succinimidyl, maleimidyl, and phthalimidyl.

succinimidyl    maleimidyl    phthalimidyl

Aminocarbonyloxy: —OC(=O)NR$^5$R$^6$, wherein R$^5$ and R$^6$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.
Aminothiocarbonylthiol: —SC(=S)NR$^5$R$^6$, wherein R$^5$ and R$^6$ are independently amino substituents, as defined for amino groups. Examples of aminocarbonyloxy groups include, but are not limited to, —SC(=S)NH$_2$, —SC(=S)NHMe, and —SC(=S)NMe$_2$.
Ureido: —N(R$^5$)CONR$^6$R$^7$ wherein R$^6$ and R$^7$ are independently amino substituents, as defined for amino groups, and R$^5$ is a ureido substituent, for example, hydrogen, a alkyl group, or a C$_{5-20}$ aryl group, preferably hydrogen or a C$_{1-7}$ alkyl group.
Guanidino: —NH—C(=NH)NH$_2$.
Imino: =NR, wherein R is an imino substituent, for example, hydrogen, a C$_{1-7}$alkyl group, or a C$_{5-20}$ aryl group, preferably H or a $C_{1-7}$ alkyl group. Examples of imino groups include, but are not limited to, =NH, =NMe, and =NEt.

Amidine (amidino): —C(=NR)NR$_2$, wherein each R is an amidine substituent, for example, hydrogen, a $C_{1-7}$ alkyl group, or a $C_{5-20}$ aryl group, preferably H or a $C_{1-7}$ alkyl group.

Sulfhydryl (thiol, mercapto): —SH.

Thioether (sulfide): —SR, wherein R is a thioether substituent, for example, a $C_{1-7}$ alkyl group (also referred to as a $C_{1-7}$ alkylthio group), or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Sulfine (sulfinyl, sulfoxide): —S(=O)R, wherein R is a sulfine substituent, for example, a alkyl group, or a $C_{5-20}$ aryl group, preferably a $C_{1-7}$ alkyl group.

Sulfone (sulfonyl): —S(=O)$_2$R, wherein R is a sulfone substituent, for example, a $C_{1-7}$ alkyl group, or a $C_{5-20}$ aryl group, preferably a $C_{1-7}$ alkyl group. Examples of sulfone groups include, but are not limited to, —S(=O)$_2$CH$_3$ (methanesulfonyl, mesyl), —S(=O)$_2$CF$_3$(triflyl), —S(=O)$_2$CH$_2$CH$_3$ (esyl), —S(=O)$_2$C$_4$F$_9$(nonaflyl), —S(=O)$_2$CH$_2$CF$_3$(tresyl), —S(=O)$_2$CH$_2$CH$_2$NH$_2$(tauryl), —S(=O)$_2$Ph (phenylsulfonyl, besyl), 4-methylphenylsulfonyl(tosyl), 4-bromophenylsulfonyl(brosyl) and 4-nitrophenyl(nosyl).

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substituent, for example, a $C_{1-7}$ alkyl group, or a $C_{5-20}$ aryl group, preferably a $C_{1-7}$ alkyl group.

Sulfonate (sulfonic acid ester): —S(=O)$_2$OR, wherein R is a sulfonate substituent, for example, a $C_{1-7}$ alkyl group, or a $C_{5-20}$ aryl group, preferably a $C_{1-7}$ alkyl group.

Sulfinyloxy: —OS(=O)R, wherein R is a sulfinyloxy substituent, for example, a $C_{1-7}$ alkyl group, or a $C_{5-20}$ aryl group, preferably a $C_{1-7}$ alkyl group.

Sulfonyloxy: —OS(=O)$_2$R, wherein R is a sulfonyloxy substituent, for example, a $C_{1-7}$ alkyl group, or a $C_{5-20}$ aryl group, preferably a $C_{1-7}$ alkyl group.

Sulfate: —OS(=O)$_2$OR; wherein R is a sulfate substituent, for example, a $C_{1-7}$alkyl group, or a $C_{5-20}$ aryl group, preferably a $C_{1-7}$ alkyl group.

Sulfamyl (sulfamoyl; sulfinic acid amide; sulfinamide): —S(=O)NR$^5$R$^6$, wherein R$^5$ and R$^6$ are independently amino substituents, as defined for amino groups.

Sulfonamido (sulfinamoyl; sulfonic acid amide; sulfonamide): —S(=O)$_2$NR$^5$R$^6$, wherein R$^5$ and R$^6$ are independently amino substituents, as defined for amino groups.

Sulfamino: —NR$^5$S(=O)$_2$OH, wherein R$^5$ is an amino substituent, as defined for amino groups.

Sulfonamino: —NR$^5$S(=O)$_2$R, wherein R$^5$ is an amino substituent, as defined for amino groups, and R is a sulfonamino substituent, for example, a $C_{1-7}$ alkyl group, or a $C_{5-20}$ aryl group, preferably a $C_{1-7}$alkyl group.

Sulfinamino: —NR$^5$S(=O)R, wherein R$^5$ is an amino substituent, as defined for amino groups, and R is a sulfinamino substituent, for example, a $C_{1-7}$ alkyl group, or a $C_{5-20}$ aryl group, preferably a $C_{1-7}$ alkyl group.

Phospho: —P(=O)$_2$.

Phosphinyl (phosphine oxide): —P(=O)R$_2$, wherein R is a phosphinyl substituent, for example, a $C_{1-7}$ alkyl group, or a $C_{5-20}$ aryl group.

Phosphonic acid (phosphono): —P(=O)(OH)$_2$.

Phosphonate (phosphono ester): —P(=O)(OR)$_2$, where R is a phosphonate substituent, for example, —H, a $C_{1-7}$ alkyl group, or a $C_{5-20}$ aryl group.

Phosphoric acid (phosphonooxy): —OP(=O)(OH)$_2$.

Phosphate (phosphonooxy ester): —OP(=O)(OR)$_2$, where R is a phosphate substituent, for example, —H, a $C_{1-7}$alkyl group, or a $C_{5-20}$ aryl group.

Phosphorous acid: —OPH(=O)(OH).

Phosphite: —OP(OR)$_2$, where R is a phosphite substituent, for example, —H, a $C_{1-7}$ alkyl group, or a $C_{5-20}$ aryl group.

Phosphoramidite: —OP(OR$^5$)—NR$^6{}_2$, where R$^5$ and R$^6$ are phosphoramidite substituents, for example, —H, a $C_{1-7}$ alkyl group, or a $C_{5-20}$ aryl group.

Phosphoramidate: —OP(=O)(OR$^5$)—NR$^6{}_2$, where R$^5$ and R$^6$ are phosphoramidate substituents, for example, —H, a alkyl group, or a $C_{5-20}$ aryl group.

Siloxy (silyl ether): —OSiR$_3$, where SiR$_3$ is a silyl group, as discussed above.

Isomers

Certain compounds may exist in one or more particular geometric, optical, enantiomeric, diasteriomeric, stereoisomeric or tautomeric forms, and are herein collectively referred to as "isomers" (or "isomeric forms"). Note that, except as discussed below for tautomeric forms, specifically excluded from the term "isomers," as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH.

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

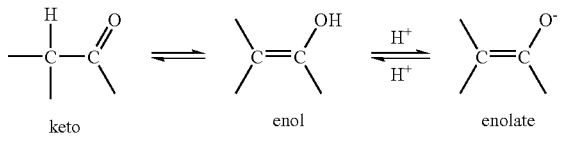

keto    enol    enolate

Note that specifically included in the term "isomer" are compounds with one or more isotopic substitutions. For example, H may be in any isotopic form, including $^1$H, $^2$H (D), and $^3$H (T).

Unless otherwise specified, a reference to a particular compound includes all such isomeric forms, including (wholly or partially) racemic and other mixtures thereof.

Salts

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic, such as an acidic group (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4{}^+$) and substituted ammonium ions (e.g., NH$_3$R$^+$, NH$_2$R$_2{}^+$, NH$_2$R$_2{}^+$, NR$_4{}^+$).

Unless otherwise specified, a reference to a particular compound also include salt forms thereof.

Solvates

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate.

Unless otherwise specified, a reference to a particular compound also include solvate forms thereof.

Throughout this application references to medical treatment are intended to include both human and veterinary treatment, and references to pharmaceutical compositions are accordingly intended to encompass compositions for use in human or veterinary treatment.

BRIEF DESCRIPTION OF THE DRAWINGS

Experimental data illustrating the present invention will now be described by reference to the accompanying figures, in which.

EMBODIMENTS OF THE INVENTION AND EXPERIMENTAL DATA

Figure 1:
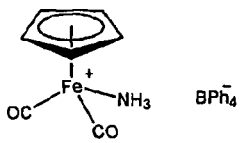
FIG. 1 is a table presenting CO release data and solubility data for some example compounds, which were proposed as being suitable as CO releasers to a physiological system in WO 03/066067.
Figure 1:
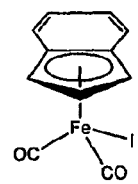
Figure 1:
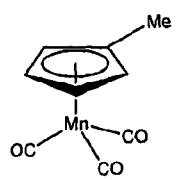
Figure 2:
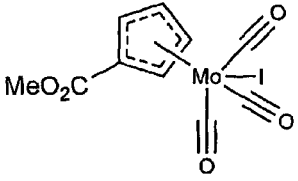
FIG. 2 is a table presenting data of solubility, CO release, cytotoxicity and anti-inflammatory action for some compounds according to the present invention, and also data of two comparative compounds (CORM-358 and CORM-360).
Figure 2:
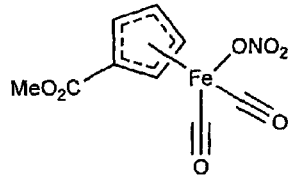
Figure 2:
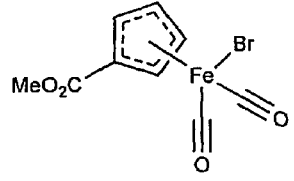
Figure 2:
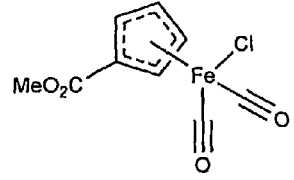
Figure 2:
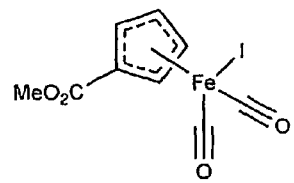

Detection of CO Liberated from Transition Metal Carbonyl Complexes

The release of CO from metal carbonyl complexes was assessed spectrophotometrically by measuring the conversion of deoxymyoglobin (deoxy-Mb) to carbonmonoxymyoglobin (MbCO). MbCO has a distinctive absorption spectrum between 500 and 600 nm, and changes at 540 nm were used to quantify the amount of CO liberated. Myoglobin solutions were prepared freshly by dissolving a known concentration of the protein in phosphate buffer, which was also made up to a known concentration and pH. Sodium dithionite (0.1%) was added to convert myoglobin to deoxy-Mb prior to each reading. All the spectra were measured using a Helios α spectrophotometer.

Cytotoxicity

Cytotoxicity was measured in RAW264.7 macrophages incubated for 24 h with 10, 50 or 100 µM of each compound. The loss in cell viability was measured using the Alamar Blue and LDH release assays as a percentage of control. In Table 2, * indicates toxicity detected at 100 µM;  indicates toxicity detected at 50 µM; * indicates toxicity detected at 10 µM; V indicates that cells were viable and no toxicity was detected up to 100 µM.

Anti-Inflammatory Action

The anti-inflammatory action was measured in RAW264.7 macrophages incubated for 24 h with 10, 50 or 100 µM of each compound in the presence or absence of Lipopolysaccharide (LPS) (1 µg/ml). Nitrite was used as an indicator of inflammation. In Table 2, * indicates a reduction in inflammation detected at 100 µM;  indicates a reduction in inflammation detected at 50 µM; * indicates a reduction in inflammation detected at 10 µM; "None" indicates there was no effect of the compound on inflammation.

In Table 2, N.D.=not determined.

Preparation of $C_5H_5COOMe$

A solution of LiCp was prepared by the addition of 156.3 ml (0.25 mol) of n-BuLi (1.6M in hexanes) to 20.65 ml (0.25 mol) of freshly cracked cyclopentadiene in 280 ml of dry THF at −78° C., under argon. After complete addition, the system is allowed to warm slowly to room temperature and then stirred for a further hour. During this time a copious white precipitate is formed.

Following this, the system is again cooled to −78° C. (at which point the precipitate starts to redissolve) and 19.3 ml (0.25 mol) of methyl chloroformate is added dropwise. This results in complete disappearance of the white precipitate and formation of a yellow/orange coloured solution. After warming to room temperature and then stirring for a further hour, a white precipitate is produced (LiCl).

500 ml of water is added and the two layers separated. The aqueous layer is washed with 2×100 ml portions of ether, and then the combined organic extracts are washed with 5×250 ml portions of water then 1× saturated brine. It is then dried ($MgSO_4$ at 0° C. for 45 mins) and then the solvent removed on rotary evaporator to give a yellow oil. The yellow oil is used without further purification.

Reaction of $C_5H_5COOMe$ with $Fe(CO)_5$ (10)

The product obtained from the above reaction was refluxed with 20 ml (0.15 mol) of $Fe(CO)_5$ in 110 ml of heptane/diglyme (10:1), under argon for 20 hrs. Following this, the system is cooled to −18° C. overnight, and the resulting purple precipitate is collected on a sinter. It is washed with 2× portions of cold pentane.

The precipitate yields the product $[Fe(Cp-COOMe)(CO)_2]_2$ which may be purified by column chromatography on silica, eluting with petrol to remove unreacted $Fe(CO)_5$ and then petrol/ether (1:1) to elute the product. Approximately 2.5 to 3 g of $[Fe(Cp-COOMe)(CO)_2]_2$ was obtained using this method.

Alternatively, the crude $[Fe(Cp-COOMe)(CO)_2]_2$ product may be purified by recrystallisation from DCM/hexane (following several hours under high vacuum to remove any traces of solvent and unreacted $Fe(CO)_5$). This method gave higher yields and around 4 g of product was obtained in this way.

Reaction of $C_5H_5COOMe$ with $Fe_2(CO)_9$ (11)

An alternative method for the synthesis of $[Fe(Cp-COOMe)(CO)_2]_2$ involves a reaction with $Fe_2(CO)_9$.

$C_5H_5COOMe$, prepared from the above reaction, is refluxed with 20 g (55.0 mmol) of $Fe_2(CO)_9$ in 200 ml of de-oxygenated heptane (argon purge), under argon for 24 hrs. After reflux, it is cooled to −18° C. overnight and a purple crystalline precipitate results, which may be collected on a sinter and washed with several portions of pentane. The heptane supernatant may be recycled, which may increase the yield. The yield typically varies from 4.5 to 6 g. (17.4-23.2% based on $Fe_2(CO)_9$). An advantage of this route is that recrystallisation is not required.

Analytical Data for $[Fe(Cp-COOMe)(CO)_2]_2$

I.R. ($CH_2Cl_2$) $v_{max}$=2010.13, 1973.15 cm$^{-1}$ (terminal CO), 1793.23 cm$^{-1}$ (bridging CO), 1718.26 cm$^{-1}$ (C=O).

$^1$H-NMR ($d_6$-acetone) δ=3.90 (3H), 5.17 (2H), 5.45 (2H).

Preparation of $[Fe(Cp-CO_2CH_2CH_2OH)(CO)_2]_2$ 1.013 g (2.16 mmol) of $[Fe(Cp-COOMe)(O)_2]_2$ and 15 mg (0.375 mmol) of NaH (60% disp. in mineral oil) were stirred in 18 ml of ethylene glycol at 55° C. overnight, under argon.

Following this, DCM and de-oxygenated water were added, and the two layers separated. The aqueous layer is washed with DCM and then the combined DCM extracts are washed with 3× portions of de-oxygenated water and 1× saturated brine. It was then dried (MgSO$_4$) and the solvent removed on rotary evaporator. The resulting solid is washed with several portions of ether.

1.001 g of dark purple solid was produced in a yield of 87.5%. The sample may be recrystallised from DCM/hexane, which lowers the yield to around 62%.

Analytical Data for [Fe(Cp-CO$_2$CH$_2$CH$_2$OH)(CO)$_2$]$_2$

I.R. (CH$_2$Cl$_2$) $v_{max}$=2012.13, 1975.15 cm$^{-1}$ (terminal CO), 1785.23 cm$^{-1}$ (bridging CO), 1718.26 cm$^{-1}$ (C=O).

$^1$H-NMR (CD$_2$Cl$_2$) δ=3.97 (2H), 4.45 (2H), 5.03 (2H), 5.35 (obscured by DCM peak) (2H).

Preparation of [Fe(Cp-CO$_2$CH$_2$CH$_2$OH)(CO)$_3$][PF$_6$] {CORM-337} (12)

500 mg (0.943 mmol) of [Fe(Cp-CO$_2$CH$_2$CH$_2$OH)(CO)$_2$]$_2$ and 615 mg (1.86 mmol, 0.985 eq) of ferrocinium hexafluorophosphate were placed in a Schlenk tube under a CO atmosphere. 70 ml of a CO-saturated DCM/THF mixture (2:1) was then added and the system stirred for 2.5-3 days in the dark with periodic bubbling of CO through the solution.

Following this, some yellow precipitate had started to form and precipitation was completed by addition of ether (150 ml). After stirring for 10 mins the product was collected on a sinter, washed several times with ether, and then dried under vacuum.

485 mg of a pale yellow solid was obtained. Yield was 59.7%.

Analytical Data for [Fe(Cp-CO$_2$CH$_2$CH$_2$OH)(CO)$_3$][PF$_6$]

I.R. (solid) $v_{max}$=2134.4, 2102.1, 2077.6 cm$^{-1}$ (CO), 1719.6 cm$^{-1}$ (C=O).

$^1$H-NMR (d$_6$-acetone) δ=3.89 (2H), 4.40 (2R), 6.20 (2H), 6.77 (2H).

Preparation of Methyl Iodoacetate

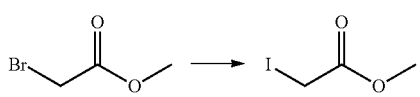

The following procedure was based on a modified literature method (14). A mixture of methyl bromoacetate (20.00 g, 12.40 mL, 130.74 mmol) and sodium iodide (25.10 g, 167.34 mmol, 1.28 equiv.) in acetone (90 mL) was stirred at room temperature for 15 hours and then heated at 50° C. for 2 hours. The reaction mixture was then cooled to ambient temperature, filtered to remove sodium bromide and the solid was washed with diethyl ether (2×50 mL). The filtrate was concentrated in vacuo, diluted with diethyl ether (100 mL) and the organic layer was washed with water (2×50 mL)), brine (50 mL), dried (anhydrous sodium sulfate) and evaporated to give methyl iodoacetate (18.69 g, 93.46 mmol, 72%) as a dark red oil.

$^1$H NMR (400 MHz, CDCl$_3$) δ 3.73 (3H, s, OCH$_3$), 3.68 (2H, s, ICH$_2$).

Preparation of Methyl 3-iodopropionate

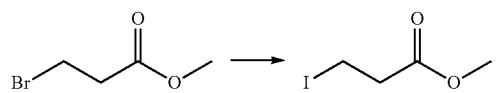

Using the above modified Finkelstein procedure (14), methyl 3-iodopropionate (23.10 g, 107.94 mmol, 90%) was prepared from methyl 3-bromopropionate (20.00 g, 119.75 mmol) and sodium iodide (22.98 g, 153.28 mmol, 1.28 equiv.) in acetone (80 mL) as an orange oil.

$^1$H NMR (400 MHz, CDCl$_3$) δ 3.71 (3H, s, OCH$_3$), 3.31 (2H, s, J=7.2 Hz, ICH$_2$), 2.97 (2H, s, J=7.2 Hz, CH$_2$CO$_2$).

Preparation of Methyl Cyclopenta-1,3-dienylacetate and Methyl Cyclopenta-1,4-dienylacetate

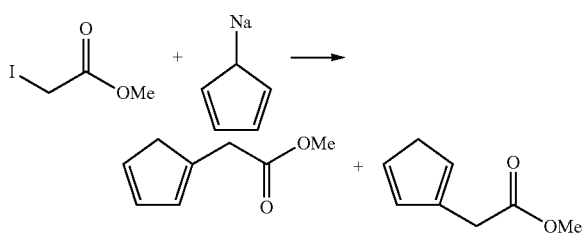

The above compounds were prepared using a modified literature method (15, 16). A solution of methyl iodoacetate (18.50 g, 92.51 mmol) in anhydrous tetrahydrofuran (60 mL) was added dropwise to a 2.0 M solution of sodium cyclopentadienide (46.26 mL, 92.51 mmol) in tetrahydrofuran over 15 minutes under nitrogen at −78° C. The resulting reaction mixture was stirred for a further 3 hours at −78° C. and then warmed to room temperature, filtered and the resulting solid was washed with diethyl ether (200 mL). The combined organics were concentrated in vacuo. The crude oil was purified by flash chromatography on silica using 10% ethyl acetate in iso-hexane to afford methyl 3-cylopenta-1,3-dienylacetate(1-alkylCp) and methyl 3-cylopenta-1,4-dienylacetate(2-alkylCp) (2.37 g, 17.31 mmol, 19%) as yellow liquids in a approx. 1:1 ratio. $^1$H NMR (500 MHz, CDCl$_3$) δ 6.53 (1H, m, cyclopentadiene CH), 6.46 (2H, m, cyclopentadiene CH), 6.37 (2H, m, cyclopentadiene CH), 6.23 (1H, m, cyclopentadiene CH), 3.72 (3H, s, OCH$_3$), 3.71 (3H, s, OCH$_3$), 3.47 (2H, m, alkyl CH$_2$), 3.44 (2H, m, alkyl CH$_2$), 3.04 (2H, m, cycloalkyl CH$_2$), 3.02 (2H, m, cycloalkyl CH$_2$).

Preparation of Methyl 3-cylopenta-1,3-dienylpropionate and Methyl 3-cylopenta-1,4-dienylpropionate

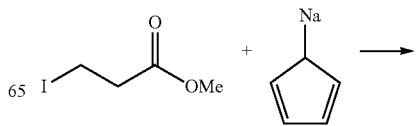

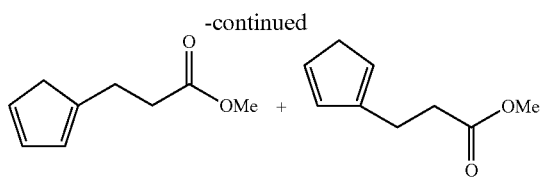

The above compounds were prepared using a modified literature method (16). A 2.0 M solution of sodium cyclopentadienide in tetrahydrofuran (105.10 mL, 210.28 mmol) was added dropwise over 15 minutes to a stirred solution of methyl 3-iodopropionate (45.00 g, 210.28 mmol) in anhydrous diethyl ether (280 mL) and anhydrous tetrahydrofuran (200 mL) under nitrogen at −78° C. The resulting reaction mixture was stirred at −78° C. for 2 hours and then stored at −20° C. for a further 15 hours. The resulting red suspension was quenched with 1 M ammonium chloride solution (800 mL), and the organic phase was extracted with diethyl ether (5×400 mL). The combined organic layer was washed with 1 M ammonium chloride solution (2×500 mL) and dried (anhydrous sodium sulfate), filtered and concentrated in vacuo. The crude oil was purified by flash chromatography on silica using 5% ethyl acetate in iso-hexane to afford methyl 3-cylopenta-1,3-dienylpropionate (1-alkylCp) and methyl 3-cylopenta-1,4-dienylpropionate (2-alkylCp) (14.72 g, 96.72 mmol, 46%) as yellow liquids in a 1.2:1 ratio.

Major isomer (1-alkylCp): $^1$H NMR (400 MHz, CDCl$_3$) δ 6.40 (1H, m, Cp-H3, overlaps with xb), 6.25 (1H, m, Cp-H4), 6.02 (1H, m, Cp-H2), 3.66 (3H, s, OCH$_3$), 2.93 (2H, dd, J=3.7 and 1.9 Hz, Cp-H5), 2.71 (2H, m, CH$_2$CO$_2$, overlaps with xb), 2.55 (2H, m, CpCH$_2$, overlaps with xb); Minor isomer (2-alkylCp): $^1$H NMR (400 MHz, CDCl$_3$) δ 6.40 (1H, m, Cp-H3, overlaps with xa), 6.39 (1H, m, Cp-H4, overlaps with xa), 6.16 (1H, m, Cp-H1), 3.66 (3H, s, OCH$_3$), 2.88 (2H, dd, J=2.9 and 1.5 Hz, Cp-H5), 2.71 (2H, m, CH$_2$CO$_2$, overlaps with xa), 2.55 (2H, m, CpCH$_2$, overlaps with xa).

Preparation of [Fe(C$_5$H$_4$CH$_2$CO$_2$Me)(CO)$_2$]$_2$

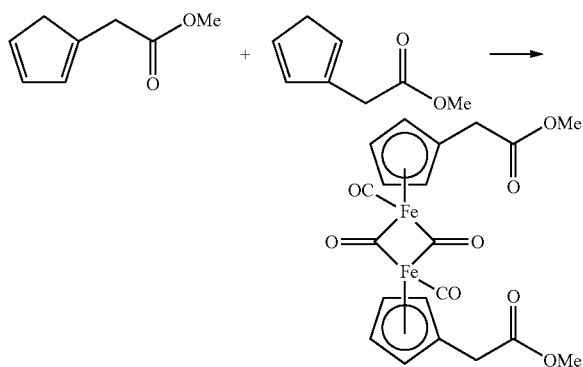

A mixture of methyl 3-cylopenta-1,3-dienylacetate(1-alkylCp) and methyl 3-cylopenta-1,4-dienylacetate(2-alkylCp) (2.00 g, 14.59 mmol) in degassed heptane (55 mL) was added to diiron nonacarbonyl (5.31 g, 14.59 mmol) under nitrogen at room temperature. The resulting reaction mixture was heated to reflux at 110° C. and stirred for 18 hours, then cooled to ambient temperature during which precipitation of maroon-like crystals were observed. The solution was further cooled in the freezer for 1 hour and then the solution was filtered through a sinter funnel. The crystals collected were washed thoroughly with degassed hexane (4×50 mL). The crystals were dissolved in degassed dichloromethane (4×50 mL) and the solvent was concentrated in vacuo to yield the iron sandwich complex (2.67 g, 5.36 mmol, 30%) as maroon-like crystals.

IR (solid) ν$_{max}$ cm$^{-1}$ 1979 (s, terminal CO), 1946 (s, terminal CO), 1759 (s, bridging C=O), 1737 (s, ester C=O); $^1$H NMR (500 MHz, CD$_2$Cl$_2$, room temperature) δ 4.76 (4H, s, 4×cyclopentadiene CH), 4.69 (4H, s, 4×cyclopentadiene CH), 3.74 (6H, s, 2×OCH$_3$), 3.56 (4H, s, 2×alkyl CH$_2$); $^{13}$C NMR (126 MHz, CD$_2$Cl$_2$, −30° C.) δ 272.5 (2×bridging C=O), 210.3 (2× terminal CO), 171.2 (2×ester C=O), 98.0 (2×quaternary cyclopentadiene C), 89.7 (4×cyclopentadiene CH), 89.4 (4×cyclopentadiene CH), 52.5 (2×OCH$_3$), 32.4 (2×alkyl CH$_2$).

Preparation of [Fe(C$_5$H$_4$CH$_2$CH$_2$CO$_2$Me)(CO)$_2$]$_2$

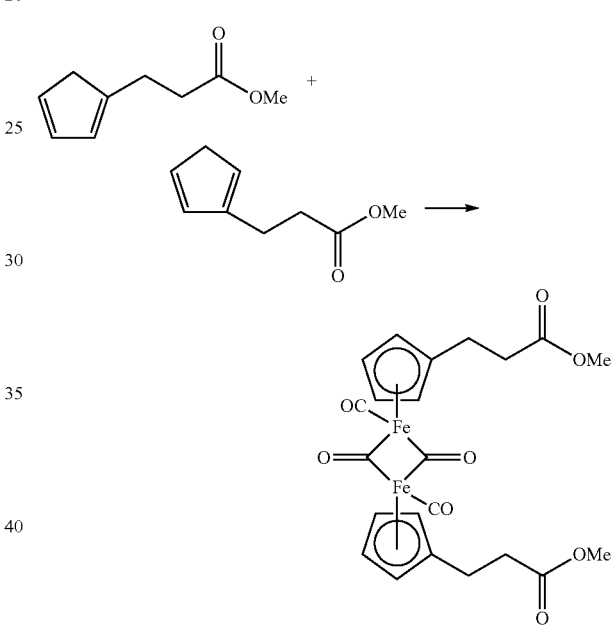

Using the above iron sandwich compound procedure, [Fe(C$_5$H$_4$CH$_2$CH$_2$CO$_2$Me)(CO)$_2$]$_2$ (12.75 g, 24.20 mmol, 50%) was prepared as maroon-like crystals from a mixture of methyl 3-cylopenta-1,3-dienylpropionate and methyl 3-cylopenta-1,4-dienylpropionate (1.2:1, 14.50 g, 95.96 mmols) and diiron nonacarbonyl (34.90 g, 95.96 mmol) in degassed heptane (350 mL).

IR (solid) ν$_{max}$ cm$^{-1}$ 1976 (s, terminal CO), 1937 (s, terminal CO), 1788 (s, bridging C=O), 1715 (s, ester C=O); $^1$H NMR (500 MHz, CD$_2$Cl$_2$, room temperature) δ 4.67 (4H, s, 4× cyclopentadiene CH), 4.56 (4H, s, 4×cyclopentadiene CH), 3.71 (6H, s, 2×OCH$_3$), 2.80 (4H, s, 2×alkyl CH$_2$), 2.66 (4H, s, 2×alkyl CH$_2$); $^1$H NMR (500 MHz, CD$_2$Cl$_2$, −30° C.) δ 4.67 (4H, s, 4×cyclopentadiene CH), 4.57 (4H, s, 4×cyclopentadiene CH), 3.67 (6H, s, 2×OCH$_3$), 2.76 (4H, s, 2×alkyl CH$_2$), 2.68 (4H, s, 2×alkyl CH$_2$); $^1$H NMR (500 MHz, CD$_2$Cl$_2$, −50° C.) δ 4.58 (8H, s, 8×cyclopentadiene CH), 3.65 (6H, s, 2×OCH$_3$), 2.68 (8H, s, 4×alkyl CH$_2$); $^{13}$C NMR (126 MHz, CD$_2$Cl$_2$, room temperature) δ 172.7 (2×ester C=O), 105.6 (2×quaternary cyclopentadiene C), 88.3 (4×cyclopentadiene CH), 87.4 (4×cyclopentadiene CH), 51.5 (2×OCH$_3$), 34.3 (2×alkyl CH$_2$), 22.5 (2×alkyl CH$_2$); $^{13}$C NMR (126

MHz, CD$_2$Cl$_2$, −30° C.) δ 272.9 (2×bridging C=O), 210.8 (2×terminal CO), 173.1 (2×ester C=O), 105.2 (2×quaternary cyclopentadiene C), 87.9 (4×cyclopentadiene CH), 87.0 (4×cyclopentadiene CH), 52.1 (2×OCH$_3$), 34.3 (2×alkyl CH$_2$), 22.5 (2×alkyl CH$_2$).

Preparation of Tricarbonyl[methyl-2-(cyclopentadienyl)ethanoate]iron tetrafluoroborate [Fe(C$_5$H$_4$CH$_2$CO$_2$Me)(CO)$_3$]BF$_4$ CORM-351

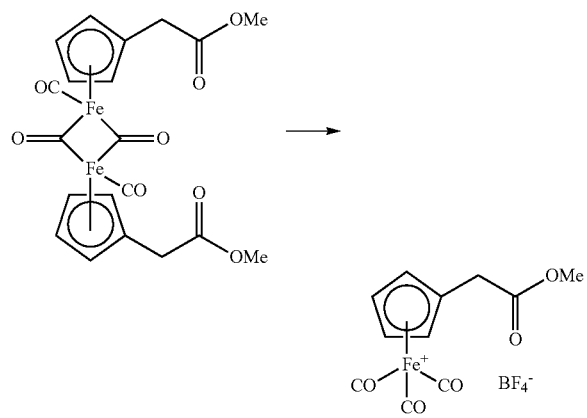

The following procedure was based on a modified literature method (12). Ferrocinium tetrafluoroborate (274 mg, 1.004 mmol, 2 equiv.) was added to the iron sandwich compound [Fe(C$_5$H$_4$CH$_2$CO$_2$Me)(CO)$_2$]$_2$ (250 mg, 0.502 mmol) under nitrogen. An anhydrous mixture of degassed dichloromethane/tetrahydrofuran (33 mL; 2:1) was added and carbon monoxide was then bubbled through the resulting reaction mixture for a period of 15 minutes. The reaction mixture was then stirred under a carbon monoxide atmosphere with bubbling of carbon monoxide through the reaction mixture after 18 and 24 hours for a period of 10 minutes. In total, the reaction mixture was stirred under a carbon monoxide atmosphere for 36 hours after which the reaction flask was flushed with nitrogen. The reaction mixture was then concentrated in vacuo and the resulting black solid was washed with degassed diethyl ether (5×20 mL), after which the product was extracted with degassed dichloromethane (5×20 mL). The combined organic layers were concentrated in vacuo to give an orange solid which was then washed with degassed dichloromethane (20 mL). The resulting yellow solid was dissolved in acetone (20 mL), filtered and the solvent removed in vacuo to give the title compound as a yellow solid (66.4 mg, 0.183 mmol, 36%).

IR (solid) ν$_{max}$ cm$^{-1}$ 2121 (s, terminal CO), 2065 (s, terminal CO), 1737 (s, ester CO); $^1$H NMR (500 MHz, CD$_3$COCD$_3$, room temperature, low concentration sample) δ 6.25 (2H, t, 2×cyclopentadiene CH), 6.08 (2H, t, 2×cyclopentadiene CH), 3.87 (2H, s, alkyl CH$_2$), 3.77 (3H, s, OCH$_3$); $^1$H NMR (500 MHz, CD$_3$COCD$_3$, room temperature, high concentration sample) δ 6.22 (2H, s, 2×cyclopentadiene CH), 6.06 (2H, s, 2×cyclopentadiene CH), 3.86 (2H, s, alkyl CH$_2$), 3.77 (3H, s, OCH$_3$); $^{13}$C NMR (126 MHz, CD$_3$COCD$_3$, −30° C.) δ 204.7 (3×terminal CO), 170.9 (ester C=O), 106.4 (quaternary cyclopentadiene C), 92.9 (2×cyclopentadiene CH), 89.7 (2×cyclopentadiene CH), 53.4 (OCH$_3$), 32.1 (alkyl CH$_2$).

Preparation of Tricarbonyl[methyl-3-(cyclopentadienyl)propanoate]iron tetrafluoroborate [Fe(C$_5$H$_4$CH$_2$CH$_2$CO$_2$Me)(CO)$_3$]BF$_4$ CORM-352

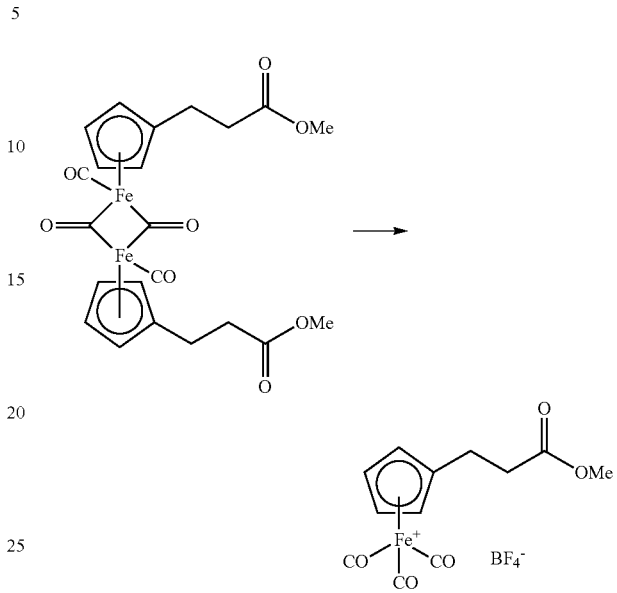

Using the ferrocinium oxidation procedure (12), [Fe(C$_5$H$_4$CH$_2$CH$_2$CO$_2$Me)(CO)$_3$]BF$_4$ (95.0 mg, 0.251 mmol, 15%) was prepared as a yellow solid from iron sandwich compound [Fe(C$_5$H$_4$CH$_2$CH$_2$CO$_2$Me)(CO)$_2$]$_2$ (900 mg, 1.71 mmol) and ferrocinium tetrafluoroborate (933 mg, 3.42 mmol, 2 equiv.) under a carbon monoxide atmosphere for 36 hours.

IR (solid) ν$_{max}$ cm$^{-1}$ 2059 (s, terminal CO), 2009 (s, terminal CO), 1735 (s, ester CO); $^1$H NMR (400 MHz, CD$_3$COCD$_3$, room temperature, low concentration sample) δ 6.15 (2H, t, 2×cyclopentadiene CH), 6.07 (2H, t, 2×cyclopentadiene CH), 3.67 (3H, s, OCH$_3$), 2.94 (2H, t, alkyl CH$_2$), 2.80 (2H, t, alkyl CH$_2$, signal overlaps with H$_2$O signal in CD$_3$COCD$_3$ NMR solvent); $^1$H NMR (500 MHz, CD$_3$COCD$_3$, room temperature, high concentration sample) δ 6.13 (2H, s, 2×cyclopentadiene CH), 6.05 (2H, s, 2×cyclopentadiene CH), 3.67 (3H, s, OCH$_3$), 2.93 (2H, t, alkyl CH$_2$), 2.82 (2H, t, alkyl CH$_2$, signal overlaps with H$_2$O signal in CD$_3$COCD$_3$ NMR solvent); $^{13}$C NMR (126 MHz, CD$_3$COCD$_3$, −30° C.) δ 203.7 (3×terminal CO), 172.1 (ester C=O), 114.1 (quaternary cyclopentadiene C), 89.4 (2×cyclopentadiene CH), 88.8 (2×cyclopentadiene CH), 51.4 (OCH$_3$), 32.8 (alkyl CH$_2$), 22.2 (alkyl CH$_2$).

Preparation of [Fe(O$_5$H$_4$CO$_2$Me)(CO)$_3$][FeCl$_4$] CORM-357

400 mg (0.851 mmol) of [Fe(C$_5$H$_4$—COOMe)(CO)$_2$]$_2$ was dissolved in 20 ml of benzene, under argon. A solution of SO$_2$Cl$_2$ in benzene was then added drop-wise with stirring. This resulted in the immediate formation of a yellow precipitate. The reaction was followed by IR spectroscopy, and when there was no more of the dimer starting material still present, addition was ceased. The resulting precipitate was collected on a sinter and then washed with benzene and a little cold dichloromethane (DCM). It was then recrystallised from DCM (i.e. sample dissolved in boiling DCM and then cooled to −18'C overnight). The resulting yellow crystals were isolated, washed with diethyl ether and then dried under vacuum.

101 mg (0.219 mmol) of product obtained. $M^r$=460.66. Yield 26%. X-ray quality crystals were obtained from a dilute solution in MeCN/diethyl ether/pentane at −18° C.

$^1$H NMR (CD$_3$CN): δ(ppm) v. broad due to paramagnetic counter ion $^{13}$C NMR (CD$_3$CN): δ(ppm) 60.6 (CH$_3$), 91.3 (ipso Cp), 97.2 (Cp), 99.8 (Cp), 161.7 (C=O), 202.7 (CO)

$^{17}$O NMR (CD$_3$CN): δ(ppm) 399.2 (CO)

IR (MeCN) ν(cm$^{-1}$): 2132 (s), 2089 (vs), 1745 (m)

Mass Spec (m/z): 263 (M$^+$), 235 (M$^+$-CO), 207 (M$^+$-2CO)

Elemental: Fe$_2$C$_{10}$H$_7$O$_5$Cl$_4$ found (calc) C, 26.14 (26.07); H, 1.62 (1.53), Cl: 30.80 (30.78).

Preparation of [(MeC$_5$H$_3$(COOH))Mn(CO)$_3$] (mixture of both isomers)

CORM-359 is a mixture of two isomers in approximately equal quantities:—

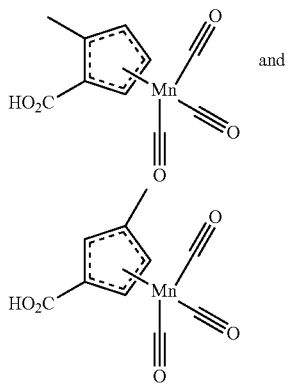

and

[{MeC$_5$H$_3$(COOH)}Mn(CO)$_3$] (Mixture of Both Isomers)

This known compound is reported in references 19 and 20.

A solution of [Mn(Cp-Me)(CO)$_3$] (1.50 g, 6.88 mmol) in dry THF (15 ml) was cooled to −78° C. 1.5 eq of BuLi (6.45 ml, 10.32 mmol, 1.6M soln. in hexanes) was then added drop-wise with stirring. Stirring was continued at −78° C. for 10 min, and then the reaction was allowed to warm to room temperature.

The solution was then poured onto a large excess of dry ice, and allowed to react until there was no solid CO$_2$ remaining. Diethyl ether was then added and the reaction poured into water. The water washing was discarded and then the organic phase extracted with three portions of 1M NaOH (aq). The combined basic aqueous extracts were then washed with two portions of diethyl ether and acidified with 10% HCl (aq). Diethyl ether was then added to dissolve the precipitated product, and the two phases separated. The organic phase was then washed with two portions of water and finally saturated brine, before being dried over MgSO$_4$. Removal of solvent gave 512 mg (1.95 mmol) of a yellow/brown solid. Crude yield 28%.

A sample of this was recrystallised from hexane to give 184 mg (0.702 mmol) of a yellow solid. $M^r$=262.10. Recrystallised yield 10% (although not all of sample was recrystallised).

$^1$H NMR (CD$_2$Cl$_2$): δ(ppm) 2.05 (s, 3H Me, isomer 1, relative intensity 1.35), 2.29 (s, 3H Me, isomer 2, relative intensity 1.0), 4.79 (broad, Cp 3H), 5.38 (broad, Cp 2H), 5.49 (d J=9.2 Hz, Cp 1H).

Only limited assignment possible due to broad spectrum. No differentiation possible between isomers for the Cp protons.

$^{13}$C NMR (CD$_2$Cl$_2$): δ(ppm) 13.4 (Me both isomers), 80.4, 80.8 (Cp C—CO$_2$H, 2 isomers), 81.8, 84.1, 84.7, 87.2, 87.7, 88.2 (Cp C—H, 2 isomers, 3 C per isomer) 103.5, 108.4 (Cp C-Me, 2 isomers), 171.8 (C=O broad, 2 isomers), 223.3 (CO, 2 isomers)

$^{17}$O NMR (CD$_2$Cl$_2$): δ(ppm) 378.0 (CO isomer 1), 379.1 (CO isomer 2)

$^{55}$Mn NMR (CD$_2$Cl$_2$): Could not be obtained

IR(CH$_2$Cl$_2$) ν(cm$^{-1}$): 2031 (s), 1948 (vs), 1727 (w), 1691 (w)

Mass Spec (m/z): 261 (M$^-$ i.e. —H$^+$)

Elemental: MnC$_{10}$H$_7$O$_5$ found (calc) C, 47.31 (45.83); H, 3.24 (2.69).

Preparation of [Mo(C$_5$H$_4$CO$_2$Me)(CO)$_3$I] CORM-361

The compound [Mo(C$_5$H$_4$CO$_2$Me)(CO)$_3$I] was prepared using a literature method (17).

Preparation of [Fe(C$_5$H$_4$—CO$_2$Me)(CO)$_2$(NO$_3$)] CORM-380

300 mg (0.638 mmol) of [Fe(C$_5$H$_4$CO$_2$Me)(CO)$_2$]$_2$ and 228 mg (1.34 mmol) of AgNO$_3$ were stirred together in 15 ml of acetone at 30° C., under argon. The reaction was monitored by IR spectroscopy and after 1.5 h the reaction was shown to be complete. The solution was filtered through celite and then the solvent removed on a rotary evaporator to give a red oily residue. A silica gel column was prepared in petroleum ether (40/60). The compound was introduced as a solution in a little DCM. Elution with petroleum ether caused no band movement. Elution with petroleum ether/diethyl ether (1:1) gave a very small amount of a yellow band. The product was eluted as a bright red band with diethyl ether. Removal of solvent on a rotary evaporator, washing with petroleum ether and drying under vacuum gave the desired solid product.

78 mg of a bright red solid was obtained (0.263 mmol). $M^r$=297.00. Yield 21%. X-ray quality crystals were obtained from a diethyl ether solution at −18° C.

$^1$H NMR (CD$_2$Cl$_2$): δ(ppm) 3.93 (s, CH$_3$), 5.21 (s, Cp 2H), 5.78 (s, Cp 2H)

$^{13}$C NMR (CD$_2$Cl$_2$): δ(ppm) 53.0 (Me), 82.7 (Cp), 83.9 (Cp ipso), 91.5 (Cp), 164.0 (C=O), 209.0 (CO)

$^{17}$O NMR (CD$_2$Cl$_2$) δ(ppm) 393.7 (CO)

IR (CH$_2$Cl$_2$) ν(cm$^{-1}$): 2076 (s), 2036 (s)

Mass Spec (m/z): No relevant peaks seen in EI$^+$.

Elemental: FeC$_9$H$_7$NO$_7$ found (calc) C, 35.73 (36.40); H, 2.44 (2.38); N, 4.66 (4.72).

Preparation of [Fe(C$_5$H$_4$—CO$_2$Me)(CO)$_2$BR] CORM-382

400 mg (0.851 mmol) of [Fe(C$_5$H$_4$—CO$_2$Me)(CO)$_2$]$_2$ was dissolved in 20 ml of DCM, under argon. A solution of 150 mg (0.936 mmol) of Br$_2$ in 5 ml of DCM was then added drop-wise with stirring. After complete addition, stirring was continued for a further 30 min, after which time reaction was shown to be complete by IR spectroscopy.

The reaction solution was then transferred to a separating funnel and more DCM was added. It was then washed with three portions of de-oxygenated Na$_2$S$_2$O$_3$ (aq) and once with de-oxygenated water. Then it was dried (MgSO$_4$), filtered, and then the solvent removed on a rotary evaporator to give a red-brown solid. A silica gel column was prepared in petroleum ether (40/60). The product was introduced as a solution in a little DCM. The column was initially eluted with petroleum ether but this caused no movement of bands. The polarity was increased using diethyl ether, and the product was finally eluted as a dark red band with petroleum ether/diethyl ether (2:3). Removal of solvent gave the product as a dark red solid, which was dried under vacuum.

268 mg (0.851 mmol) of product obtained. $M^r$=314.90. Yield 50%. X-ray quality crystals were grown from a diethyl ether solution at −18° C.

$^1$H NMR (CD$_2$Cl$_2$): δ(ppm) 3.90 (s, Me 3H), 5.19 (s, Cp 2H), 5.70 (s, Cp 2H)

$^{13}$C NMR (CD$_2$Cl$_2$): δ(ppm) 52.7 (Me), 83.2 (Cp), 84.0 (Cp ipso), 90.8 (Cp), 164.3 (C=O), 210.8 (CO)

$^{17}$O NMR (CD$_2$Cl$_2$): δ(ppm) 385.7 (CO)

IR (CH$_2$Cl$_2$) ν(cm$^{-1}$): 2060 (s), 2018 (s)

Mass Spec (m/z): 314 (M$^+$), 286 (M$^+$-CO), 258 (M$^+$-2CO)

Elemental: FeC$_9$H$_7$O$_4$Br found (calc) C, 34.68 (34.33); H, 2.14 (2.24); Br, 25.16 (25.37).

Preparation of [Fe(C$_5$H$_4$—CO$_2$Me)(CO)$_2$Cl] CORM-384

500 mg (1.06 mmol) of [Fe(C$_5$H$_4$—CO$_2$Me)(CO)$_2$]$_2$ was dissolved in 14 ml of dry THF, under argon. A solution of 127 mg (1.06 mmol) of SOCl$_2$ in 5 ml dry THF was then added drop-wise with stirring. After complete addition, stirring was continued for a further 25 min. Following this, IR showed that there was still some starting material present. Hence a dilute THF solution of SOCl$_2$ was prepared and aliquots of this were added, the reaction was stirred for 5 min, and then the IR spectrum recorded until reaction was complete. Following this, the solvent was removed on a rotary evaporator and the residue columned on silica gel. Initially prepared in petroleum ether, it was then eluted with chloroform, with the product finally being eluted as a red band with diethyl ether. Solvent was removed on a rotary evaporator and then the product recrystallised from diethyl ether/petroleum ether.

252 mg (0.932 mmol) of a red crystalline solid was obtained. $M^r$=270.45. Yield 44%. X-ray quality crystals were grown from a more dilute diethyl ether solution, at −18° C.

$^1$H NMR (CD$_2$Cl$_2$): δ(ppm) 3.93 (s, Me 3H), 5.18 (s, Cp 2H), 5.70 (s, Cp 2H)

$^{13}$C NMR (CD$_2$Cl$_2$): δ(ppm) 52.7 (Me), 83.0 (Cp), 84.5 (Cp ipso), 91.6 (Cp), 164.4 (C=O), 210.5 (CO)

$^{17}$O NMR (CD$_2$Cl$_2$): δ(ppm) 386.4 (CO)

IR (CH$_2$Cl$_2$) ν(cm$^{-1}$): 2064 (s), 2022 (s)

Mass Spec (m/z): 270 (M$^+$), 242 (M$^+$-CO), 214 (M$^+$-2C0)

Elemental: FeC$_9$H$_7$O$_4$Cl found (calc) C, 39.77 (39.97); H, 2.34 (2.61); Cl, 12.94 (13.11).

Preparation of [Fe(C$_5$H$_4$—CO$_2$Me)(CO)$_2$I] CORM-391

800 mg (1.70 mmol) of [Fe(C$_5$H$_4$—CO$_2$Me)(CO)$_2$]$_2$ was dissolved in 40 ml of DCM, under argon. A solution of 497 mg (1.96 mmol) of I$_2$ in 20 ml of DCM was then added drop-wise with stirring. After complete addition, stirring was continued for a further 3 h, after which time reaction was shown to be complete by IR spectroscopy. The reaction solution was then transferred to a separating funnel and more DCM was added. It was then washed with three portions of de-oxygenated Na$_2$S$_2$O$_3$ (aq) and once with de-oxygenated water. It was then dried (MgSO$_4$), filtered, and then the solvent removed on a rotary evaporator to give a black solid. This was dried under vacuum.

1.03 g of product obtained. $M^r$=361.90. Yield 84%. X-ray quality crystals were obtained from a diethyl ether solution at −18° C.

$^1$H NMR (CD$_2$Cl$_2$): δ(ppm) 3.90 (s, Me 3H), 5.13 (s, Cp 2H), 5.72 (s, Cp 2H)

$^{13}$C NMR (CD$_2$Cl$_2$): δ(ppm) 52.6 (Me), 83.7 (Cp), 89.9 (Cp), 164.2 (C=O), 212.0 (CO)

$^{17}$O NMR (CD$_2$Cl$_2$): 5(ppm) 384.9 (CO)

IR (CH$_2$Cl$_2$) ν(cm$^{-1}$): 2050 (s), 2010 (s)

Mass Spec (m/z): 362 (M$^+$), 334 (M$^+$-CO), 306 (M$^+$-2C0)

Elemental: FeC$_9$H$_7$O$_4$I found (calc) C, 29.86 (29.87); H, 1.71 (1.95), I, 35.06 (35.07).

This compound is reported in Reference 18.

REFERENCES

1. Piantadosi C A. Toxicity of carbon monoxide: hemoglobins vs. histotoxic mechanisms. In: Carbon monoxide. (Edited by Penney D G). 1996; Chapter 8.
2. Sjostrand T. Endogenous formation of carbon monoxide in man under normal and pathological conditions. Scan J Clin Lab Invest 1949; 1: 201-14.
3. Coburn R F, Blakemore W S, Forster R E. Endogenous carbon monoxide production in man. J Clin Invest 1963; 42: 1172-8.
4. Coburn R F, Williams W J, Forster R E. Effect of erythrocyte destruction on carbon monoxide production in man. J Clin Invest 1964; 43: 1098-103.
5. Coburn R F, Williams W J, Kahn S B. Endogenous carbon monoxide production in patients with hemolytic anemia. J Clin Invest 1966; 45: 460-8.
6. Sjostrand T. The formation of carbon monoxide by in vitro decomposition of haemoglobin in bile pigments. Acta Physiol Scand 1952; 26: 328-33.
7. Coburn R F, Williams W J, White P, Kahn S B. The production of carbon monoxide from hemoglobin in vivo. J Clin Invest 1967; 46: 346-56.
8. Tenhunen R, Marver H S, Schmid R. Microsomal heme oxygenase. Characterization of the enzyme. J Biol. Chem. 1969; 244: 6388-94.
9. Scharf S M, Permutt S, Bromberger-Barnea B. Effects of hypoxic and CO hypoxia on isolated hearts. J Appl Physiol 1975; 39: 752-8.
10. G. L. Grunewald and D. P. Davis. J. Org. Chem., 1978, 43, 3074.
11. N. J. Coville, M. S. Loonat, D. White and L. Carlton, Organometallics, 1992, 11, 1082.
12. D. Catheline and D. Astruc, Organometallics, 1984, 3, 1094-1100.
13. H. H. Hammud and G. M. Moran, J. Organomet. Chem., 1986, 307, 255.
14. E. S. Hand, S. C. Johnson and D. C. Baker, J. Org. Chem., 1997, 62, 1348-1355.
15. P.-H. Yeh, Z. Pang and R. F. Johnston, J. Organomet. Chem., 1996, 509, 123-129.
16. R. A. L. Gendron, D. J. Berg and T. Barclay, Can. J. Chem., 2002, 80, 1285-1292.
17. A. Chaloyard, N. el Murr, Inorg. Chem., 1980, 18, 3217.
18. N. J. Coville, M. S. Loonat, D. White and L. Carlton, *Organometallics*, 1992, 11, 1082.
19. P. Hublau, C. Sergheraert, L. Ballester and M. Dautrevaux, *Eur. J. Med. Chem.*, 1983, 18, 131.
20. M. Le Plouzennec, F. Le Moigne and R. Dabard, *J. Organomet. Chem.*, 1977, 132, 409.

The invention claimed is:

1. A pharmaceutical composition for delivery of CO, comprising as an active ingredient a compound represented by formula (I) or formula (II) below:

wherein:—

M is a transition metal selected from group 6, 7, 8 or 9 of the periodic table;

Y is a counteranion;

q is the charge of Y and is selected from 1, 2 or 3;

x is 2, 3 or 4;

z is 0 or 1, and x, z and p satisfy the equation $$13-g=2x-z+p$$

where g is the group number of M in the periodic table, and where p is 0 or 1 when g is 6; or p is 0 when g is 7, 8 or 9;

L is a ligand selected from H, halide, $C_{1-7}$ alkyl, $C_{6-14}$ aryl, $C_{1-7}$ alkoxy, $C_{6-14}$ aryloxy, $C_{1-7}$ alkylthio, $C_{5-10}$ arylthio, acyloxy (—OC(=O)$R^5$), amido (—C(=O)$NR^5R^6$), acylamido (—$NR^5$C(=O)$R^6$), aminocarbonyloxy(—OC(=O)$NR^5R^6$) and aminothiocarbonylthiol (—SC(=S)$NR^5R^6$);

$$[CpM'(CO)_2L']+z(Y^{-q})_{z/q} \quad (II)$$

wherein

M' is Fe or Ru;

Y is a counteranion;

q is the charge of Y and is selected from 1, 2 or 3;

L' is a ligand selected from either a first group consisting of H, halide, —$NO_2$, —ONO, -$ONO_2$, —OH, —SCN, —NCS, —OCN, —NCO, $C_{1-7}$ alkyl, $C_{6-14}$ aryl, $C_{1-7}$ alkoxy, $C_{6-14}$ aryloxy, $C_{1-7}$ alkylthio, $C_{5-10}$ arylthio, acyloxy(—OC(=O)$R^7$), amido (—C(=O)$NR^7R^8$), acylamido (—$NR^7$C(=O)$R^8$), aminocarbonyloxy (—OC(=O)$NR^7R^8$), (SC(=O)$R^7$), —SC(S)$R^7$, —SC(S)O$R^7$, —SC(O)$NR^7R^8$, —SC(O)O$R^7$, aminothiocarbonylthiol (—SC(=S)$NR^7R^8$), —OC(=S)$R^7$, —N(C(=O)$R^7$)$_2$, and —C(O)(O$R^7$); —O—$PR^7R^8R^9$, —O—$PR^7_{3-n}$(O$R^8$)n where n=1, 2 or 3, —O—$PR^7_{(3-n)}$($NR^8R^9$)n where n=1, 2 or 3; or a second group consisting of O$R^7R^8$, O=C$R^7R^8$, O=C($NR^7R^8$)$R^9$, O=C(O$R^7$)$R^8$, O=S$R^7R^8$, O=S(O)$R^7R^8$, S$R^7R^8$, S(O)$R^7R^8$, S=C$R^7R^8$, S=C($NR^7R^8$)$R^9$, S=C(O$R^7$)$R^8$, $NR^7R^8R^9$, NC$R^7$, N* where N is an aromatic nitrogen atom in an aromatic ring represented by N*, $PR^7R^8R^9$, $PR^7_{(3-n)}$(O$R^8$)n where n=1, 2 or 3, $PR^7_{(3-n)}NR^8R^9$)n where n=1, 2 or 3, O=$PR^7R^8R^9$, O=$PR^7_{(3-n)}$(O$R^8$)$_n$ where n=1, 2 or 3, O=$PR^7_{(3-n)}$($NR^8R^9$)$_n$ where n=1, 2 or 3;

$R^7$, $R^8$ and $R^9$ are independently selected from H, optionally substituted $C_{1-7}$ alkyl and optionally substituted $C_{6-20}$ aryl, with the proviso that any two of $R^7$, $R^8$ and $R^9$ which are both attached to the same O, N or S atom may, taken together with that atom, form an optionally substituted heterocyclic ring having 5, 6 or 7 ring atoms;

z=0 when L' is from said first group and z=1 when L' is from said second group; and wherein in formula (I) and formula (II):—

Cp is selected from:

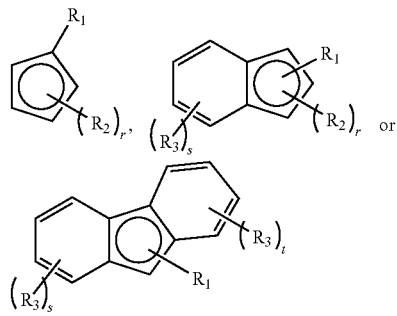

where r, s and t are each independently selected from 1, 2, 3 or 4; and $R_1$ is either:

-[Alk]$_n$—O—C(O)-$Q_1$, -[Alk]$_n$—C(O)—O-$Q_1$, -[Alk]$_n$-$NR_4$—C(O)-$Q_1$ or n is 0 or 1;

Alk is a $C_{1-28}$ alkylene group;

$Q_1$ and $Q_2$ are each independently selected from H, optionally substituted $C_{1-22}$ alkyl and an optionally substituted $C_{6-25}$ aryl group;

each $R_2$ is independently selected from $R_1$, H, $C_{1-22}$ alkyl, $C_{6-25}$ aryl, $C_{1-7}$ alkoxy, $C_{5-10}$ aryloxy, halide, formyl, $C_{1-7}$ alkylacyl and $C_{6-20}$ arylacyl;

$R_4$ is selected from H, $C_{1-22}$ alkyl and $C_{6-25}$ aryl;

each $R_3$ is independently selected from H, hydroxy, nitro, cyano, halide, sulfhydryl, $C_{1-22}$ alkyl, $C_{6-25}$ aryl, $C_{1-7}$ alkoxy, $C_{5-10}$ aryloxy, formyl, $C_{1-7}$ alkylacyl, $C_{6-20}$ arylacyl, $C_{1-7}$ alkylthio, $C_{5-10}$ arylthio, carboxylic acid (—C(=O)OH), ester (—C(=O)O$R^5$), acyloxy(—OC(=O)$R^5$), amido (—C(=O)$NR^5R^6$), acylamido (—$NR^5$C(=O)$R^6$) and amino (—$NR^5R^6$); and $R^5$ and $R^6$ are independently selected from H, $C_{1-7}$ alkyl and $C_{6-20}$ aryl.

2. A pharmaceutical composition according to claim 1, wherein M or M' is Fe.

3. A pharmaceutical composition according to claim 1, wherein said compound is represented by formula (I) and z is 1.

4. A pharmaceutical composition according to claim 1, wherein Y is selected from halide, sulphonate, borate, hexafluorophosphate, perhalate, sulphate, phosphate, a carboxylate anion of an organic acid or of an amino acid.

5. A pharmaceutical composition according to claim 1, wherein said compound is represented by formula (I) and g is 6 and p is 1.

6. A pharmaceutical composition according to claim 5, wherein L is selected from H, halide, $C_{1-7}$ alkyl, $C_{6-14}$ aryl, $C_{1-7}$ alkoxy and $C_{6-14}$ aryloxy.

7. A pharmaceutical composition according to claim 1, wherein said compound is represented by formula (II) and L' is selected from halide and —$ONO_2$.

8. A pharmaceutical composition according to claim 1, wherein Cp is

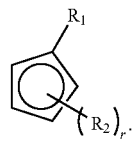

9. A pharmaceutical composition according to claim 8, wherein r is 1 or 4.

10. A pharmaceutical composition according to claim 1, wherein Cp is

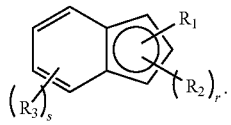

11. A pharmaceutical composition according to claim 10, wherein r is 1.

12. A pharmaceutical composition according to claim 10, wherein s is 1, 2 or 3.

13. A pharmaceutical composition according to claim 1, wherein $R_3$ is selected from H, hydroxy, nitro, cyano, halide, $C_{1-22}$ alkyl, $C_{6-25}$ aryl, $C_{1-7}$ alkoxy, $C_{5-10}$ aryloxy and amino (—$NR^5R^6$).

14. A pharmaceutical composition according to claim 1, wherein $R_2$ is identical to $R_1$.

15. A pharmaceutical composition according to claim 1, wherein $R_2$ is selected from H, $C_{1-22}$ alkyl and $C_{9-25}$ aryl.

16. A pharmaceutical composition according to claim 1, wherein $R_1$ is -[Alk]$_n$—O—C(O)-$Q_1$ unit and n is 1.

17. A pharmaceutical composition according to claim 16, wherein $Q_1$ is selected from H, substituted $C_{1-22}$ alkyl and optionally substituted $C_{6-25}$ aryl group.

18. A pharmaceutical composition according to claim 17, wherein the substituent in said substituted $C_{1-22}$ alkyl and said optionally substituted $C_{6-25}$ aryl group is selected from a-amino acid, hydroxy, ether, ester, oxo, acyloxy, amino, amido and acylamido.

19. A pharmaceutical composition according to claim 1, wherein $R_1$ is -[Allk]$_n$—C(O)—O-$Q_1$ and n is 1.

20. A pharmaceutical composition according to claim 19, wherein $Q_1$ is selected from H, optionally substituted $C_{1-10}$ alkyl and optionally substituted $C_{6-14}$ aryl.

21. A pharmaceutical composition according to claim 1, wherein -[Alk]$_n$-C(O)—O-$Q_1$ and n is 0.

22. A pharmaceutical composition according to claim 21, wherein $Q_1$ is selected from H, optionally substituted $C_{1-22}$ alkyl and an optionally substituted $C_{6-25}$ aryl group.

23. A pharmaceutical composition according to claim 1 adapted for delivery by an oral, intravenous, transdermal, subcutaneous, nasal, inhalatory, intramuscular, intraperitoneal or suppository route.

24. A compound according to formula (III)

$$[CpFe(CO)_3]^{+1}(Y^{-q})_{1/q} \qquad (III)$$

wherein

Y is a counteranion;

q is the charge of Y and is selected from 1, 2 or 3; and Cp is selected from:

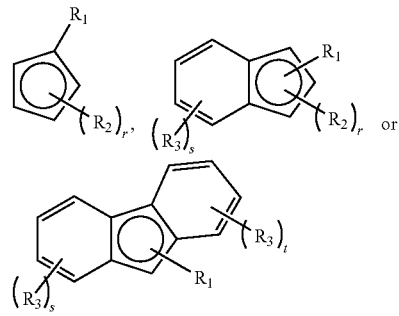

where r, s and t are each independently selected from 1, 2, 3 or 4; and $R_1$ is either:

-[Alk]$_n$-O—C(O)-$Q_1$, -[Alk]$_n$-C(O)—O-$Q_1$, -[Alk]$_n$-$NR_4$—C(O)-$Q_1$ or -[Alk]$_n$-C(O)-$NQ_1 Q_2$, n is 0 or 1;

Alk is a $C_{1-28}$ alkylene group;

$Q_1$ and $Q_2$ are each independently selected from H, optionally substituted $C_{1-22}$ alkyl and an optionally substituted $C_{6-25}$ aryl group;

each $R_2$ is independently selected from $R_1$, H, $C_{1-22}$ alkyl, $C_{6-25}$ aryl, $C_{1-7}$ alkoxy, $C_{5-10}$ aryloxy, halide, formyl, $C_{1-7}$ alkylacyl and $C_{6-20}$ arylacyl;

$R_4$ is selected from H, $C_{1-22}$ alkyl and $C_{6-25}$ aryl;

each $R_3$ is independently selected from H, hydroxy, nitro, cyano, halide, sulfhydryl, $C_{1-22}$ alkyl, $C_{6-25}$ aryl, $C_{1-7}$ alkoxy, $C_{5-10}$ aryloxy, formyl, $C_{1-7}$ alkylacyl, $C_{6-20}$ arylacyl, $C_{1-7}$ alkylthio, $C_{5-10}$ arylthio, carboxylic acid (—C(=O)OH), ester (—C(=O)OR$^5$), acyloxy(—OC(=O)R$^5$), amido (—C(=O)NR$^5R^6$), acylamido (—NR$^5$C(=O)R$^6$) and amino (—NR$^5R^6$); and $R^5$ and $R^6$ are independently selected from H, $C_{1-7}$ alkyl and $C_{6-20}$ aryl.

* * * * *